United States Patent
Hakim

(10) Patent No.: US 11,311,704 B2
(45) Date of Patent: *Apr. 26, 2022

(54) EXTERNALLY PROGRAMMABLE VALVE ASSEMBLY

(71) Applicant: CEREDYN BIOTECHNOLOGY LLC, Miami, FL (US)

(72) Inventor: Carlos A. Hakim, Coconut Grove, FL (US)

(73) Assignee: CEREDYN BIOTECHNOLOGY LLC, Miami, FL (US)

( * ) Notice: Subject to any disclaimer, the term of this patent is extended or adjusted under 35 U.S.C. 154(b) by 421 days.

This patent is subject to a terminal disclaimer.

(21) Appl. No.: 16/424,156

(22) Filed: May 28, 2019

(65) Prior Publication Data

US 2019/0344058 A1    Nov. 14, 2019

Related U.S. Application Data

(63) Continuation of application No. 14/213,480, filed on Mar. 14, 2014, now Pat. No. 10,322,267.

(60) Provisional application No. 61/791,922, filed on Mar. 15, 2013.

(51) Int. Cl.
    *A61M 27/00*    (2006.01)
(52) U.S. Cl.
    CPC ..... *A61M 27/006* (2013.01); *A61M 2027/004* (2013.01); *A61M 2205/3515* (2013.01); *A61M 2205/3523* (2013.01)

(58) Field of Classification Search
    CPC .......... A61M 27/006; A61M 2027/004; A61M 2205/3515; A61M 2205/3523
    See application file for complete search history.

(56) References Cited

U.S. PATENT DOCUMENTS

| | | |
|---|---|---|
| 2,969,066 A | 1/1961 | Holter et al. |
| 3,288,142 A | 11/1966 | Hakim |
| 3,595,240 A | 7/1971 | Mishler |
| 3,683,929 A | 8/1972 | Holter |
| 3,886,948 A | 6/1975 | Hakim |
| 3,889,687 A | 6/1975 | Harris et al. |
| 3,894,541 A | 7/1975 | El-Shafei |
| 3,958,562 A | 5/1976 | Hakim et al. |
| 4,106,510 A | 8/1978 | Hakim et al. |
| 4,197,875 A | 4/1980 | Schieferstein et al. |

(Continued)

FOREIGN PATENT DOCUMENTS

| | | |
|---|---|---|
| DE | 4401422 B4 | 2/2004 |
| EP | 0421557 A2 | 4/1991 |

(Continued)

OTHER PUBLICATIONS

Partial Supplementary European Search Report for application No. 14763558.5 dated Sep. 20, 2016.

(Continued)

*Primary Examiner* — Ariana Zimbouski
(74) *Attorney, Agent, or Firm* — Lando & Anastasi, LLP

(57) ABSTRACT

An externally programmable shunt valve assembly that includes a magnetic rotor that is operable in response to an externally applied magnetic field and configured to increase or decrease the working pressure of the shunt valve assembly in finite increments.

17 Claims, 48 Drawing Sheets

(56) References Cited

U.S. PATENT DOCUMENTS

| | | | |
|---|---|---|---|
| 4,212,589 A * | 7/1980 | Bosio | F04B 43/113 417/12 |
| 4,261,341 A | 4/1981 | Hakim et al. | |
| 4,312,293 A | 1/1982 | Hakim | |
| 4,332,255 A | 6/1982 | Hakim et al. | |
| 4,387,715 A | 6/1983 | Hakim et al. | |
| 4,551,128 A | 11/1985 | Hakim et al. | |
| 4,557,721 A | 12/1985 | Hooven | |
| 4,565,390 A | 1/1986 | Merkle | |
| 4,595,390 A | 6/1986 | Hakim et al. | |
| 4,615,691 A | 10/1986 | Hakim et al. | |
| 4,772,257 A | 9/1988 | Hakim et al. | |
| 4,787,886 A | 11/1988 | Cosman | |
| 5,069,663 A | 12/1991 | Sussman | |
| 5,304,114 A | 4/1994 | Cosman et al. | |
| 5,928,182 A | 7/1999 | Kraus et al. | |
| 6,126,628 A | 10/2000 | Nissels | |
| 6,283,934 B1 | 9/2001 | B.o slashed.rgesen | |
| 6,439,538 B1 | 8/2002 | Ito | |
| 6,685,638 B1 | 2/2004 | Taylor et al. | |
| 6,871,740 B1 | 3/2005 | Cao | |
| 6,910,906 B2 | 6/2005 | Schorn | |
| 6,966,537 B2 | 11/2005 | Sundararajan | |
| 7,037,288 B2 | 5/2006 | Rosenberg et al. | |
| 7,318,813 B2 | 1/2008 | Rosenberg | |
| 7,334,582 B2 | 2/2008 | Bertrand et al. | |
| 7,334,594 B2 | 2/2008 | Ludin | |
| 7,390,310 B2 | 6/2008 | McCusker et al. | |
| 7,471,730 B2 | 12/2008 | Adachi | |
| 7,510,533 B2 | 3/2009 | Mauge et al. | |
| 7,559,912 B2 | 7/2009 | McCusker et al. | |
| 7,585,280 B2 | 9/2009 | Wilson et al. | |
| 7,604,658 B2 | 10/2009 | Wilson et al. | |
| 7,617,700 B2 | 11/2009 | Lamb et al. | |
| 7,766,855 B2 | 8/2010 | Miethke | |
| 8,322,365 B2 | 12/2012 | Wilson et al. | |
| 10,322,267 B2 * | 6/2019 | Hakim | A61M 27/006 |
| 2002/0022793 A1 | 2/2002 | Bertrand et al. | |
| 2002/0026139 A1 | 2/2002 | Bertrand et al. | |
| 2002/0058901 A1 | 5/2002 | Marion | |
| 2003/0057392 A1 * | 3/2003 | Ito | A61M 27/006 251/11 |
| 2003/0088151 A1 | 5/2003 | Kung et al. | |
| 2003/0135147 A1 | 7/2003 | Rosenberg et al. | |
| 2003/0139699 A1 | 7/2003 | Rosenberg | |
| 2004/0024346 A1 | 2/2004 | Miethke | |
| 2004/0082900 A1 | 4/2004 | Luttich | |
| 2004/0236264 A1 | 11/2004 | Lecuyer | |
| 2004/0267187 A1 | 12/2004 | Rosenberg | |
| 2005/0004460 A1 | 1/2005 | Taylor et al. | |
| 2005/0043669 A1 | 2/2005 | Rosenberg | |
| 2005/0043670 A1 | 2/2005 | Rosenberg | |
| 2005/0054988 A1 | 3/2005 | Rosenberg et al. | |
| 2005/0187509 A1 | 8/2005 | Wolf | |
| 2006/0004317 A1 | 1/2006 | Mauge et al. | |
| 2006/0089589 A1 | 4/2006 | Portnoy | |
| 2007/0093741 A1 | 4/2007 | Miethke | |
| 2008/0139959 A1 | 6/2008 | Miethke et al. | |
| 2008/0194473 A1 | 8/2008 | Tada et al. | |
| 2009/0005720 A1 | 1/2009 | Ludin et al. | |
| 2010/0056980 A1 | 3/2010 | Negre et al. | |
| 2012/0046596 A1 | 2/2012 | Ludin et al. | |
| 2013/0085441 A1 | 4/2013 | Aihara | |

FOREIGN PATENT DOCUMENTS

| | | |
|---|---|---|
| EP | 1092450 A1 | 4/2001 |
| EP | 2420284 A2 | 2/2012 |
| JP | 2006075275 A | 3/2006 |
| WO | 9953990 A1 | 10/1999 |

OTHER PUBLICATIONS

Extended European Search Report of the European Patent Office from corresponding European Application Serial No. 14763558.5 dated Dec. 21, 2016.

Office Action of the Japanese Patent Office from corresponding JP Application Serial No. 2016-503020 dated Jan. 29, 2018.

* cited by examiner

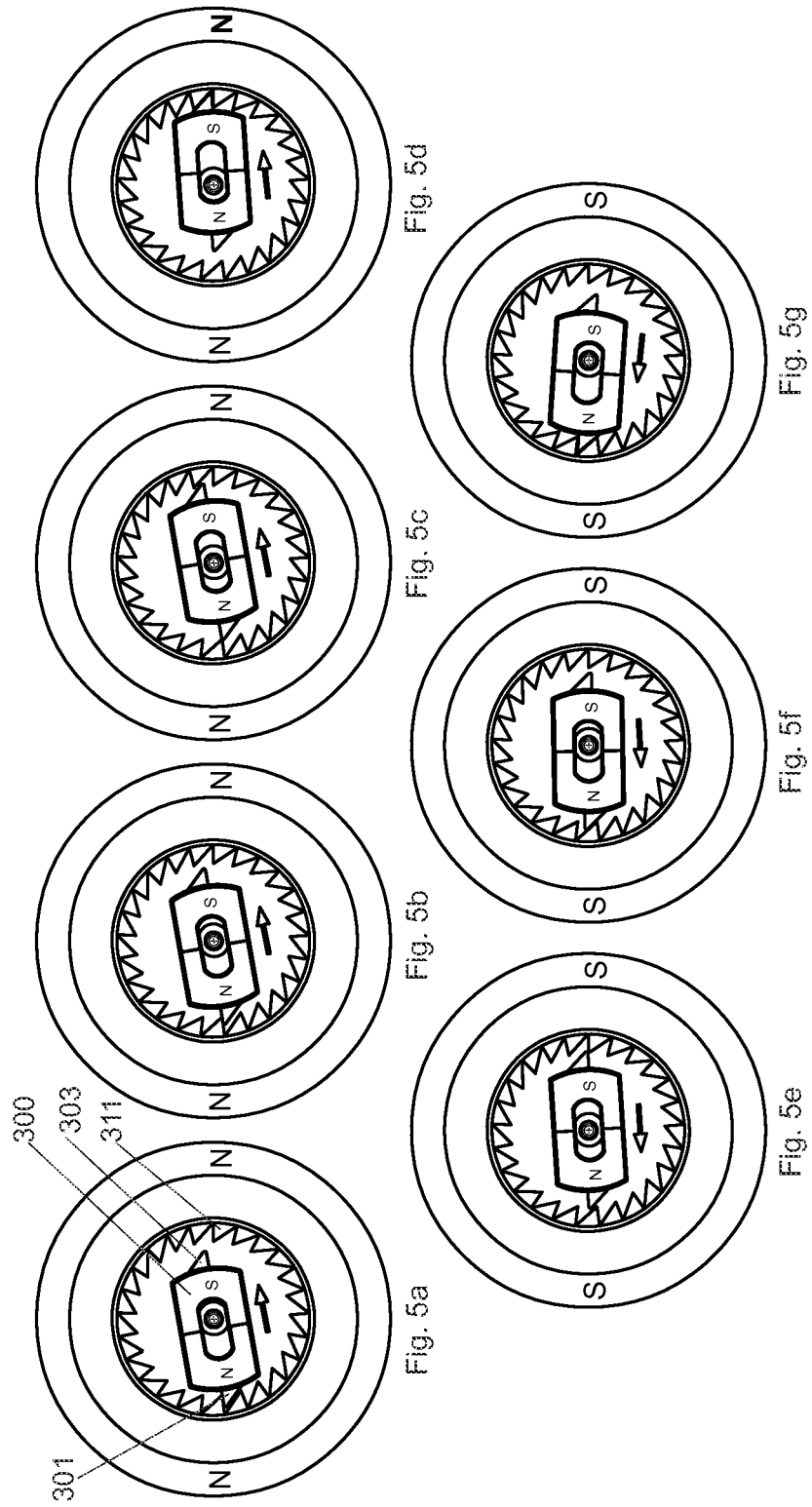

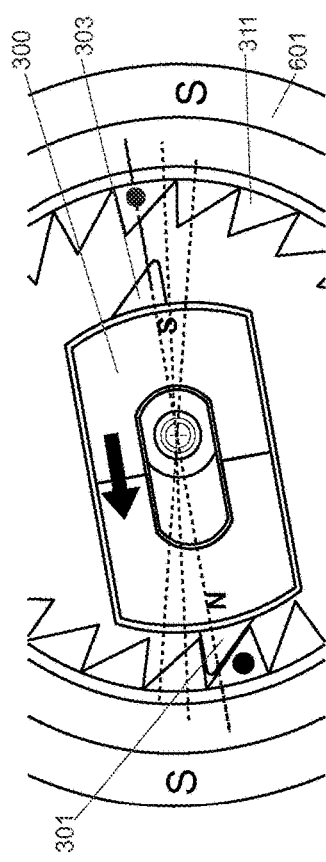
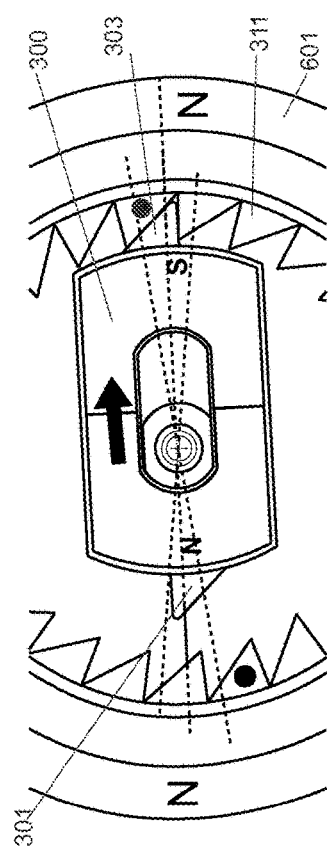
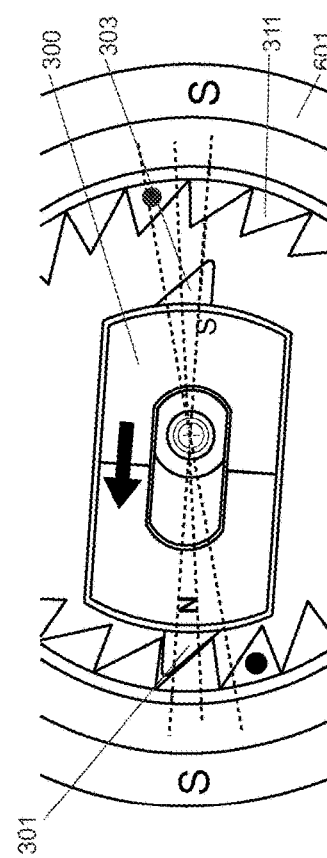

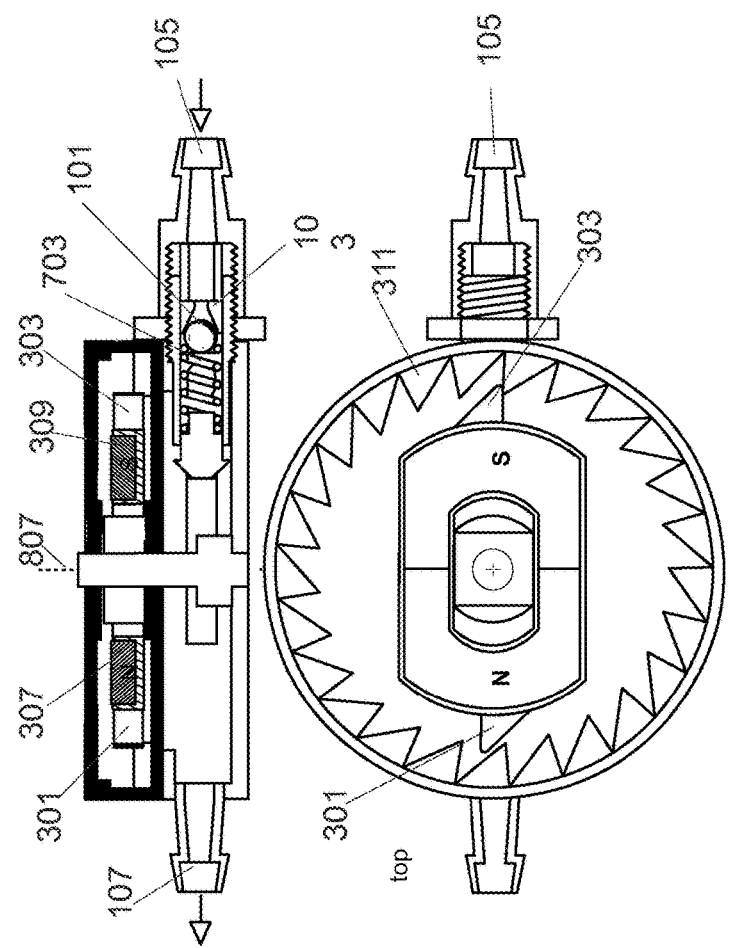
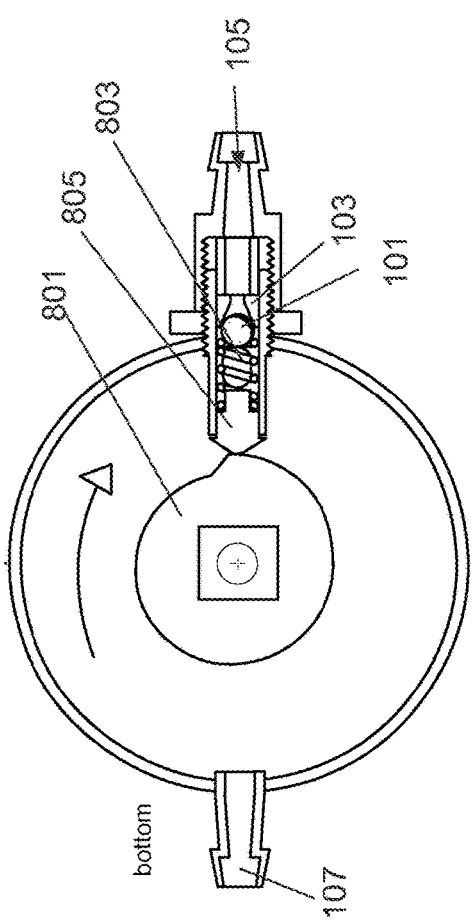
Fig. 8A
Fig. 8B
Fig. 8C

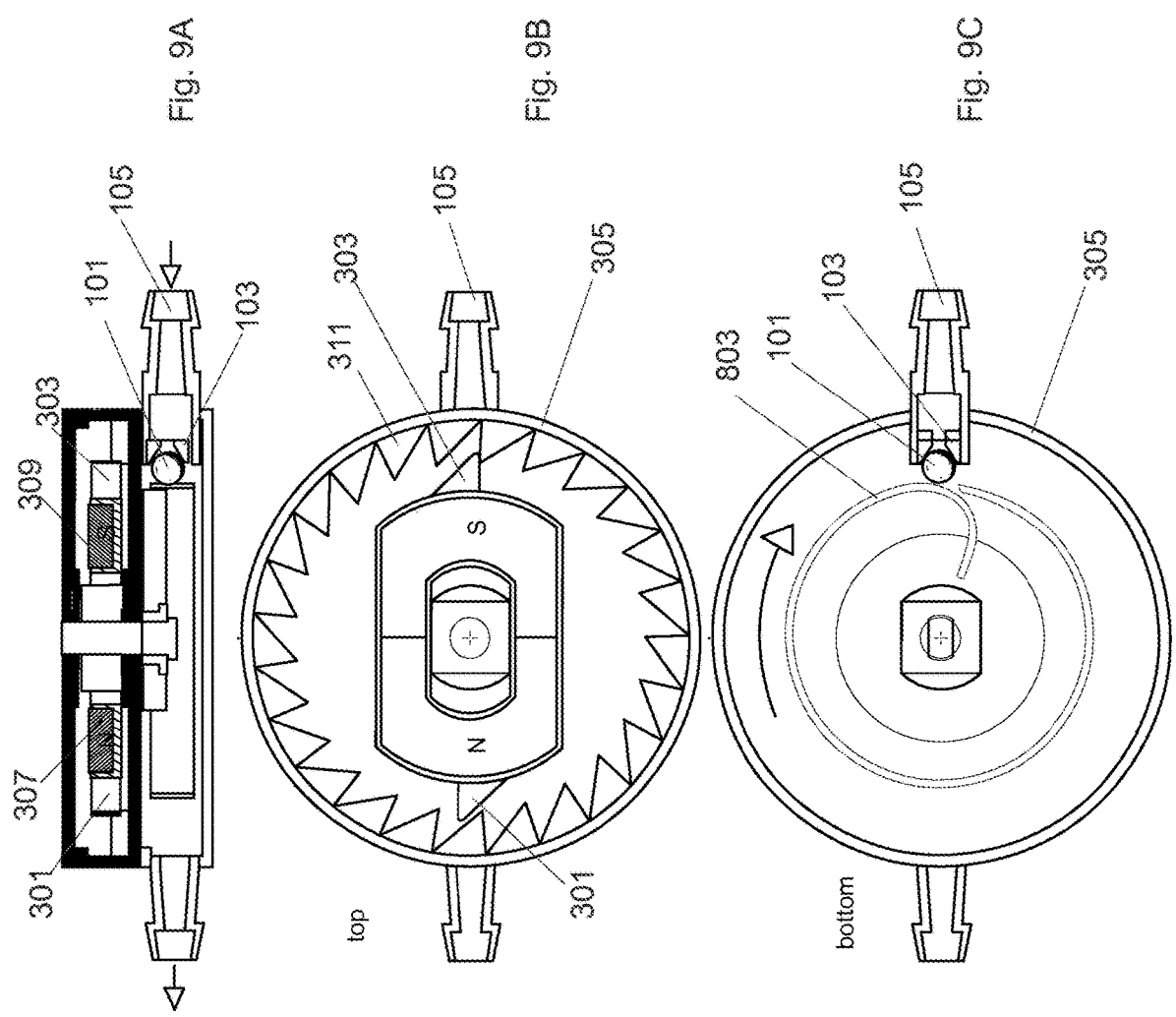

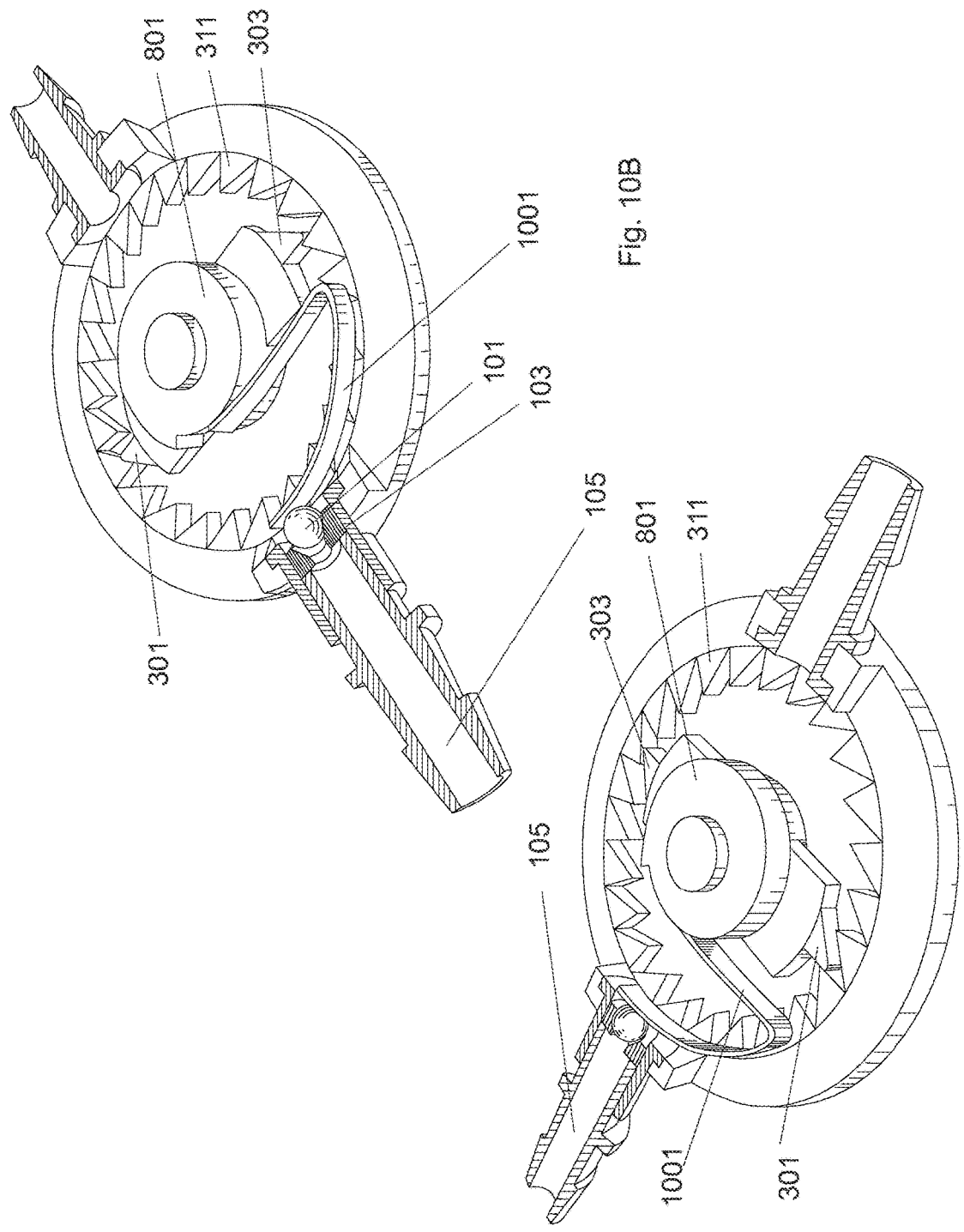

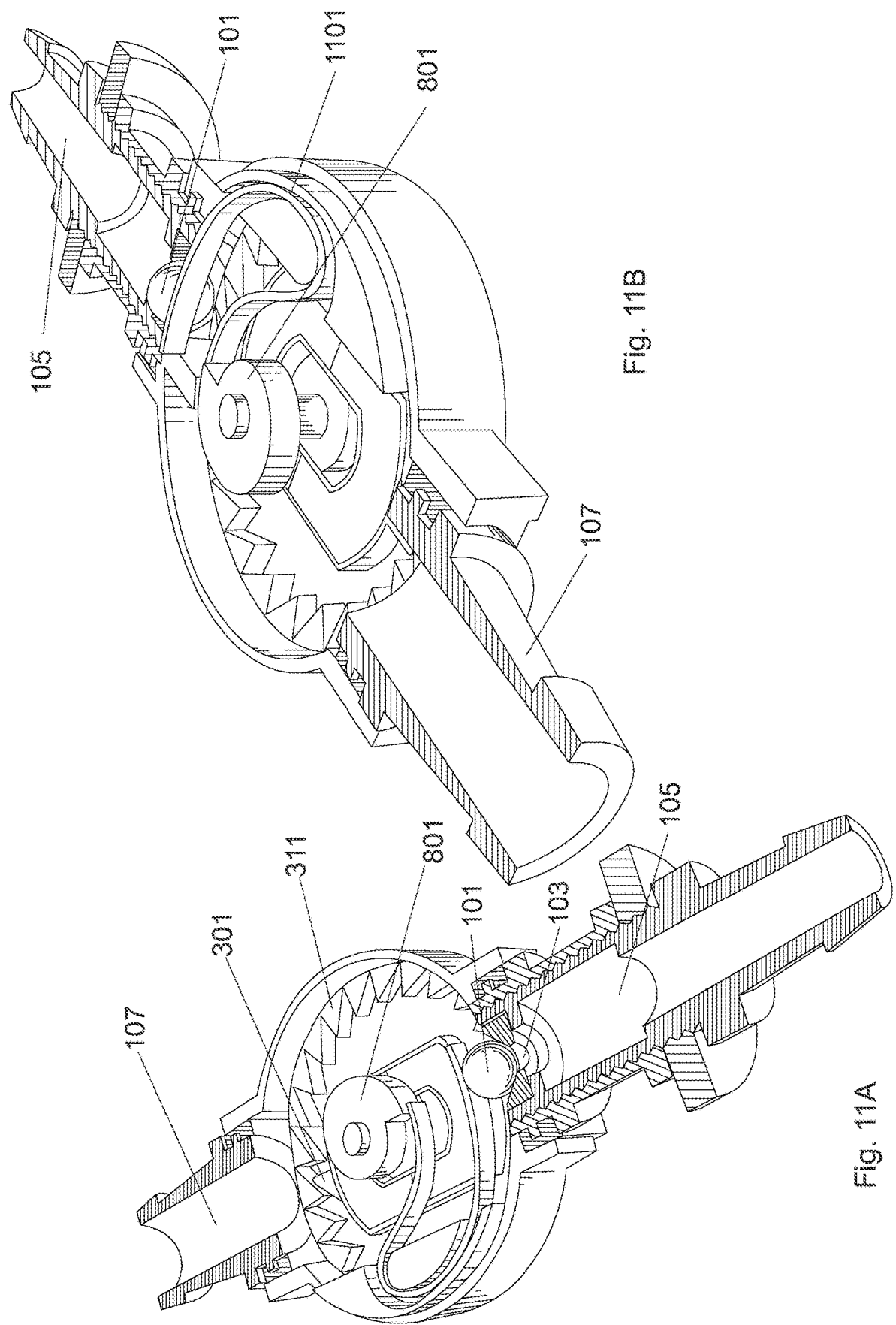

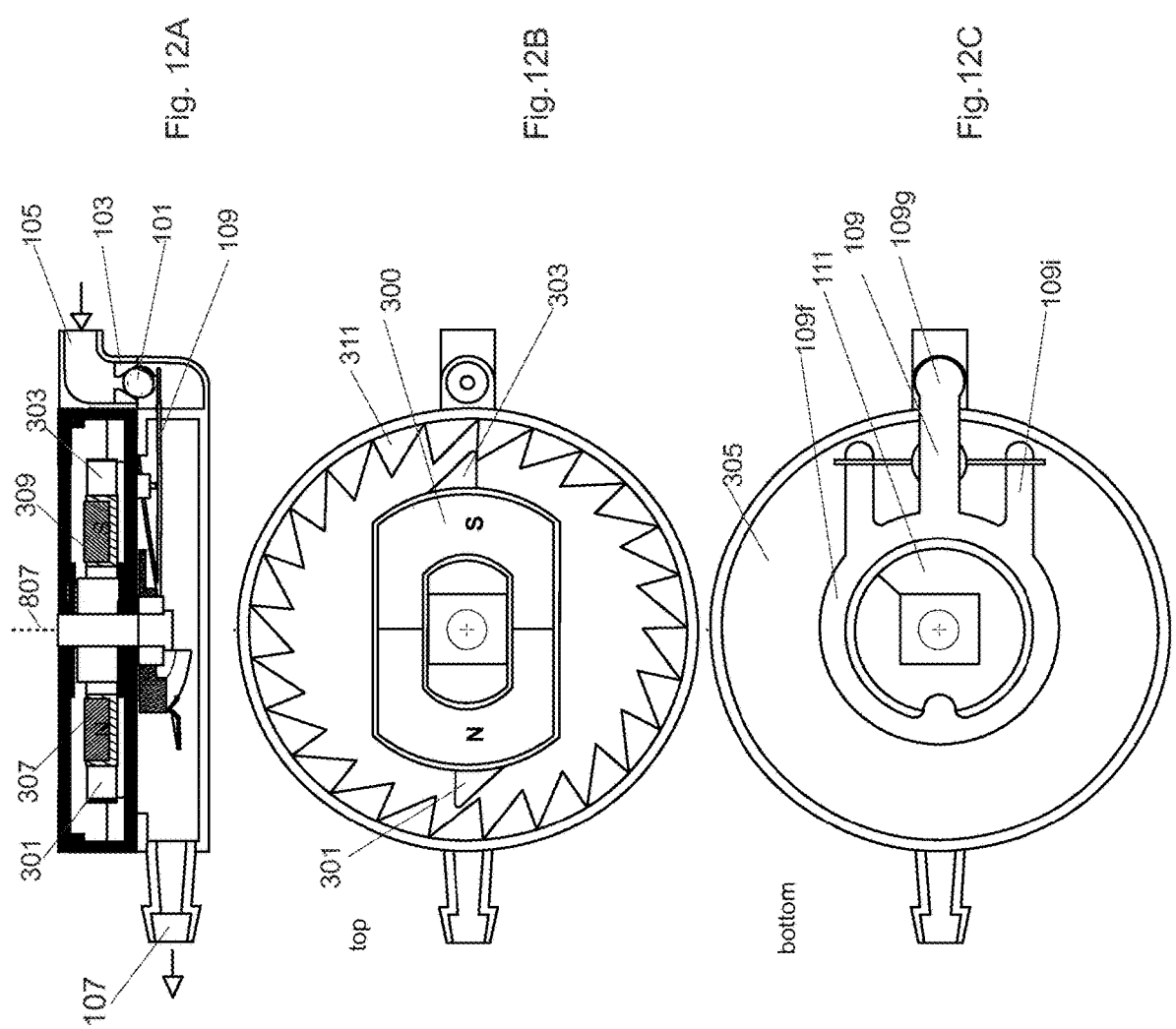

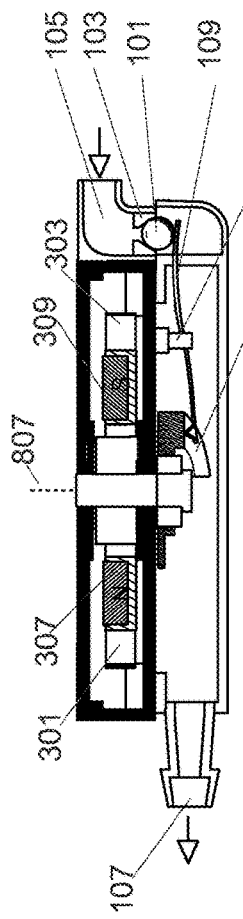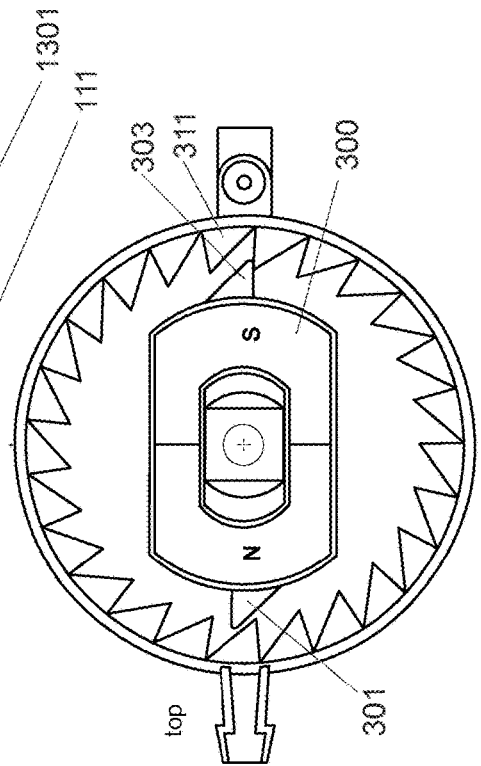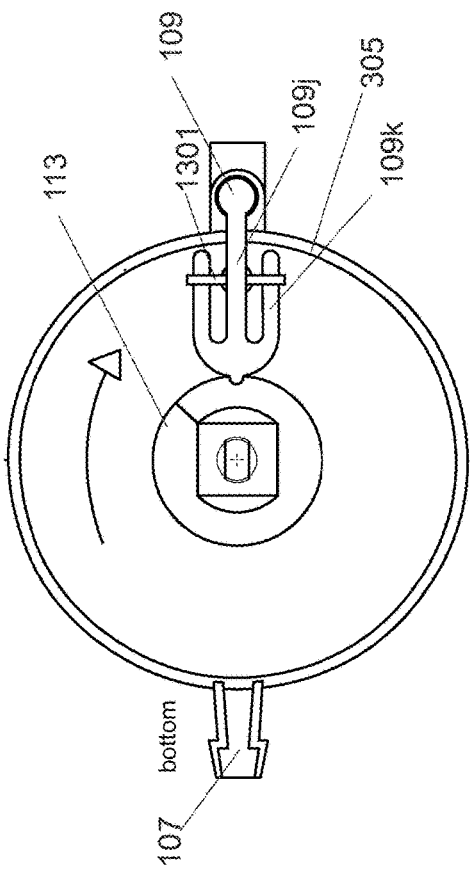
Fig. 13A
Fig. 13B
Fig. 13C

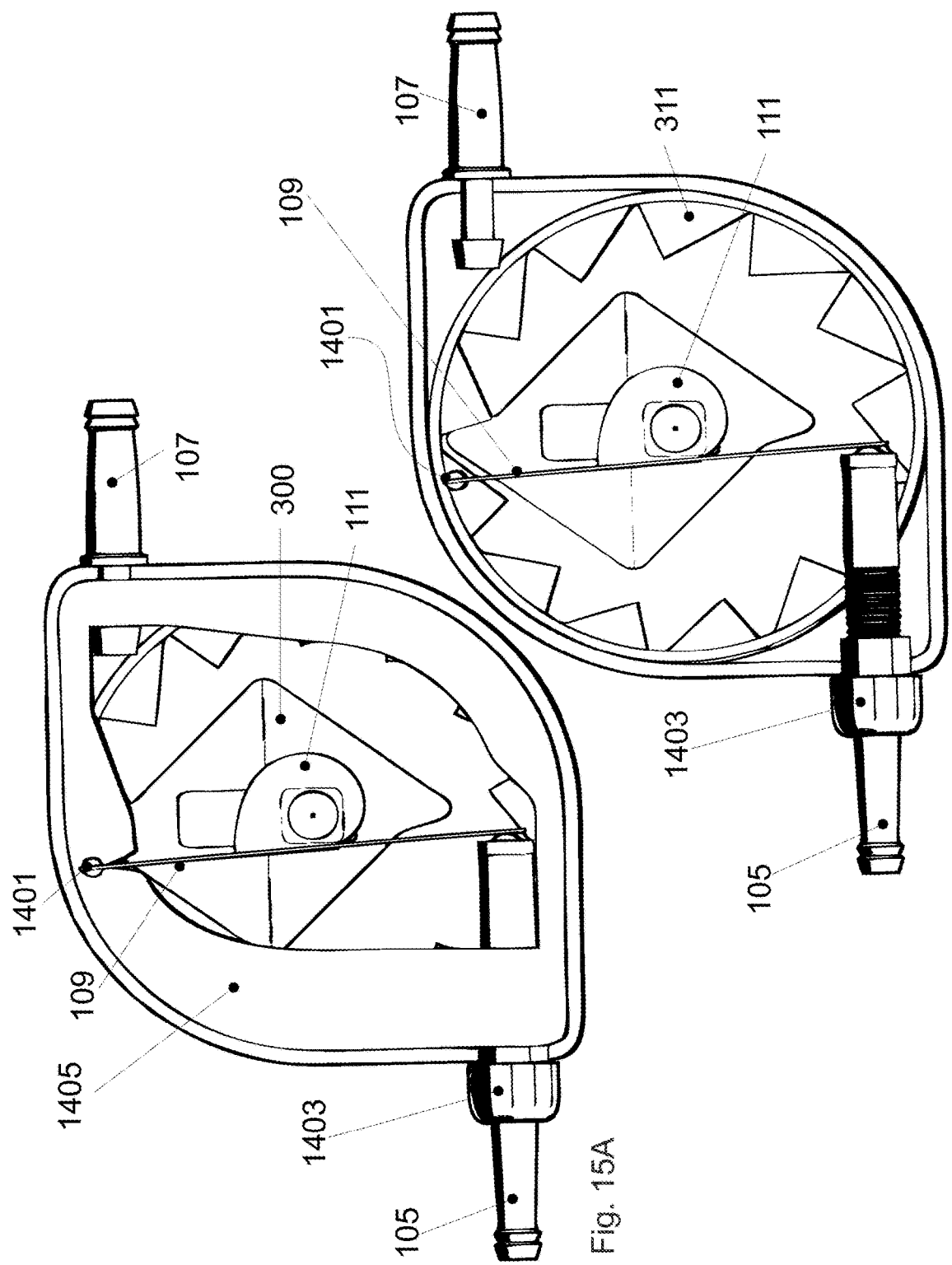

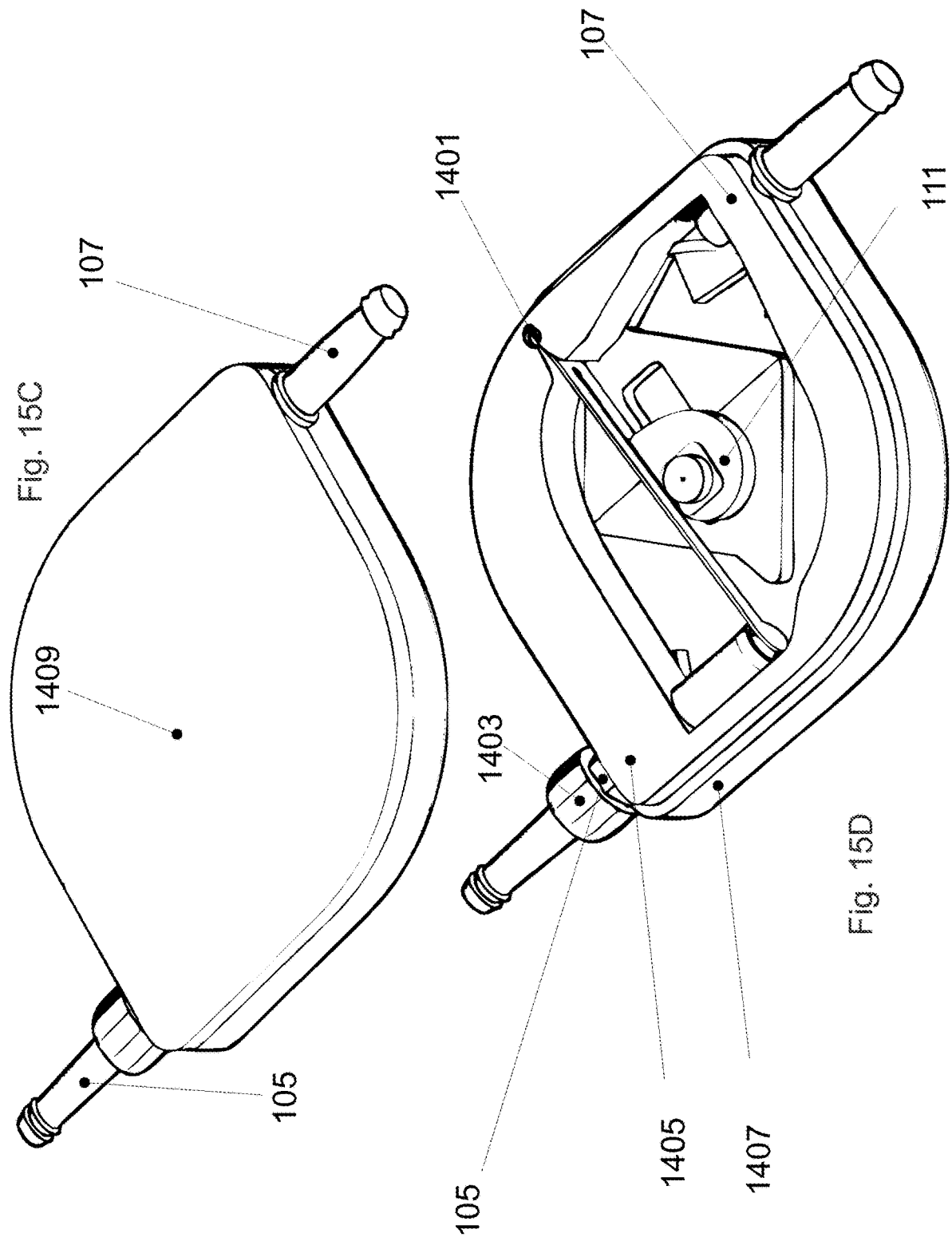

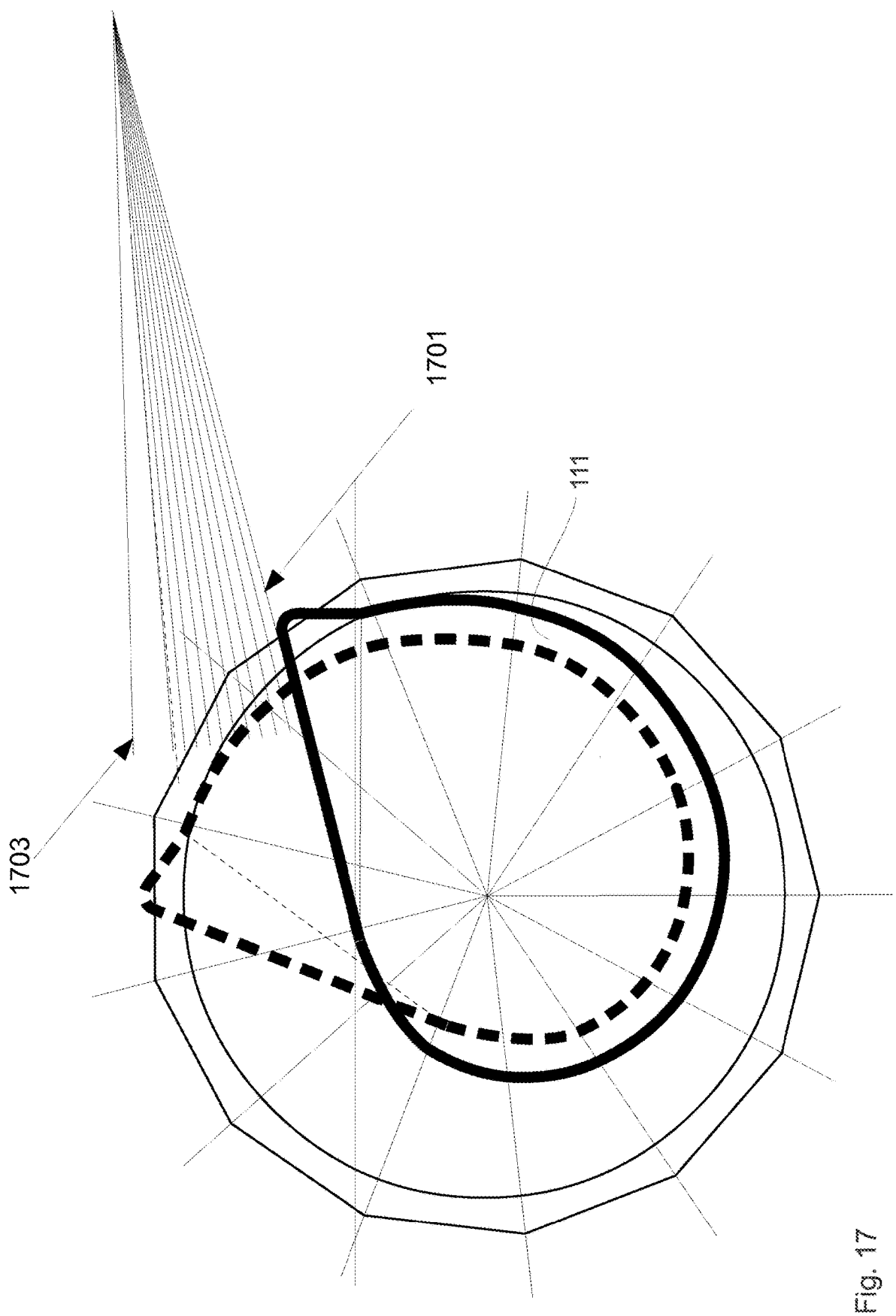

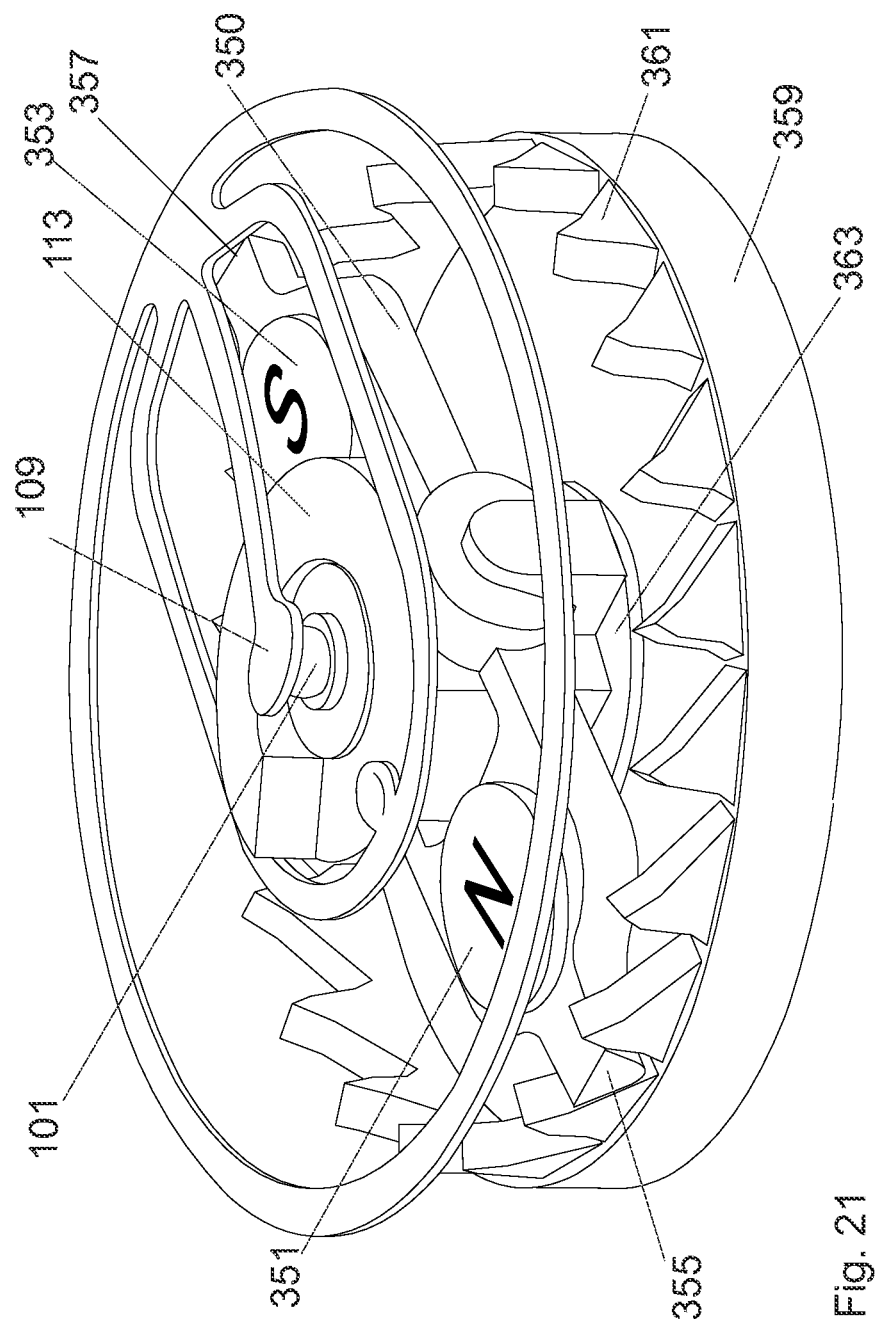

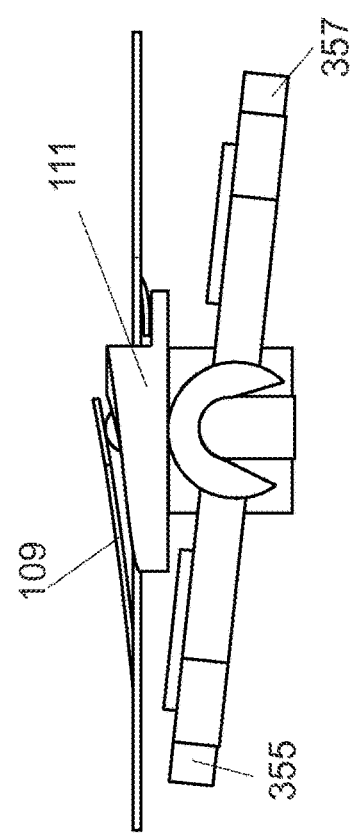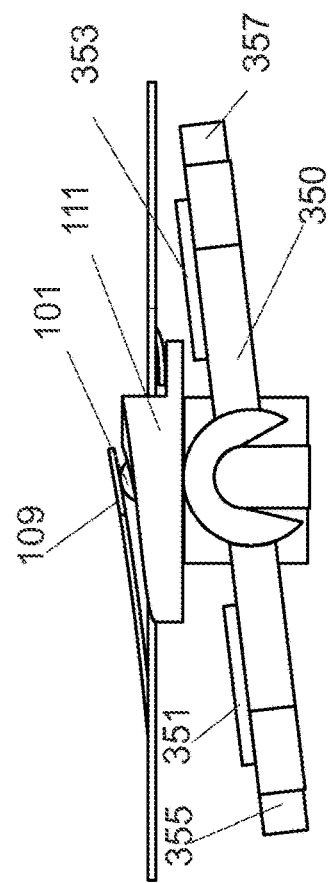

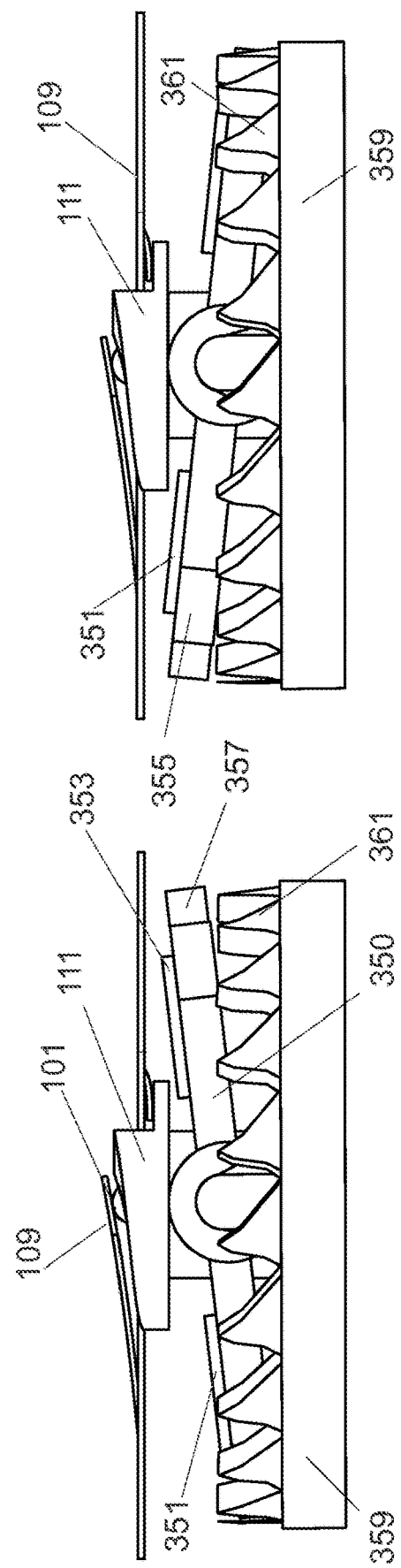

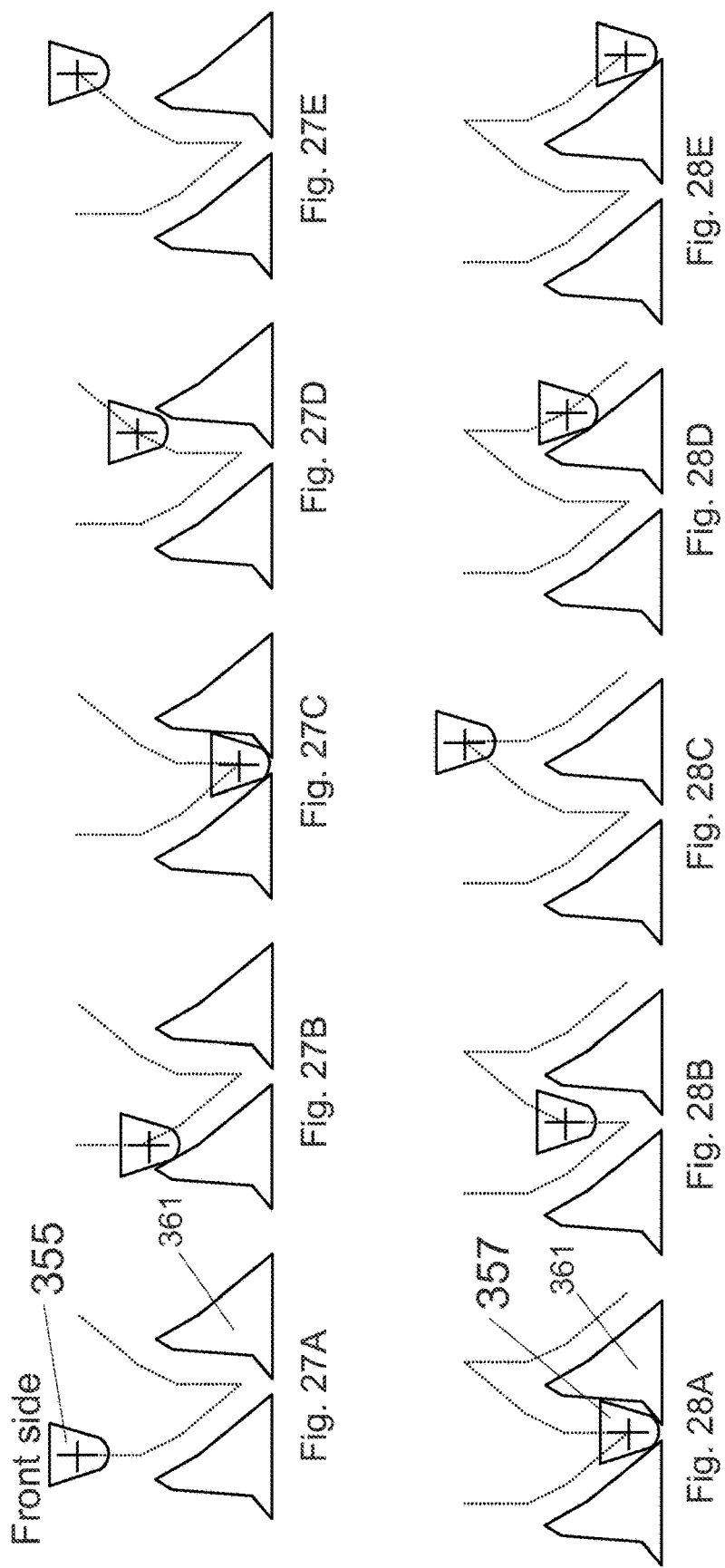

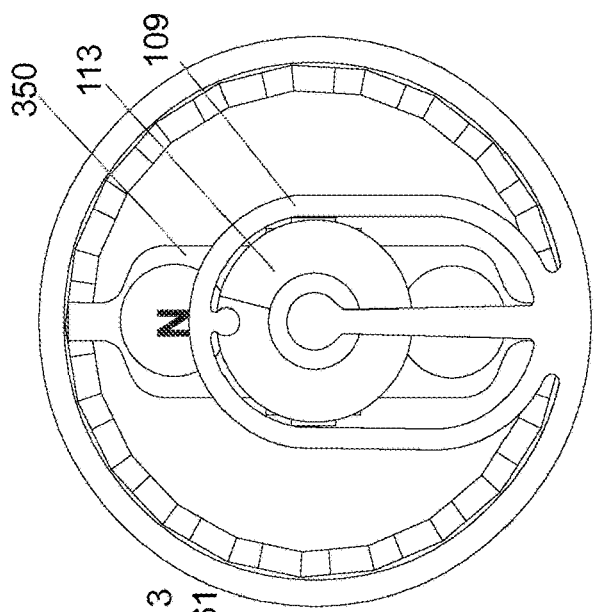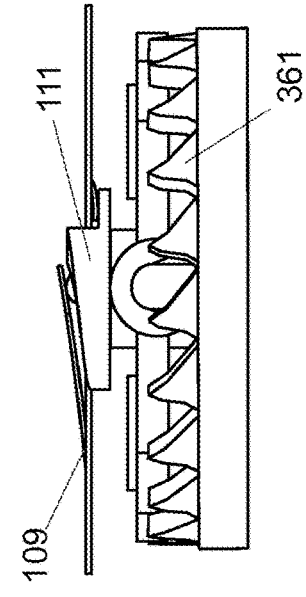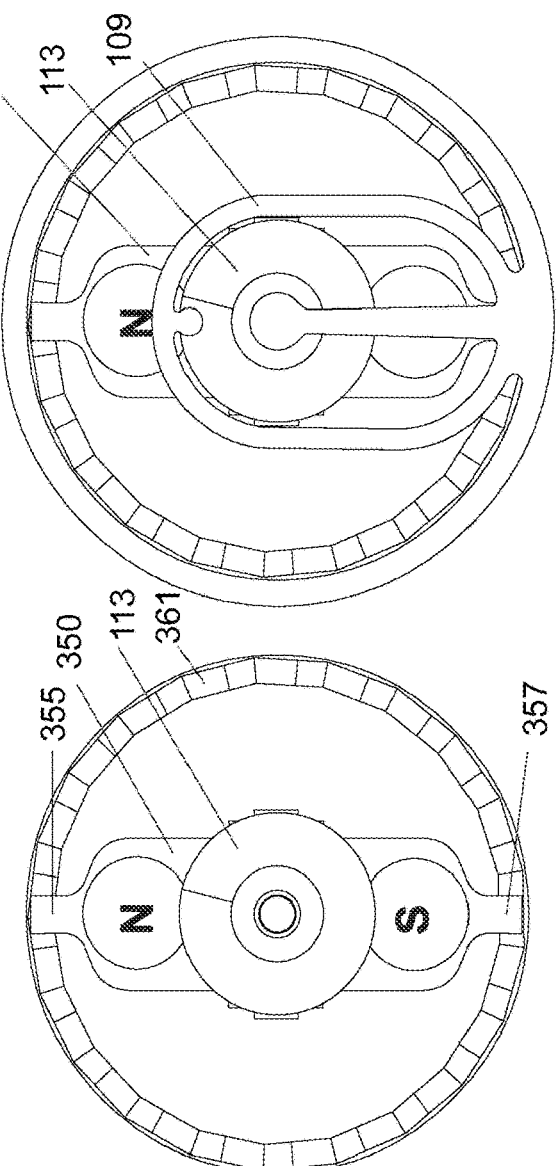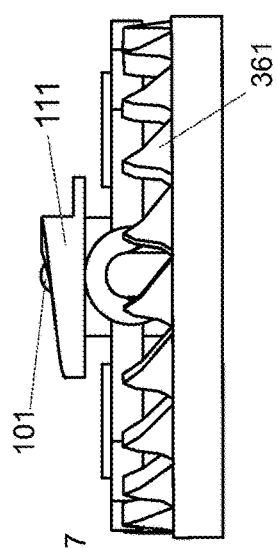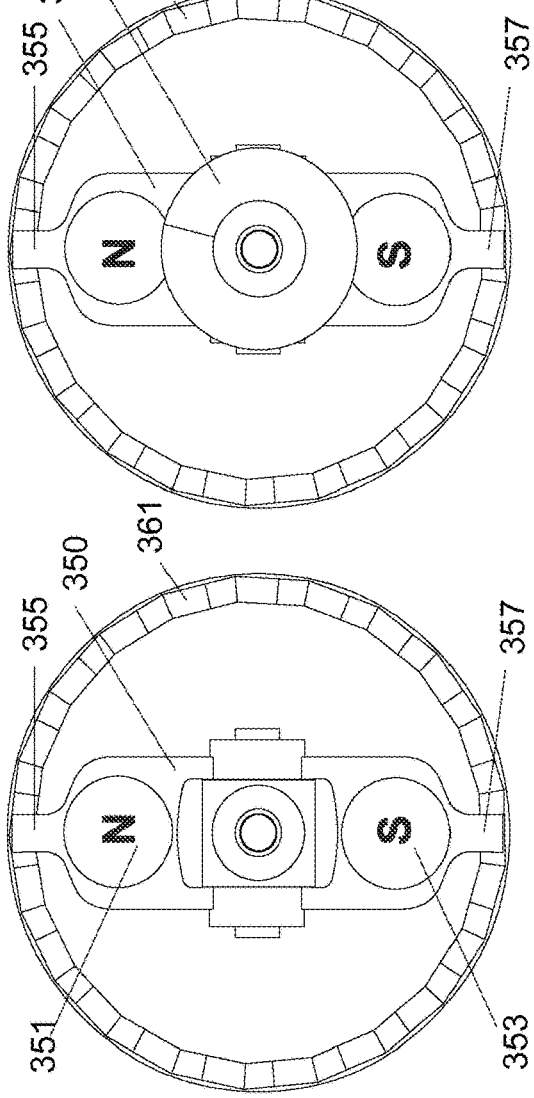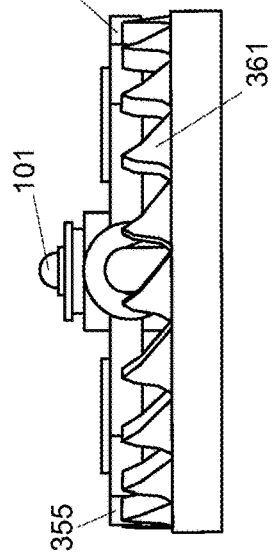

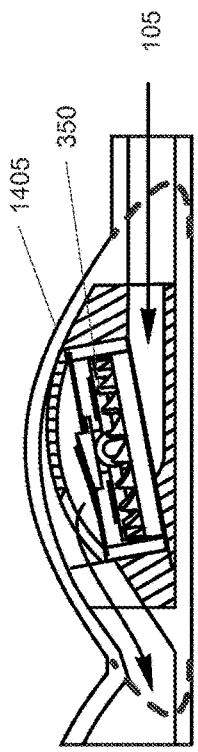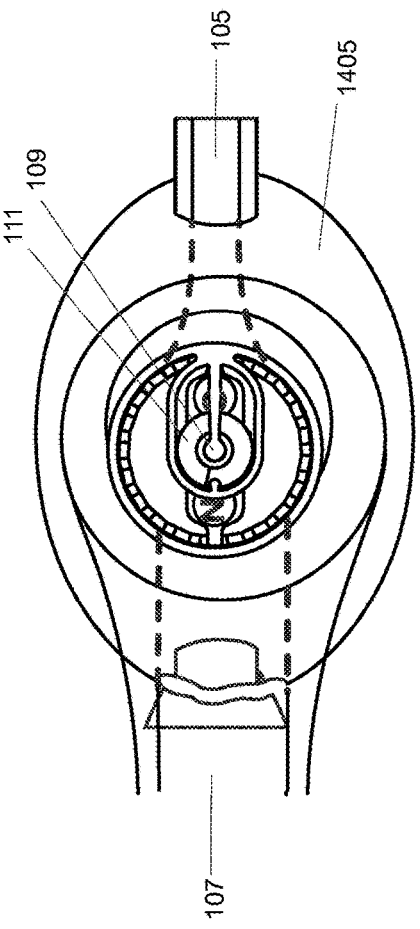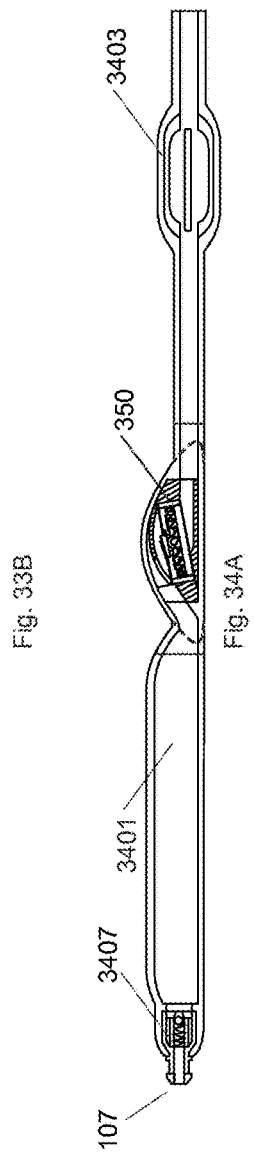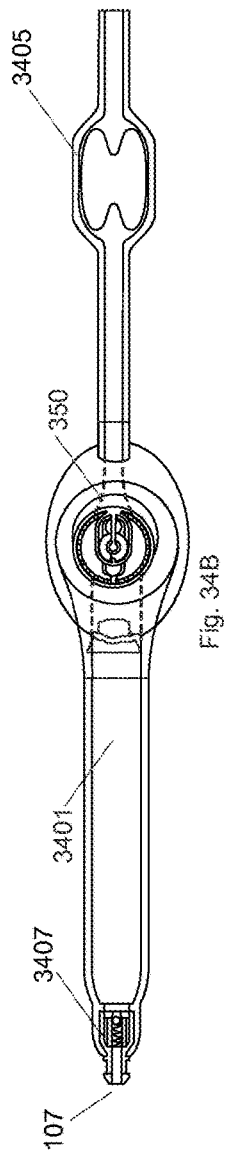

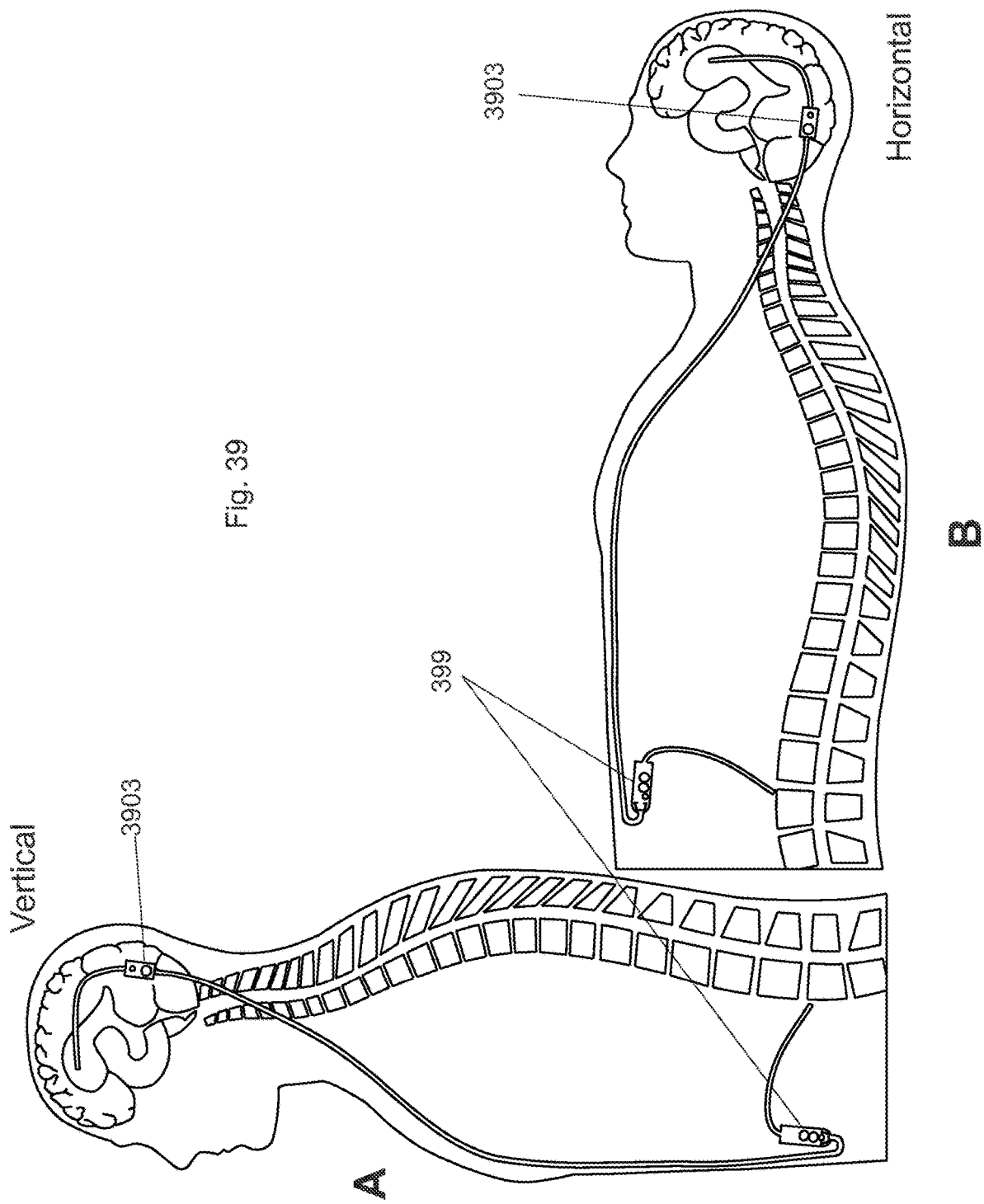

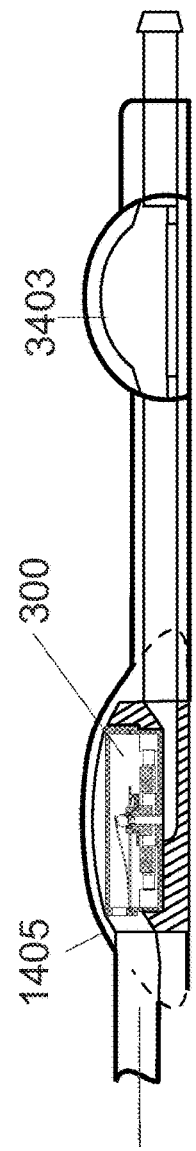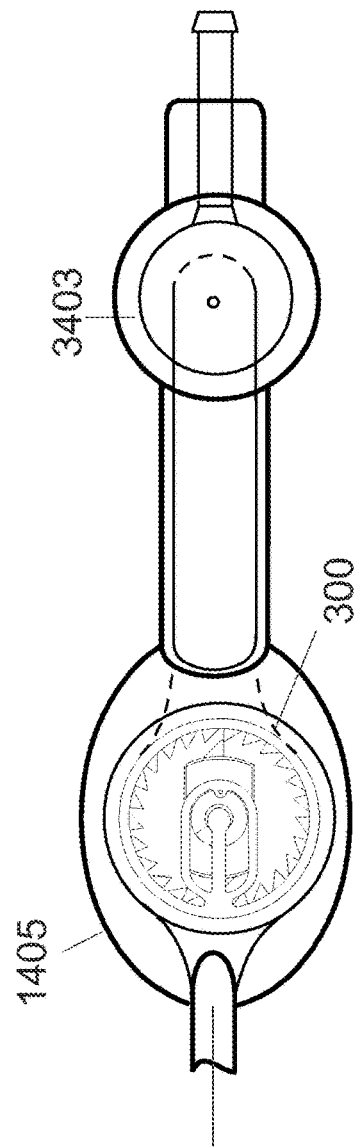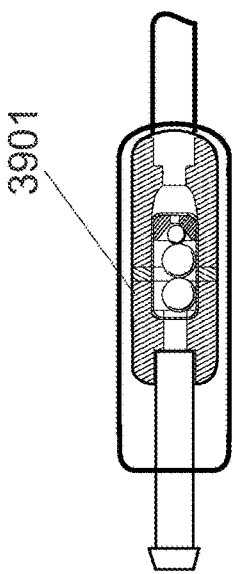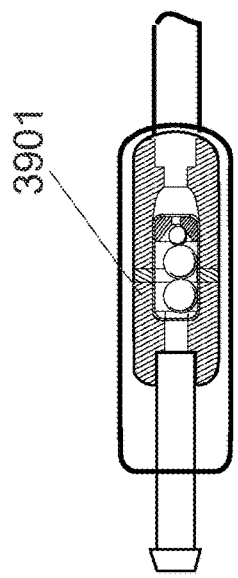
Fig. 40A
Fig. 40B

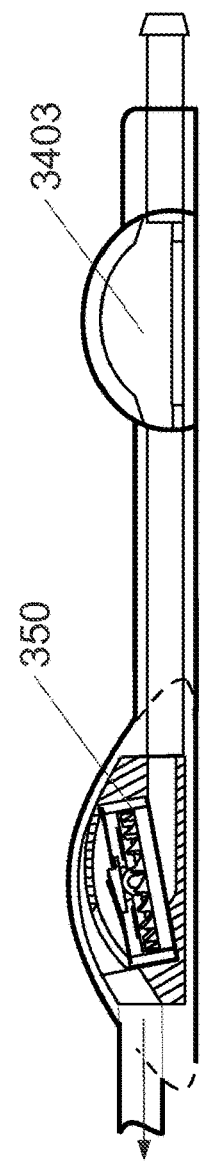
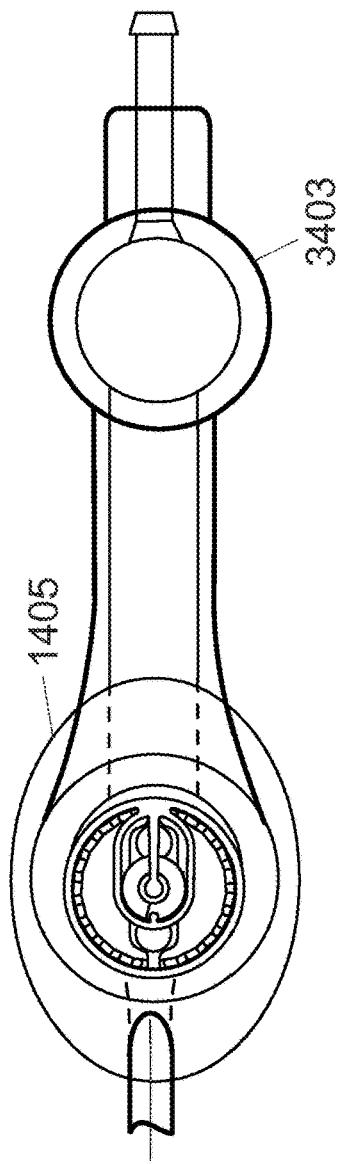
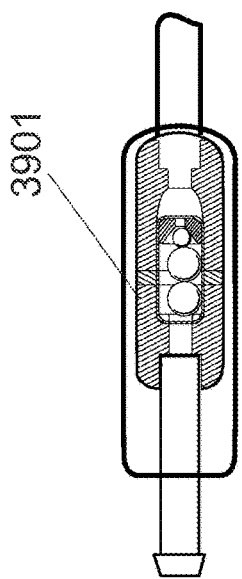
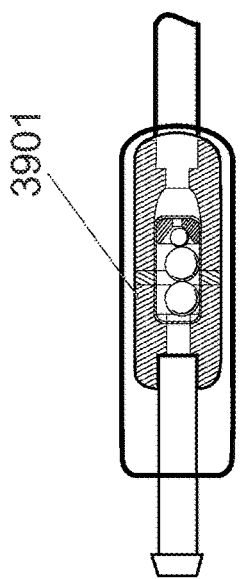
Fig. 41A
Fig. 41B

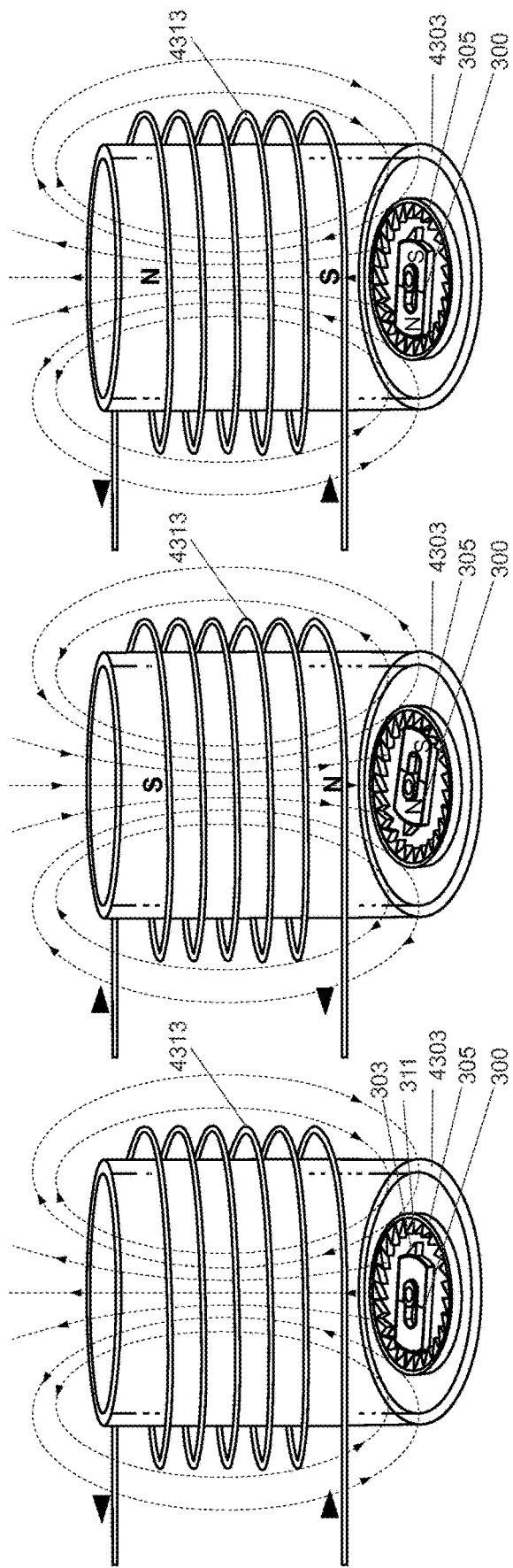

EXTERNALLY PROGRAMMABLE VALVE ASSEMBLY

CROSS-REFERENCE TO RELATED APPLICATIONS

This application claims priority under 35 U.S.C. § 120 to co-pending U.S. application Ser. No. 14/213,480 filed on Mar. 14, 2014, which claims the benefit under 35 U.S.C. § 119(e) of U.S. Provisional Application No. 61/791,922 filed on Mar. 15, 2013, and titled "EXTERNALLY PROGRAMMABLE VALVE ASSEMBLY," each of which is herein incorporated by reference in its entirety.

BACKGROUND

Hydrocephalus is a condition associated with ventricular enlargement caused by net accumulation of fluid in the ventricles of the brain. Non-communicating hydrocephalus is hydrocephalus associated with an obstruction in the ventricular system and is generally characterized by increased cerebrospinal fluid (CSF) pressure. In contrast, communicating hydrocephalus is hydrocephalus associated with obstructive lesions within the subarachnoid space. Normal Pressure Hydrocephalus (NPH), a form of communicating hydrocephalus, primarily occurs in persons over 60 years of age and is characterized by CSF at normal pressure. Classic symptoms of NPH include gait disturbance, incontinence and dementia. In summary, NPH presents as an enlargement of the ventricles with a normal CSF pressure.

The objective in the treatment of hydrocephalus is to reduce the ventricular pressure so that ventricular size returns to a normal level. Hydrocephalus is often treated by implanting into the brain a shunt that drains excess CSF from the ventricles. These shunts are generally comprised of a cerebral catheter inserted through the brain into the ventricle and a one-way valve system that drains fluid from the ventricle into a reservoir of the body, such as the jugular vein or the peritoneal cavity. U.S. Pat. Nos. 3,886,948, 3,288,142 and 4,595,390 describe a shunt that has a spherical sapphire ball biased against a conical valve seat by stainless steel spring. The pressure of the CSF pushes against the sapphire ball and spring in the direction tending to raise the ball from the seat. When the pressure difference across the valve exceeds a so-called "popping" or opening pressure, the ball rises from the seat to allow CSF to flow through the valve and thereby vent CSF. U.S. Pat. No. 4,595,390 describes an externally programmable shunt valve that allows the pressure setting of the valve to be varied by applying a transmitter that emits a magnetic signal over the head of the patient over the location of the implanted shunt. Use of an external programmer with a magnetic transmitter allows the pressure setting of the valve to be adjusted according to the size of the ventricles, the CSF pressure and the treatment objectives.

Although magnetically adjustable shunts allow the pressure of an implanted shunt to be adjusted externally, these art-known shunts are associated with some limitations. For example, when a patient with an implanted magnetically adjustable shunt valve is within proximity of a strong magnet or strong magnetic field, such as a magnetic resonance imaging (MRI) device, the pressure setting of the valve can change. In addition, verification of the pressure setting of art-known magnetic valves can require use of a radiopaque marker on the valve that is detected using an X-ray taken of the location that the valve is implanted.

It would therefore be desirable to design improved ventricular shunts.

SUMMARY OF THE INVENTION

Aspects and embodiments are directed to an externally programmable valve assembly comprising a magnetic rotor that is configured to increase or decrease the pressure setting of the valve in finite increments. The valve assembly may be adapted for implantation into a subject to drain fluid from an organ or body cavity of the subject. In these embodiments, the valve assembly includes an inlet port adapted for fluid connection to one end of a catheter. The second end of the catheter is inserted into the organ or body cavity to be drained of fluid. The valve assembly further includes an outlet port adapted for fluid connection to an end of a drainage catheter. The other end of the drainage catheter can be inserted into a suitable body cavity, such as a vein or the peritoneal cavity, or into a drainage reservoir external to the body, such as a bag. Examples of organs and body cavities that can be drained using the valve assembly of the invention include without limitation the eye, cerebral ventricle, peritoneal cavity, pericardial sac, uterus (in pregnancy) and pleural cavity. In particular, the valve assembly may be adapted for implantation into a subject suffering from hydrocephalus. In this embodiment, the inlet port is adapted for fluid connection to a first end of an intracerebral catheter and the outlet port is adapted for fluid connection to a first end of a drainage catheter. When implanted in the subject, the second end of the intracerebral catheter is inserted in a ventricle of the patient and the second end of the drainage catheter is inserted into a suitable body reservoir of the subject, such as the jugular vein or the peritoneal cavity. Thus, when implanted in the subject, this device provides fluid communication between the ventricle of the subject and the body reservoir of the subject, allowing cerebral spinal fluid to flow from the ventricle through the valve casing to the body reservoir when the intraventricular pressure exceeds the opening pressure of the valve assembly. The subject may suffer from hydrocephalus with increased intracranial pressure, or may suffer from normal pressure hydrocephalus. The removal of CSF from the ventricle reduces the intraventricular pressure.

Further aspects and embodiments are directed to methods of determining the pressure setting of an implanted valve assembly, and adjusting the pressure setting of the valve assembly following implantation into a subject. As discussed in more detail below, according to certain embodiments, adjustment of the pressure setting of the valve may be accomplished via displacement of the magnetic rotor in the valve assembly, resulting in a change in the tension of a spring providing a biasing force against the valve element. The magnetic rotor may be displaced in a side-to-side motion or in an up-and-down (e.g., see-saw) motion within the rotor casing responsive to an applied external magnetic field.

Certain aspects also include a method of decreasing ventricular size in a patient in need thereof, including surgically implanting the valve assembly into the patient, and setting the opening pressure of the valve to a pressure that is less than the ventricular pressure prior to implantation of the valve. Alternatively, the opening pressure of the implanted valve assembly may be set to a pressure that is higher than the ventricular pressure, such that the ventricular size may be increased in a patient in need thereof.

According to one embodiment, a shunt valve assembly comprises a housing, an exterior of the housing being formed of a physiologically compatible material, a rotor casing disposed within the housing, the rotor casing including a plurality of rotor teeth, an inlet port positioned between the rotor casing and an exterior of the housing, the inlet port terminating at its rotor casing end in a valve seat, a spring, a valve element biased against the valve seat by the spring, the valve element and the valve seat together forming an aperture, a magnetic rotor disposed within the housing and including a first and second rotor teeth that are configured to alternately engage the rotor casing teeth responsive to an external magnetic field, thereby causing rotation of the magnetic rotor relative to the rotor casing and producing a selected pressure setting of the shunt valve assembly, and an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port.

In one example, the fluid is cerebrospinal fluid. The rotor casing may have a substantially circular inner surface, and the casing teeth may be positioned around a circumference of the inner surface. In one example, the casing teeth and the first and second rotor teeth are oriented for one-way circular direction of rotation of the magnetic rotor relative to the rotor casing. The magnetic rotor may include a first rotor end and a second rotor end, wherein the first rotor tooth extends from the first rotor end, and the second rotor tooth extends from the second rotor end. In one example, the second rotor tooth is located 180° from the first rotor tooth. In one example, the magnetic rotor is displaced from side-to-side within the rotor casing during the rotation of the magnetic rotor relative to the rotor casing. In another example, the magnetic rotor is displaced up and down relative to the rotor casing during the rotation of the magnetic rotor relative to the rotor casing.

The shunt valve assembly may further comprise a cam which engages the spring and is coupled to the rotor, such that the rotation of the rotor causes rotation of the cam and adjusts a tension of the spring against the valve element. In one example, the cam is a disc cam. In another example, the cam includes an inclined surface, wherein the spring rests against the inclined surface. In one example, the spring is a helical spring. In another example, the spring is a cantilever spring. In one example, the cantilever spring includes an oblong-shaped ring having a fixed end and a free end, the free end of the oblong-shaped ring resting against the cam, and a cantilevered arm that extends from the fixed end of the oblong-shaped ring into an inside of the oblong-shaped ring, and a free end of the cantilevered arm rests against the valve element. In another example, the cantilever spring includes a cantilevered arm and a second arm extending substantially parallel to one another from a fixed point of attachment of the spring, the cantilevered arm having a free end that rests against the valve element. In another example, the cantilever spring includes a cantilevered arm that rests against the valve element and second arm that rests against the cam. In another example, the cantilever spring is a V-shaped spring. In one example, the cam is positioned over the magnetic rotor. In another example, the cam is positioned under the magnetic rotor. In one example, the spring is a curved spring.

In one example of the shunt valve assembly, the valve element is a spherical valve element. The shunt valve assembly may further comprise a pumping chamber coupled between the inlet port and the outlet port. The shunt valve assembly may further comprise a pre-chamber coupled to the inlet port. In one example, shunt valve assembly further comprises a check valve coupled to the output port, the check valve having a check pressure setting that is lower than the selected pressure setting of the valve assembly. In another example, the shunt valve assembly further comprises a cam which engages the spring and is coupled to the rotor, such that the rotation of the rotor causes rotation of the cam and adjusts a tension of the spring against the valve element, and the spring is a cantilever spring including a fulcrum, a first arm attached to the fulcrum and configured to engage the cam, and a cantilevered arm extending from the fulcrum and having a free end configured to rest against the valve element, wherein the fulcrum, the first arm, and the cantilevered arm are configured to provide a lever effect such that a first pressure applied by the cam to the first arm is translated by the cantilever spring into a second pressure applied against the valve element, the second pressure being less than the first pressure.

According to another embodiment, a system comprises an externally programmable implantable shunt valve assembly including a housing, an exterior of the housing being formed of a physiologically compatible material, a rotor casing disposed within the housing, the rotor casing including a plurality of casing teeth arranged around an inner surface of the rotor casing, an inlet port positioned between the rotor casing and an exterior of the housing, the inlet port terminating at its rotor casing end in a valve seat, a cantilever spring, a valve element biased against the valve seat by the cantilever spring, the valve element and the valve seat together forming an aperture, a magnetic rotor disposed within the housing and including a first and second rotor teeth that are configured to alternately engage the casing teeth responsive to pulses of an external magnetic field, thereby causing rotation of the magnetic rotor relative to the rotor casing and producing a selected pressure setting of the shunt valve assembly, and an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port. The system further comprises a non-implantable transmitter head including at least one magnetic coil configured to produce the pulses of the external magnetic field to induce the rotation of the magnetic rotor relative to the rotor casing, and a control device coupled to the transmitter head and configured to provide a signal to the transmitter head to control the transmitter head to produce the pulses of the external magnetic field so as to set the pressure setting of the shunt valve assembly to the selected pressure setting.

In one example, the control device includes a user interface configured to receive an input from the user that selects the selected pressure setting of the shunt valve assembly. In another example, the transmitter head further includes a first magnetic sensor configured to detect a position of the magnetic rotor inside the shunt valve assembly, and the control device further includes a rotor position detector in communication with the first magnetic sensor and configured to determine a pressure setting of the shunt valve assembly based on the position of the magnetic rotor. In another example, the valve assembly further includes a reference marker disposed in a fixed position on or in the housing, the reference marker configured to provide a magnetic reference of a known orientation, wherein the transmitter head further includes a second magnetic sensor configured to measure a position of the reference marker, and wherein the control device further includes a reference detector in communication with the second magnetic sensor and configured to determine the position of the magnetic rotor relative to the position of the reference marker. The first and second magnetic sensors may be Hall sensors, for example.

In one example, the control device is automated such that the transmitter head is programmed by the controller to adjust a number of the pulses of the magnetic field according to the selected pressure setting.

In one example, the system further comprises an implantable gravity-activated valve coupled in series with the externally programmable implantable shunt valve assembly.

In one example, the at least one magnetic coil includes a plurality of magnetic coils arranged spaced apart from one another inside the transmitter head, wherein the control device is coupled to each of the plurality of magnetic coils and configured to control the transmitter head to selectively activate one or more of the plurality of magnetic coils to produce the pulses of the external magnetic field.

In one example, the fluid is cerebrospinal fluid.

In one example, the rotor casing has a substantially circular inner surface, and wherein the casing teeth are positioned around a circumference of the inner surface. The casing teeth and the first and second rotor teeth may be oriented for one-way circular direction of rotation of the magnetic rotor relative to the rotor casing.

In one example, the magnetic rotor is displaced from side-to-side within the rotor casing during the rotation of the magnetic rotor relative to the rotor casing. In another example, the magnetic rotor is displaced up and down relative to the rotor casing during the rotation of the magnetic rotor relative to the rotor casing.

The shunt valve assembly of the system may further comprise a cam which engages the spring and is coupled to the rotor, such that the rotation of the rotor causes rotation of the cam and adjusts a tension of the spring against the valve element. In one example, the cantilever spring includes an oblong-shaped ring having a fixed end and a free end, the free end of the oblong-shaped ring resting against the cam, and a cantilevered arm that extends from the fixed end of the oblong-shaped ring into an inside of the oblong-shaped ring, and a free end of the cantilevered arm rests against the valve element. In another example, the cantilever spring includes a cantilevered arm and a second arm extending substantially parallel to one another from a fixed point of attachment of the spring, the cantilevered arm having a free end that rests against the valve element. In another example, the cantilever spring comprises a fulcrum, a first arm attached to the fulcrum and configured to engage the cam, and a cantilevered arm extending from the fulcrum and having a free end configured to rest against the valve element, wherein the fulcrum, the first arm, and the cantilevered arm are configured to provide a lever effect such that a first pressure applied by the cam to the first arm is translated by the cantilever spring into a second pressure applied against the valve element, the second pressure being less than the first pressure. In another example, the cantilever spring comprises a ring that rests against an underside of the rotor casing, first and second arms extending from an attachment portion of an outer circumference of the ring substantially parallel to one another and terminating in first and second fixed ends, respectively, that are fixed to the underside of the rotor casing, and a cantilevered arm extending from the outer circumference of the ring and terminating in a free end that rests against the valve element, the cantilevered arm being positioned between the first and second arms. In another example, the cantilever spring comprises a central cantilevered arm flanked by two parallel arms, the central cantilevered arm having a free end resting against the valve element, and wherein the two parallel arms are fixed to an underside of the rotor casing.

Another embodiment is directed to a magnetically programmable shunt valve assembly comprising an inlet port configured to receive fluid, an outlet port configured to vent the fluid, a valve positioned between the inlet port and the outlet port and configured to control a flow rate of the fluid from the inlet port to the outlet port through the valve. The valve includes a valve seat coupled to the inlet port, a valve element seated in the valve seat, the valve element and the valve seat together forming an aperture through which the fluid flows, the flow rate of the fluid being controlled by a size of the aperture, a spring configured to bias the valve element against the valve seat and thereby control the size of the aperture, the spring including a first arm and a second arm extending substantially parallel to one another from a fixed point of attachment of the spring, the first arm having a free end that rests against the valve element, a rotor casing having a plurality of rotor teeth positioned around an inner surface of the rotor casing, a magnetic rotor disposed within the rotor casing and having a first rotor tooth and a second rotor tooth disposed approximately opposite the first rotor tooth, wherein the casing teeth are configured to alternately engage said first rotor tooth and said second rotor tooth in response to alternating pulses of an external magnetic field to thereby cause the magnetic rotor to rotate relative to the rotor casing, and a cam coupled to the magnetic rotor and configured to rotate with the magnetic rotor, the cam positioned to engage the second arm of the spring, such that rotation of the magnetic rotor changes a tension of the spring, thereby controlling the size of the aperture and determining a pressure setting of the valve.

According to one aspect, there is provided a method of determining the pressure setting of the shunt valve assembly, wherein the shunt valve assembly is implanted in a patient in need thereof, the method comprising placing a compass exterior to the patient and in proximity to the implanted shunt valve assembly, whereby a needle of the compass aligns with the magnetic rotor thereby indicating the position of the magnetic rotor and the pressure setting of the shunt valve assembly.

According to another aspect, a method of determining the pressure setting of a shunt valve assembly implanted in a patient in need thereof, comprises placing a Hall Sensor exterior to the patient and in proximity to the implanted shunt valve assembly, wherein the Hall Sensor identifies an angle of rotation of the magnetic rotor and thereby determines the pressure setting of the shunt valve assembly.

In another aspect, a method of adjusting a working pressure of a shunt valve assembly implanted in a patient in need thereof, comprises applying an external magnetic field in proximity to the implanted shunt valve assembly and exterior to the patient.

According to one embodiment, a method of decreasing ventricular size in a patient in need thereof comprises implanting in the patient a shunt valve assembly, and setting the selected pressure of the valve assembly to a pressure that is less than a ventricular pressure of the patient prior to implantation of the valve.

According to another embodiment, a method of treating a patient suffering from hydrocephalus comprises implanting in the patient a shunt valve assembly, and setting the selected pressure of the shunt valve assembly to a pressure that is less than a ventricular pressure of the patient prior to implantation of the valve.

In another embodiment, a method of increasing ventricular size in a patient in need thereof comprises implanting in the patient a shunt valve assembly, and setting the selected pressure of the shunt valve assembly to a pressure that is greater than a ventricular pressure of the patient.

Another embodiment is directed to a cantilever spring configured for use in valve assembly that includes a valve element biased against a valve seat by the spring, and a cam coupled to the spring and configured to alter a pressure setting of the valve assembly by adjusting a tension in the spring. The cantilever spring comprises a fulcrum, a first arm attached to the fulcrum and configured to engage the cam, and a cantilevered arm extending from the fulcrum and having a free end configured to rest against the valve element, wherein the fulcrum, the first arm, and the cantilevered arm are configured to provide a lever effect such that a first pressure applied by the cam is translated by the cantilever spring into a second pressure applied against the valve element, the second pressure being less than the first pressure.

In one example of the cantilever spring, the first arm and the cantilevered arm extend substantially parallel to one another from the fulcrum. The cantilevered arm may be longer than the first arm. In one example, the first arm includes an oblong-shaped ring having a fixed end attached to the fulcrum, and a free end configured to rest against the cam, and the cantilevered arm extends from the fixed end of the oblong-shaped ring into an inside of the oblong-shaped ring. In one example, the second pressure is in a range of 0-200 mm $H_2O$.

According to another embodiment, a cantilever spring comprises a fulcrum, a first arm extending from the fulcrum and having a fixed end attached to the fulcrum and a free end, and a cantilevered arm extending from the fulcrum and having a first end attached to the fulcrum, and a free end, wherein the fulcrum, the first arm, and the cantilevered arm are configured to provide a lever effect such that a first pressure applied against the free end of the first arm is translated by the cantilever spring into a second pressure applied by the free end of the cantilevered arm to an object against which the free end of the cantilevered arm rests, the second pressure being less than the first pressure.

In one example of the cantilever spring, the first arm and the cantilevered arm extend substantially parallel to one another from the fulcrum. The cantilevered arm may be longer than the first arm. In one example, the first arm includes an oblong-shaped ring having the fixed end attached to the fulcrum, and the cantilevered arm extends from the fixed end of the oblong-shaped ring into an inside of the oblong-shaped ring. In another example, the cantilever spring further comprises an outer ring attached to the fulcrum and positioned substantially surrounding the oblong-shaped ring. In another example, the first arm and the cantilevered arm are arranged extending from the fulcrum such that the cantilever spring has a V shape. In one example, the second pressure is in a range of 0-200 mm $H_2O$.

According to another embodiment, a cantilever spring comprises a ring, first and second arms extending from an attachment portion of an outer circumference of the ring substantially parallel to one another and terminating in first and second fixed ends, respectively, and a cantilevered arm extending from the outer circumference of the ring and terminating in a free end, wherein the cantilever spring is constructed and arranged such that a first pressure applied against a free portion of the ring positioned substantially opposite the attachment portion is translated by the cantilever spring into a second pressure applied by the free end of the cantilevered arm to an object against which the free end of the cantilevered arm rests, the second pressure being less than the first pressure.

Another aspect is directed to a position control system comprising a magnetically programmable position control device including a housing, a rotor casing disposed within the housing and having a plurality of casing teeth arranged around an inner surface of the rotor casing, a magnetic rotor disposed within the housing and including a first and second rotor teeth that are configured to alternately engage the rotor casing teeth responsive to pulses of an external magnetic field, thereby causing rotation of the magnetic rotor relative to the rotor casing, each pulse of the external magnetic field producing a predetermined increment of rotation of the magnetic rotor relative to the rotor casing. The position control system further comprises a transmitter external to the housing of the magnetically programmable position control device, the transmitter including at least one magnetic coil configured to produce the pulses of the external magnetic field to induce the rotation of the magnetic rotor relative to the rotor casing, and a controller coupled to the transmitter and configured to control the transmitter to produce a selected number of the pulses of the external magnetic field so as to induce a selected amount of rotation of the magnetic rotor.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying drawings in which like reference characters refer to the same parts throughout the different views. For purposes of clarity, not every component may be labeled in every drawing. The drawings are not necessarily to scale, emphasis instead being placed upon illustrating the principles of the invention. The drawings are included to provide illustration and a further understanding of the various aspects and embodiments, and are incorporated in and constitute a part of this specification, but are not intended as a definition of the limits of the invention. In the drawings:

FIGS. 5A-G are diagrams showing the movement of a magnetic rotor within the rotor casing as it is displaced from side-to-side, according to aspects of the invention;

FIGS. 6A-C are diagrams showing an example of a magnetic rotor displaced from side-to-side within the rotor casing in response to a changing magnetic field, according to aspects of the invention;

FIG. 8A is a cross-sectional view of another configuration of a valve assembly including a helical spring biased against the valve element, according to aspects of the invention;

FIG. 8B is a top view of the configuration of FIG. 8A;

FIG. 8C is a bottom view of the configuration of FIG. 8A;

FIG. 9A is a cross-sectional view of another example of a configuration of a valve assembly that includes a magnetic rotor and a helical spring according to aspects of the present invention;

FIG. 9B is a top view of the configuration of FIG. 9A;

FIG. 9C is a bottom view of the configuration of FIG. 9A;

FIGS. 10A and 10B are three-dimensional drawings of another configuration of a valve assembly including a cantilever spring, disc cam and magnetic rotor according to aspects of the invention;

FIGS. 11A and 11B are three-dimensional drawings of another configuration of a valve assembly including a cantilever spring, cam and magnetic rotor according to aspects of the invention;

FIG. 12A is a cross-sectional view of another example of a configuration of a valve assembly including a magnetic rotor and a cantilever spring with two outer arms, the spring being biased against a valve element, according to aspects of the invention;

FIG. 12B is a top view of the configuration of FIG. 12A;

FIG. 12C is a bottom view of the configuration of FIG. 12A;

FIG. 13A is a cross-sectional view of another example of a configuration of a valve assembly including a magnetic rotor and a cantilever spring biased against a valve element, according to aspects of the invention;

FIG. 13B is a top view of the configuration of FIG. 13A;

FIG. 13C is a bottom view of the configuration of FIG. 13A;

FIG. 15A is a top view of the valve assembly of FIG. 14A;

FIG. 15B is another top view of the valve assembly of FIG. 14A;

FIG. 15C is a three-dimensional drawing of the valve assembly of FIG. 14A, showing the valve body forming a sealed enclosure for the valve components, according to aspects of the invention;

FIG. 15D is another three-dimensional drawing of the valve assembly of FIG. 14A;

FIG. 17 is a diagram illustrating increasing pressure applied by the cam of the valve assembly of FIGS. 14A and 14B in response to rotation of the cam, according to aspects of the invention;

FIG. 21 is a three-dimensional drawing of another example of a valve assembly including a magnetic rotor that displaces in a "see-saw" motion, according to aspects of the invention;

FIGS. 23A and 23B are side views of a portion of the valve assembly of FIG. 21, showing alternate displacements of the up and down rotor and one example of a configuration of the biasing spring, according to aspects of the invention;

FIGS. 24A and 24B are side views of a portion of the valve assembly of FIG. 21 showing engagement of the rotor with the casing teeth, with FIG. 24A showing the same rotor position as shown in FIG. 23A, and FIG. 24B showing the same rotor position as shown in FIG. 23B;

FIGS. 27A-E are diagrams showing the interplay between the "front side" rotor tooth and the casing teeth during displacement of the rotor, according to aspects of the invention;

FIGS. 28A-E are diagrams, corresponding to FIGS. 27A-E, showing the interplay between the "back side" rotor tooth and the casing teeth during displacement of the rotor, according to aspects of the invention;

FIG. 30A is a top view of one example of a magnetic rotor that displaces up and down, according to aspects of the invention;

FIG. 30B is a side view corresponding to FIG. 30A;

FIG. 31A is a top view of one example of a magnetic rotor that displaces up and down, according to aspects of the invention;

FIG. 31B is a side view corresponding to FIG. 31A;

FIG. 32A is a top view of one example of a magnetic rotor that displaces up and down, according to aspects of the invention;

FIG. 32B is a side view corresponding to FIG. 32A;

FIG. 33A is a cross-sectional side view of one example of a valve assembly including an up-and-down magnetic rotor within a valve housing, according to aspects of the invention;

FIG. 33B is a top view of the valve assembly of FIG. 33A;

FIG. 34A is a side view of one example of a valve assembly including a valve with an up-and-down magnetic rotor, a pre-chamber, a pumping chamber, and a check valve, according to aspects of the invention;

FIG. 34B is a top view of the valve assembly of FIG. 34A;

FIG. 39 is a schematic diagram illustrating an example of an implanted gravity-activated valve connected in series with a magnetically-programmable valve according to aspects of the invention;

FIG. 40A is a side view of one example of a valve assembly including a gravity-activated valve connected in series with a programmable valve including a side-to-side magnetic rotor, according to aspects of the invention;

FIG. 40B is a top view of the valve assembly of FIG. 40A;

FIG. 41A is a side view of one example of a valve assembly including a gravity-activated valve connected in series with a programmable valve including an up-and-down magnetic rotor, according to aspects of the invention;

FIG. 41B is a top view of the valve assembly of FIG. 41A;

FIGS. 44A-C are diagrams illustrating an example of a magnetic coil included inside the transmitter head of the valve programmer of FIG. 43, according to aspects of the invention;

DETAILED DESCRIPTION OF THE INVENTION

Figure 1:
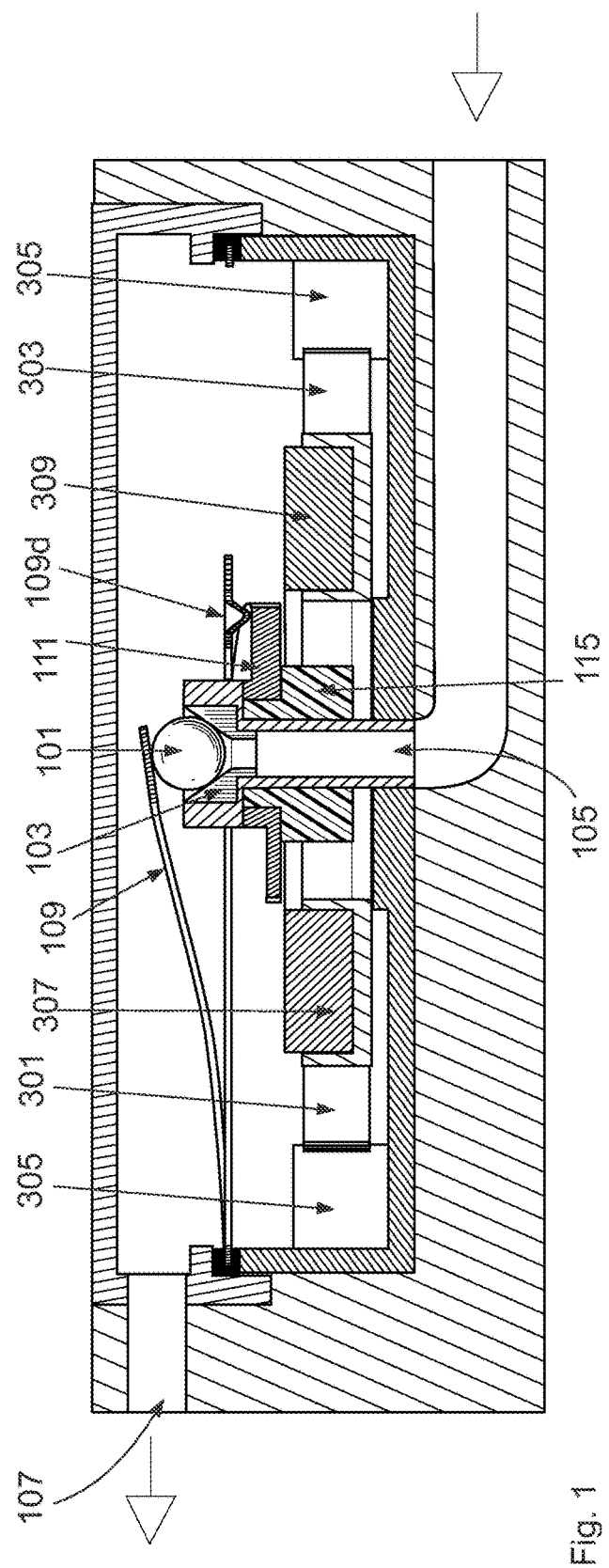
FIG. 1 is a cross-sectional view of one example of a valve assembly according to aspects of the invention.
Figure 2A:
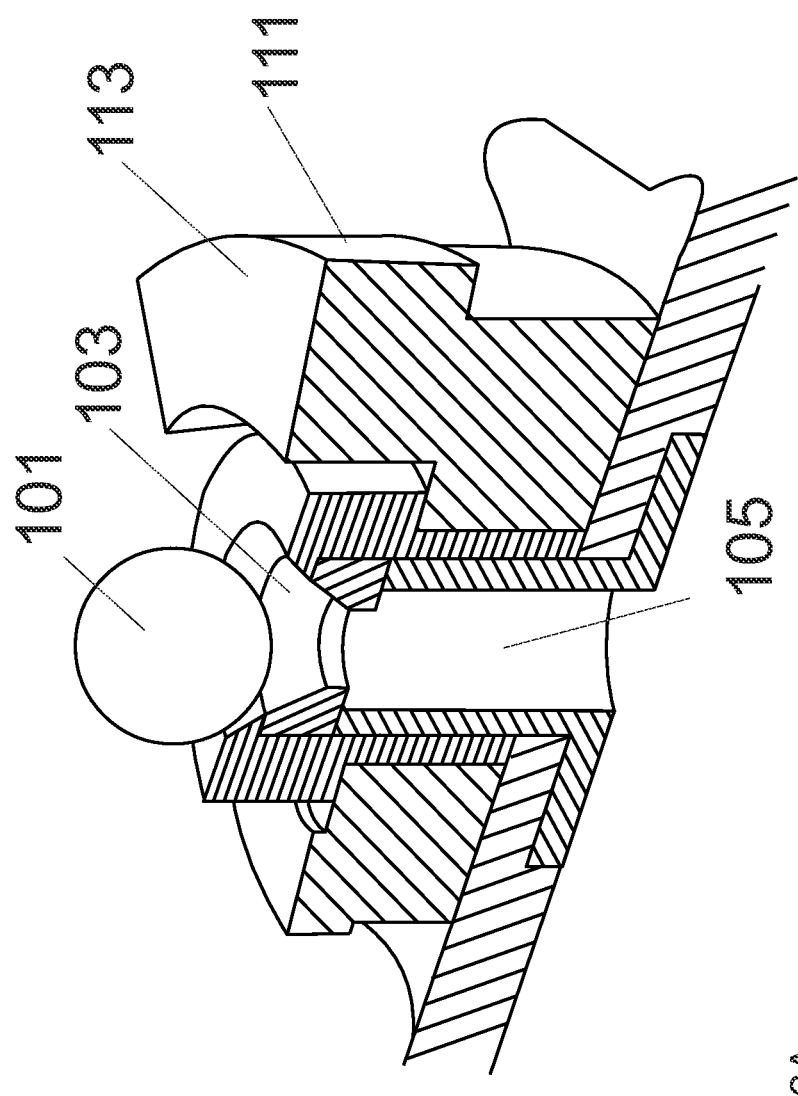
FIGS. 2A-C are enlarged views of portions of the valve assembly depicted in FIG. 1.
Figure 2B:
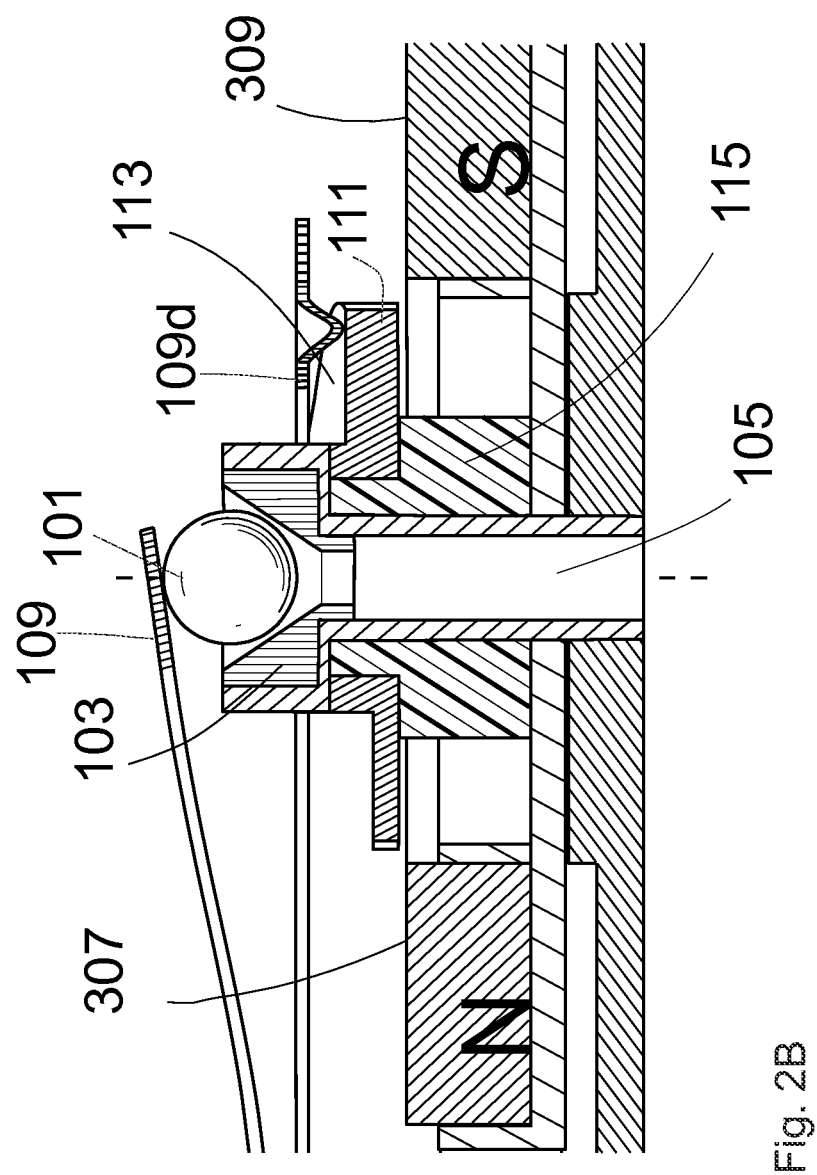
Figure 2C:
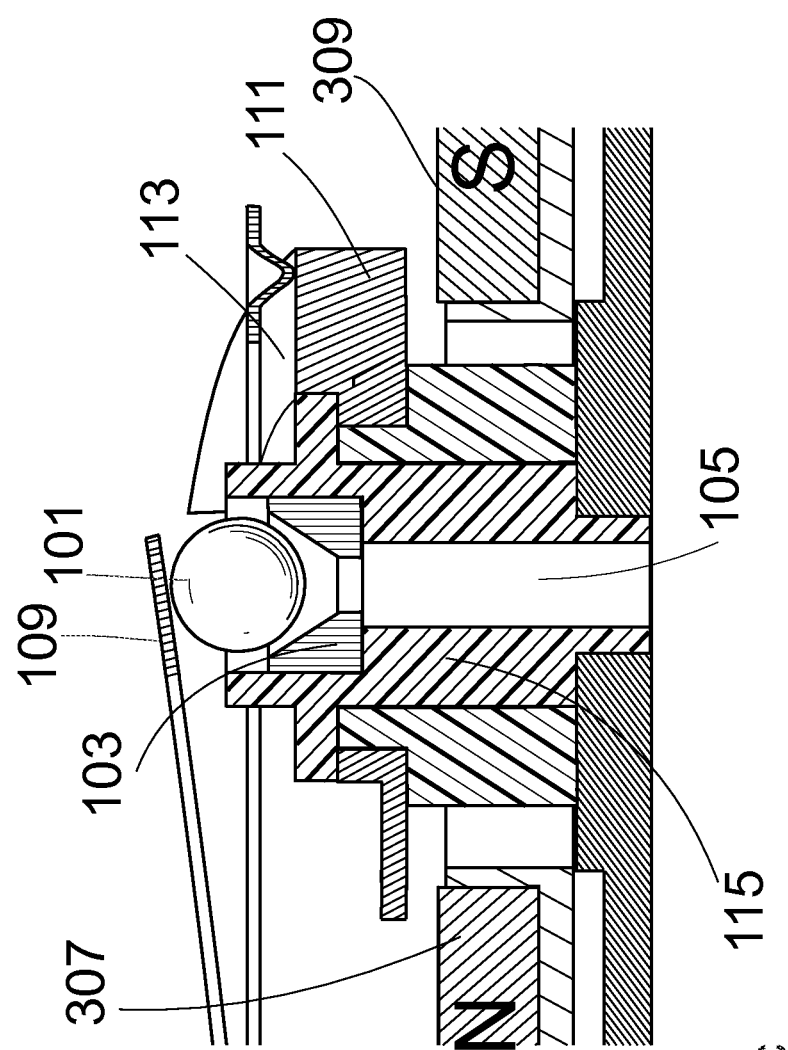

Aspects and embodiments are directed to a valve assembly that incorporates a magnetic rotor configured to increase or decrease the working pressure of the valve in finite increments. As discussed in more detail below, by repositioning the magnetic rotor within a casing of the valve assembly, the opening pressure of the valve element may be adjusted, thereby increasing or decreasing the flow of fluid through the valve assembly. Certain embodiments of the valve assembly are adapted for implantation into a subject suffering from hydrocephalus, and may be used to drain CSF.

Referring to FIGS. 1 and 2A-C, certain configurations of implantable valves, such as CSF valves, for example, include a valve element 101 biased against a valve seat 103 by a spring 109. The pressure of the fluid (e.g. CSF) pushes against the valve element 101 and the spring 109 in the direction tending to raise the valve element 101 from the valve seat 103. The spring 109 may comprise, for example, an extension spring, a compression spring, a helical or coiled spring, a torsional spring, a flat spring, a leaf spring, or a cantilever spring. Certain embodiments of the spring 109 are discussed in more detail below. The valve element 101 can be a sphere, a cone, a cylinder, or other suitable shape. In the example illustrated in FIGS. 1 and 2A-C, the valve element 101 is a spherical ball. The spherical ball and/or the valve seat can be made from any appropriate material including, for example, synthetic ruby or sapphire. The valve seat 103 provides a complementary surface, such as a frustoconical surface for a spherical valve element such that, in a closed position of the valve, seating of the valve element 101 within the valve seat 103, results in a fluid tight seal. The pressure setting, for example, the opening pressure, of such valves is adjusted by altering the biasing force of the valve element 101 against the valve seat 103.

The valve assembly includes an inlet port 105 and an outlet port 107. The inlet port 105 may be connected to a proximal (or inflow) catheter, and the outlet port 107 may be connected to a distal catheter. In the case of a valve assembly that shunts CSF fluid, the proximal catheter may be referred to as a ventricular catheter, and the distal catheter directs fluid to a remote location of the body (such as the right atrium of the heart or the peritoneal cavity) for drainage. Surfaces of the valve element 101 and valve seat 103 together define an aperture, and the size or diameter of the aperture determines the rate and amount of CSF flow through the valve assembly. The valve element 101 preferably has a diameter greater than the valve seat 103 such that when the valve element rests against the valve seat, the aperture is substantially closed. The valve element 101 is placed on the inlet side of the aperture and is biased against the circular periphery of the aperture, keeping it closed until the CSF pressure in the inlet chamber exceeds a preselected popping pressure. The term "popping pressure" refers to the opening pressure of the valve and is generally, a slightly higher pressure than the working pressure. The term "working pressure" can also be referred to as the "operating pressure" and is the pressure of the valve while fluid flows through the valve. The closing pressure is the pressure of the valve at which the flow of fluid through the valve stops. As will be understood by those skilled in the art, given the benefit of this disclosure, the closing pressure is less than the working pressure.

Figure 3B:
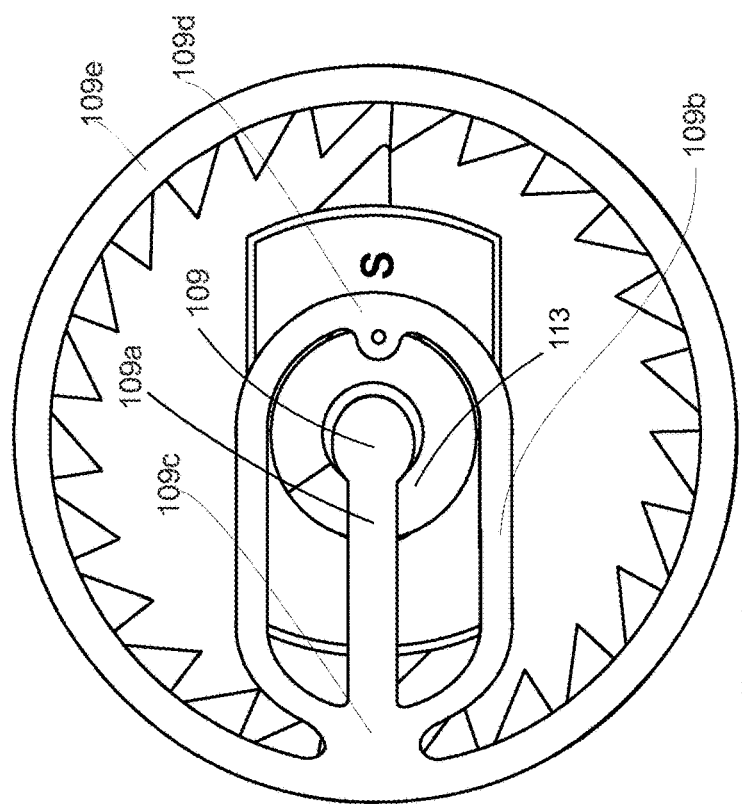
FIG. 3B is a diagram showing a top view of the valve including the magnetic rotor of FIG. 3A, and also showing a spring biased against a ball valve element, according to aspects of the invention.
Figure 3A:
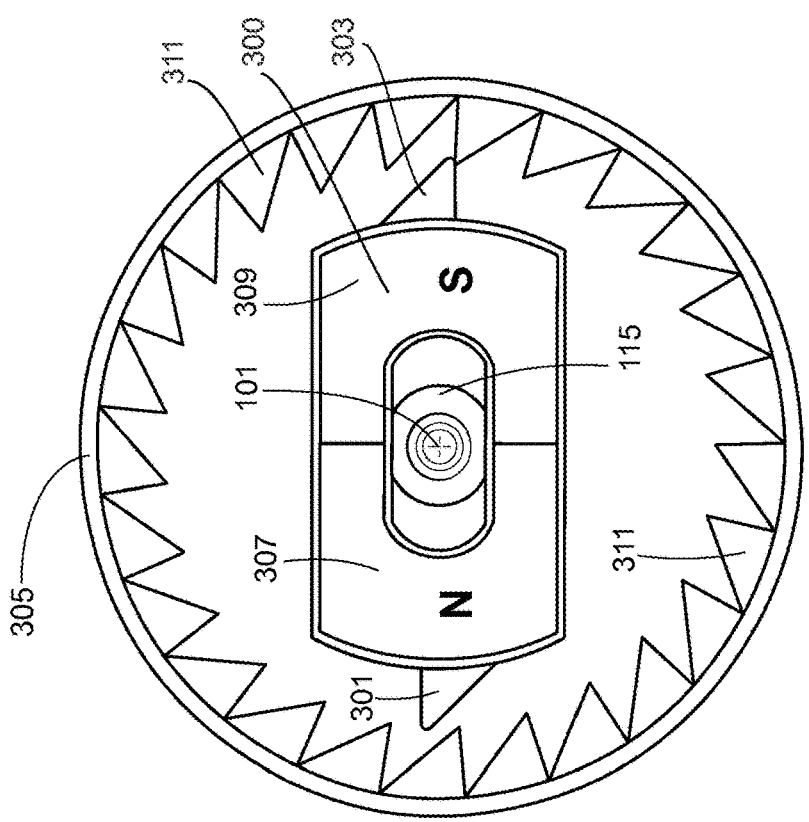
FIG. 3A is a diagram showing a top view of one example of a valve including the magnetic rotor according to aspects of the invention.

According to one embodiment, biasing of the spring 109 against the valve element 101 is achieved using a magnetic rotor that increases or decreases the working pressure of the valve in finite increments. FIGS. 3A and 3B illustrate one example of a magnetic rotor 300 according to certain embodiments. In FIG. 3A, the magnetic rotor 300 is depicted without the spring 109 shown, and in FIG. 3B the magnetic rotor 300 is shown together with the spring 109. As used herein, the term "magnetic rotor" refers to a rotor that comprises at least one magnet. In one embodiment, the magnet or magnets are oriented in such a way that one end of the rotor is attracted to the south pole and repelled by the north pole of an external magnetic field, and the other end of the rotor is attracted to the north pole and repelled by the south pole of an external magnetic field. One of skill in the art will appreciate, given the benefit of this disclosure, that this can be accomplished, for example, by use of a single magnet having north and south poles directed toward opposite ends of the rotor, or two magnets placed at opposite ends of the rotor configured to direct opposite poles toward an external magnetic field.

Referring to FIGS. 1, 2A-C, and 3A-B, in one embodiment, the magnetic rotor 300 is elongated, having first and second rotor ends and comprises a first rotor tooth 301 that extends from the first rotor end, and a second rotor tooth 303 that extends from the second rotor end. In one example, the second rotor tooth 303 is located approximately 180° from the first rotor tooth 301 measured about the rotor's axis of rotation. However, in other examples, other configurations may be implemented, as discussed further below. The magnetic rotor 300 is housed in a rotor casing 305. In the example illustrated in FIGS. 1, 2A-C, and 3A-B, the rotor includes first and second magnet ends 307 and 309, respectively, that are coupled to the first and second rotor teeth 301, 303. In one example, the rotor casing 305 includes a multiplicity of casing teeth 311 positioned within the rotor casing and adapted to alternately engage the first and second rotor teeth 301, 303, as discussed further below. In the illustrated example, the rotor casing 305 is circular and the casing teeth 311 are positioned around the circumference of the rotor casing. However, in other examples, the rotor casing 305 may have other shapes.

In certain embodiments, the projection of the casing teeth 311 is radially inward, toward the rotation axis of the rotor, and the rotor teeth 301, 303 project radially outward or away from the rotor axis. In another embodiment, the projection of the casing teeth 311 is parallel to the rotation axis of the rotor 300, as in the teeth of a crown gear, for example, and the projection of the rotor teeth 301, 303 is along or otherwise aligned with the rotor axis.

Figure 4:
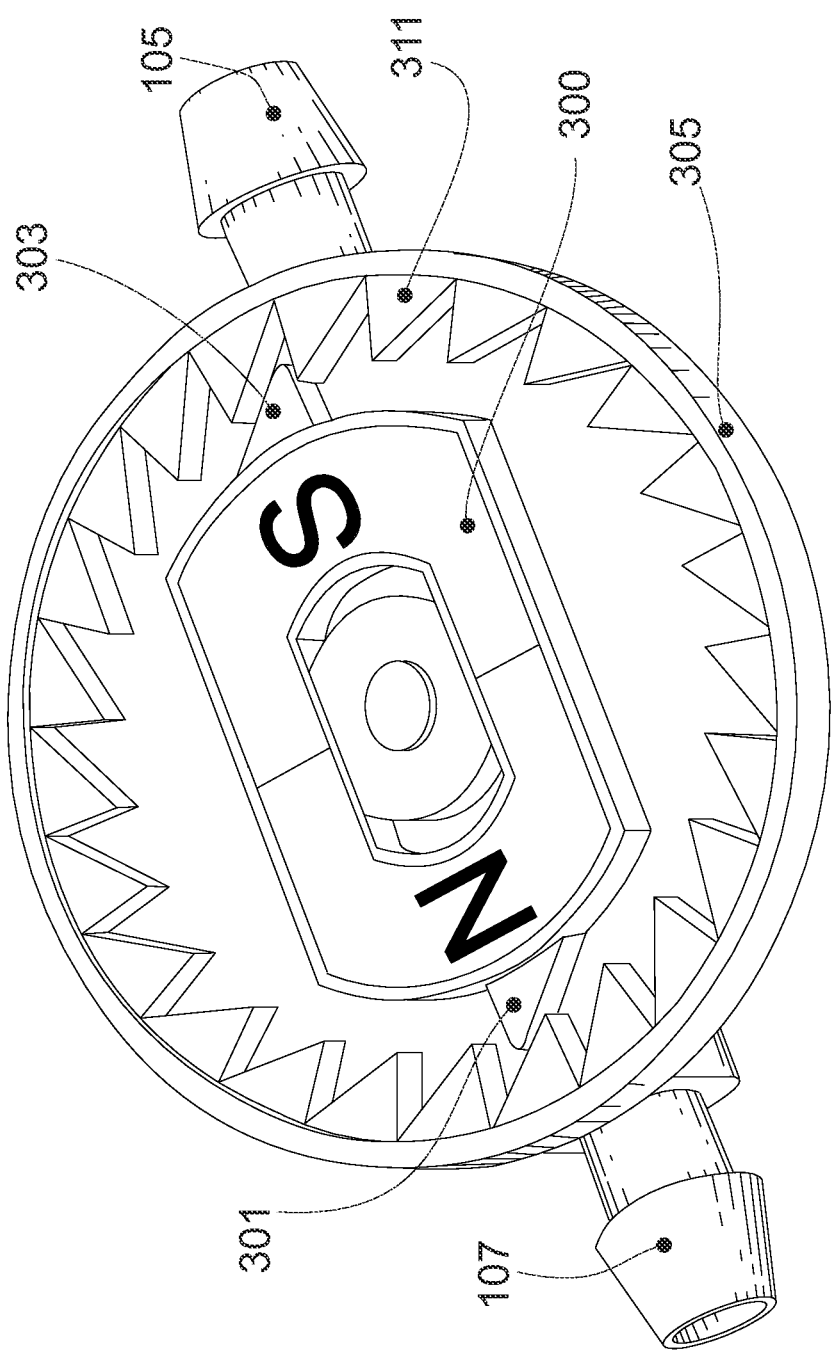
FIG. 4 is a three-dimensional depiction of one example of the magnetic rotor of FIGS. 3A and 3B, according to aspects of the invention.

A perspective view of one example of the magnetic rotor 300 is illustrated in FIG. 4.

According to one embodiment, magnetic pulses from an external magnetic field are used to control movement of the rotor within the rotor casing 305. The external magnetic field may be produced, for example, by a magnetic coil that is placed in proximity to the valve assembly, as discussed in more detail below. In one embodiment, because the casing teeth 311 are positioned in a substantially circular arrangement inside the rotor casing 305, as shown in FIG. 4, for example, the rotor guide 115 causes the rotor 300 to rotate within the rotor casing 305. The rotor 300 may be coupled to a cam or other device that engages the spring 109, such that rotation of the rotor within the rotor casing produces a force that alters the biasing tension of the spring 109 against the valve element 101. In this manner, the size of the aperture formed by the relative positioning of the valve element 101 and the valve seat 103 may be adjusted, thereby controlling the flow rate of fluid through the valve.

Referring to FIGS. 5A-G, as the rotor 300 is displaced in one direction, a leading edge of a leading tooth (first rotor tooth 301 in the illustrated example) engages an angled surface of an opposing casing tooth 311. The continued displacement force of the rotor 300 urges the leading edge of the leading tooth 301 into the angled surface of the opposing casing tooth 311. The outward radial force of the rotor 300 is converted into radial and circumferential components by the angled surface (e.g., an inclined plane) of the opposing casing tooth 311. The circumferential component of the force tends to cause a rotational displacement between the rotor 300 and the rotor casing 305. This continues until the leading rotor tooth 301 has reached its maximal extent, for example, at a notch formed between adjacent casing teeth 311. FIGS. 5A-D illustrate an example of this progression of movement of the rotor 300. As shown in FIGS. 5E-G, a similar result occurs during the next cycle (in response to a subsequent magnetic pulse, for example) in which the opposing rotor tooth 303 becomes the leading tooth.

The shapes of the rotor teeth 301, 303 and casing teeth 311 may be controlled, for example, to result in a ratcheting action, such that relative rotation of the rotor 300 with respect to the rotor casing 305 is always in the same direction for each of the north and south cycles. Examples of teeth shape include, without limitation, triangular, saw tooth and trapezoidal. In one example, the rotor teeth 301 and 303 and the casing teeth 311 can be oriented for one-way direction of movement of the rotor 300 within the rotor casing 305, either in a clockwise direction or in a counter-clockwise direction.

Depending on the orientation of the rotor teeth 301 and 303 and the casing teeth 311, and the interplay between the rotor teeth and casing teeth, the ends of the rotor 300 may be displaced from side-to-side, i.e., radially, within the rotor casing 305, as discussed above and illustrated in FIGS. 5A-G, or may be displaced up and down, i.e., axially, in a "see-saw" motion. FIGS. 3A, 3B and 4 illustrate an example of a magnetic rotor 300 that is displaced side-to-side. Examples of a magnetic rotor that is displaced up-and-down are discussed further below. A magnetic rotor 300 which is displaced side-to-side preferably may include a single magnet with two oppositely polarized ends each directed toward a different end of the rotor. A magnetic rotor which is displaced up-and-down preferably may include two magnets; one disposed at each of the two ends of the rotor, as discussed further below. In such examples, one magnet has its north pole oriented away from the rotor, and is therefore attracted to the south pole of an external magnetic field. The other magnet has its south pole directed away from the rotor, and is therefore attracted to the north pole of an external magnetic field.

The side-to-side or up-and-down motion of the rotor induced by the magnetic impulses results in the alternate engagement of rotor teeth 301 and 303 with the casing teeth 311, resulting in angular displacement of the rotor as discussed above. For example, FIGS. 6A-C illustrate an example of the magnetic rotor 300 displaced from side-to-side within the rotor casing 305, half a casing tooth at time (as shown by the movement of the rotor teeth 301 and 303 relative to the casing tooth 311 marked with a dot) in response to a changing magnetic field. Referring to FIGS. 6A-C, when the applied magnetic field has a south polarity (represented schematically by 601) in proximity to the magnetic rotor 300, the south pole of the rotor is repelled, and the north pole of the rotor is attracted. As a result, the rotor 300 is displaced from one side of the rotor casing 305 to the other side. Similarly, when the applied magnetic field has a north polarity (represented schematically by 603), the north pole of the rotor is repelled and the south pole of the rotor is attracted. As a result, the rotor 300 is displaced in the opposite direction. The rotor 300 displaces from one side of the rotor casing 305 to the other side of the rotor casing in response to each change in the polarity of the applied magnetic field. As the rotor 300 is displaced, it is guided by the casing teeth 311 arranged on the inner surface of the rotor casing 305.

For the example of the magnetic rotor 300 illustrated in FIGS. 4-6C, the casing teeth 311 and the rotor teeth 301, 303 are configured such that the rotor 300 will only rotate in a clockwise direction in increments of one half of a casing tooth per magnetic pulse. A pair of pulses of opposite polarity (e.g., north followed by south, or vice versa), will cause the rotor 300 to rotate by one casing tooth 311. As will be appreciated by those skilled in the art, given the benefit of this disclosure, the rotor teeth 301, 303 and the casing teeth 311 may alternatively be configured such that the rotor 300 rotates only in a counter-clockwise direction. Additionally, the increment of rotation (e.g., number of degrees) of the rotor 300 in response to each magnetic impulse can be varied by changing the number of casing teeth 311. In at least some embodiments, at least one rotor tooth 301, 303 always engages at least one casing tooth 311, regardless of a position of the rotor 300 during its cycling. Accordingly, the rotor will not rotate by more than one tooth for each cycle. Such safety features prevent excessive rotations as might otherwise be experienced in the presence of an unintentional magnetic field.

As discussed above, the valve assembly operated by a magnetic rotor according to certain embodiments includes the spring 109 for biasing the valve element 101 against the valve seat 103. Fluid enters the inlet port 105 and pushes against the valve element 101 which rests on the valve seat 103. The valve seat 103 and valve element 101 can, for example, be made from synthetic ruby or sapphire. The valve assembly is configured such that rotation of the rotor within the rotor casing controls the spring 109 to adjust the biasing of the valve element 101 against the valve seat 103, thereby adjusting the size of the aperture and controlling the flow of fluid through the valve. In one embodiment, the valve assembly further includes a cam 111 which engages the spring 109. The cam 111 may be coupled to the magnetic rotor 300 and in contact with the spring 109 such that displacement of the rotor 300 causes movement of the cam 111 which, in turn, adjusts the tension of the spring 109 against the valve element 101. In particular, the rotor 300 may include a rotor guide 115 that rotates as the rotor rotates, causing the cam 111 to move in a circular motion and change the tension of the spring 109. In one example, rotation of the rotor 300 in a clockwise direction causes the cam 111 to also rotate in a clockwise direction.

In some embodiments, the cam 111 indirectly or directly produces vertical displacement of the spring 109. The cam 111 may, for example, have a helically inclined surface 113 that is in contact with spring 109. In certain examples, the cam 111 is circular in shape with an inclined surface 113 that gradually inclines from a lowest position. As will be appreciated by one of skill in the art, given the benefit of this disclosure, a cam 111 with an inclined surface 113 can include a cam with a surface that gradually inclines or that inclines in discrete steps. As the rotor 300 rotates, the cam with the inclined surface 113 also rotates and changes the tension of the spring 109 by changing the level of incline of the cam 111 against the spring 109. Such a cam 111 with the inclined surface 113 can be described as producing a vertical displacement of the spring 109.

For certain applications of the valve assembly, such as the treatment of hydrocephalus, for example, the pressure range of the valve may be approximately 0-200 mm $H_2O$ or 0-400 mm $H_2O$, for example, which are very low pressure ranges. Furthermore, it may be desirable to make small pressure changes within the range. However, it may not be practicable (due to manufacturing constraints, etc.) to produce a valve assembly in which the cam 111 is capable of making very minute movements, for example, on the order of a few micrometers. Therefore, in order to accommodate the low pressure range and small incremental changes in pressure, a very soft spring 109 may be required. Conventionally, in order to obtain a sufficiently soft spring, the spring would be very long. However, accommodating a very long, soft spring inside an implantable housing may pose challenges. Accordingly, aspects and embodiments are directed to spring configurations that produce a lever or "gear reduction" effect, such that reasonable (i.e., within standard manufacturing capabilities) movements of the cam 111 may be translated into very small adjustments in low pressure settings. In particular, certain embodiments include a cantilever spring configuration, in which the spring 109 includes an element (or arm) that is in direct or indirect contact with the cam 111, and another element (or arm, referred to as the cantilevered arm) that is biased against the valve element 101. Rotation of the cam 111 causes pressure against the spring element in contact with the cam, and that pressure is spread and reduced through the spring structure, such that resulting pressure applied against the valve element 101 by the cantilevered arm is in the desired range (e.g., 0-200 mm $H_2O$, as mentioned above).

Figure 7A:
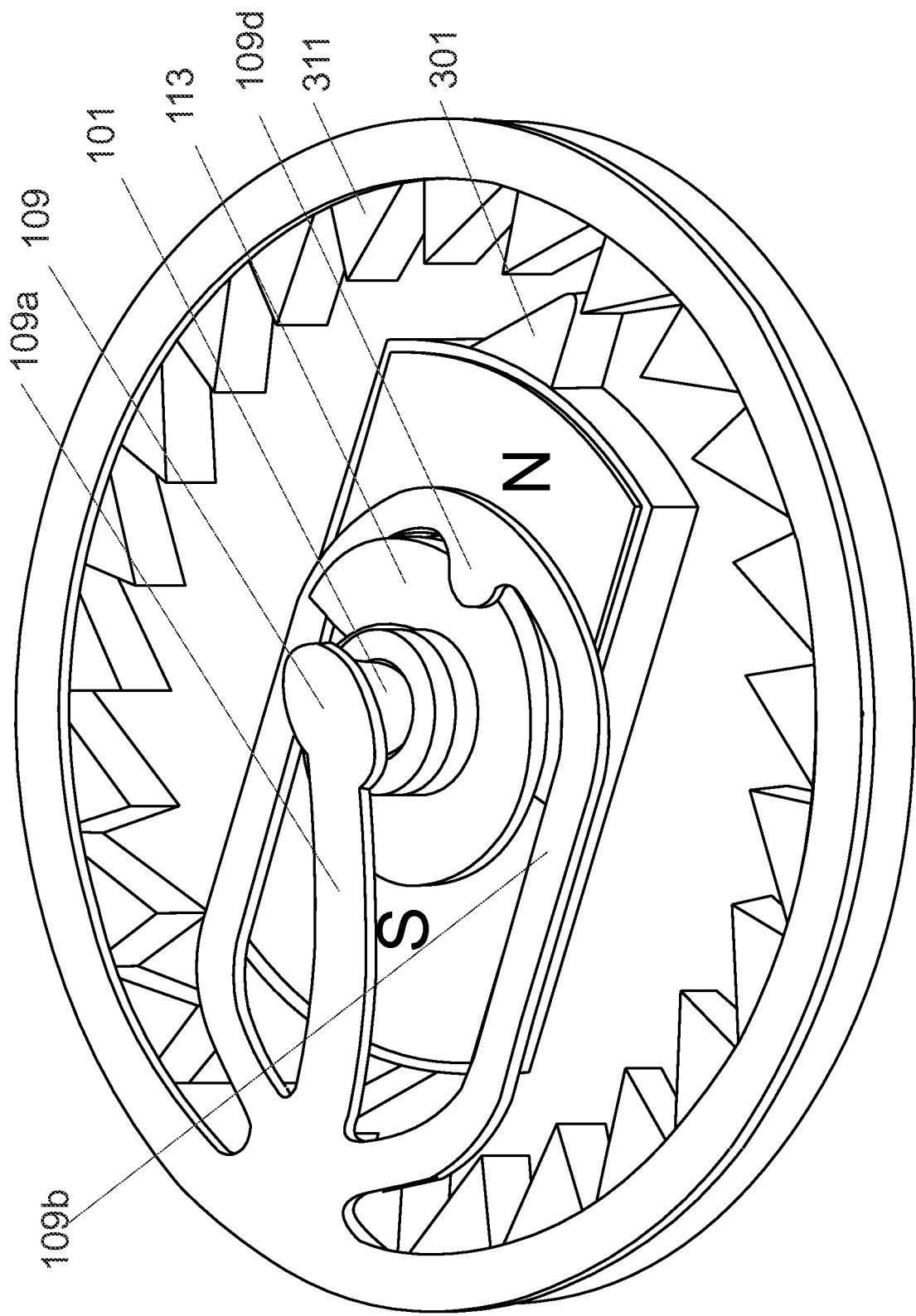
FIG. 7A is a three-dimensional rendering of one example of the valve assembly including the magnetic rotor according to aspects of the invention.
Figure 7B:
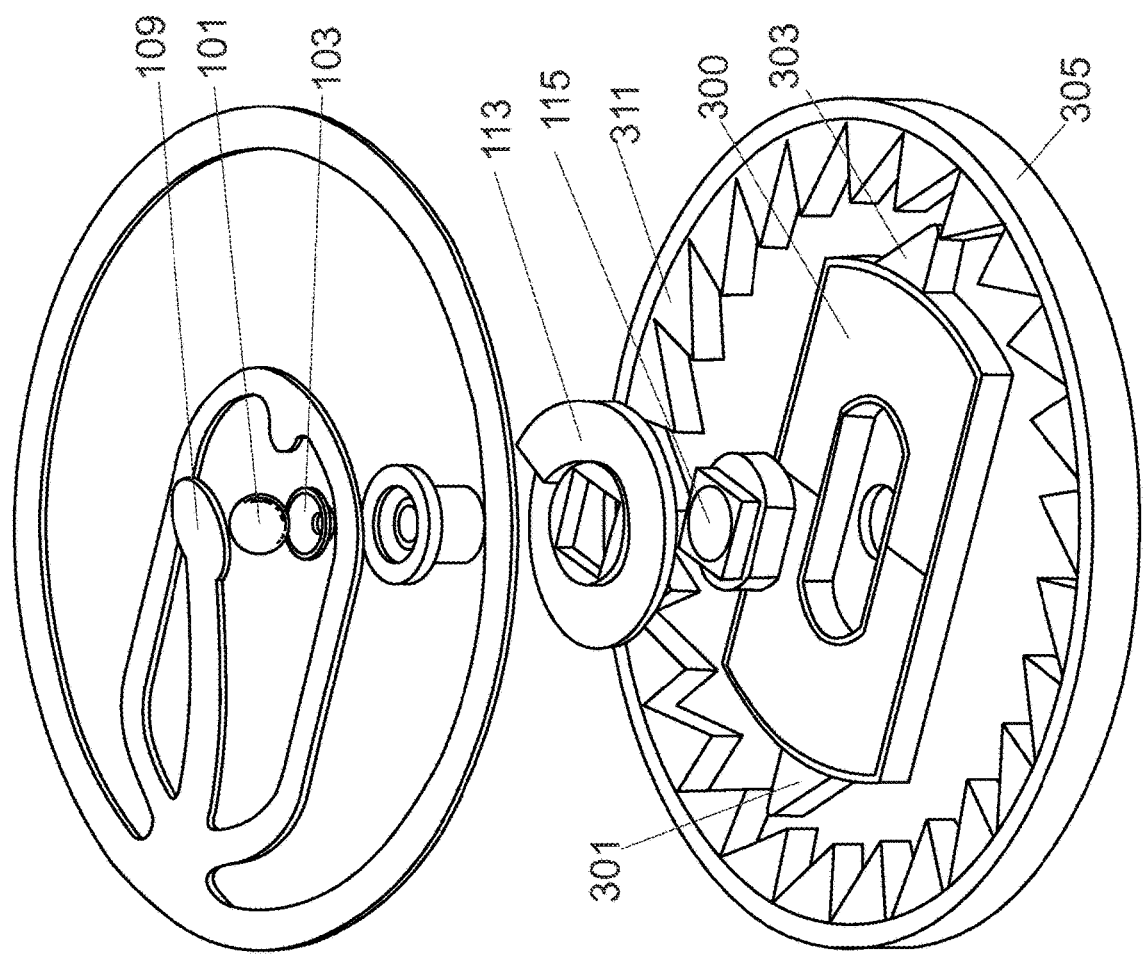
FIG. 7B is an exploded view of the components of FIG. 7A.

Referring to FIGS. 3B, 7A, and 7B, there is illustrated one example of a cantilevered spring 109. FIG. 7A is a three-dimensional view of the configuration of the spring 109 and cam 111 depicted in FIGS. 3A and 3B. FIG. 7B is an exploded view of the configuration of FIG. 7A. In this example, the cantilevered arm 109a has a free end that is biased against the valve element 101. The cantilevered arm 109a extends from (or is attached to, for example, welded to) an oblong-shaped ring 109b, which includes a fixed end 109c and a free end 109d. In one example, the free end 109d is about 180° from the fixed end 109c, and the free end 109d rests against the cam 111. The fixed end 109c of the oblong shaped ring 109b is, in turn, fixed to an outer ring 109e that rests on top of the periphery of the rotor casing 305. In this example, the cam 111 has an inclined surface 113 that produces vertical displacement of the spring 109. In one embodiment, when the free end 109d of the spring 109 is resting against the cam 111 at its lowest level of incline or its lowest position, the pressure setting of the valve will be highest. Conversely, when the free end 109d of the spring 109 is resting against the cam 111 at the highest position of the cam (tending to push the cantilevered arm 109a up, or in other words, in a direction opposite to the valve seat 103, the pressure setting of the valve will be the lowest. In FIG. 7A, the free end 109d of the oblong-shaped ring 109c is shown resting on the cam 111 at a position close to the highest level of incline. As can be seen in FIG. 7A, in this position, the cantilevered arm 109a of the spring 109 is pushed away from the valve seat 103. As discussed above, with this configuration, the pressure exerted by the cam 111 against the free end 109d of the spring 109 is transferred through the oblong-shaped ring 109b, and the fulcrum of the cantilevered spring (in this case, the fixed end 109c) to the cantilevered arm 109a, such that the pressure applied by the free end of the cantilevered arm 109a against the valve element 101 is greatly reduced compared to what the pressure would be if the leaf of the spring in contact with the cam 111 were in direct contact with the valve element.

In other embodiments, the cam 111 indirectly or directly produces horizontal displacement of the spring 109. For example, the cam 111 may be a disc cam which produces horizontal, e.g., radial, displacement of the spring 109 by changing the tension of the spring as the cam rotates. An example of a valve assembly including cam configured to produce horizontal (e.g., radial) displacement of the spring 109 is illustrated in FIG. 8A. FIG. 8B is a top view of the configuration of FIG. 8A, and FIG. 8C is a bottom view of the configuration of FIG. 8A. In this embodiment, the cam 111 is a disc cam 801 and the spring 109 is a helical spring 803. The disc cam 801 may cause horizontal (e.g., radial) displacement of a follower 805 which is in contact with a helical spring 803. As used herein, the term "follower" refers to an element that is in physical contact with both the cam and the spring and that is displaced as the cam rotates.

Referring to FIGS. 8A-C, fluid enters the inlet port 105 at the side of the valve and pushes the valve element 101 in a direction perpendicular to a central rotational axis 807 of the rotor indicated by the dashed line. The direction of fluid flow is indicated by the arrows on the right and left sides of the figures. The rotor 300, including the first and second magnet ends 307 and 309, rotor teeth 301 and 303, and casing teeth 311 are as shown. Rotation of the rotor 300 causes the disc cam 801 also to rotate. The disc cam 801 is in contact with the follower 805 which, in turn, is in contact with the helical spring 803. Accordingly, rotation of the disc cam 801 causes horizontal (e.g., radial) displacement of the follower 805, which, in turn, increases or decreases the tension of the helical spring 803 with which it is in contact. The disc cam 801 is shaped such that as the cam 801 rotates, the distance between the center of the cam 801 and the point of contact with the follower 805 increases or decreases gradually, which in turn, causes a change in the tension of the helical spring 803. When the tension in the helical spring 803 is the greatest, the pressure setting of the valve will be at its highest. When the tension in the helical spring 803 is the lowest, the pressure setting of the valve will be the lowest. As shown in FIGS. 8A-C, when the distance between the center of the disc cam 801 and the outer periphery of the disc cam in contact with the follower 805 is the greatest, the tension of the helical spring 803 is the greatest and will tend to push the valve element 101 against the valve seat 103. Similar to the cantilever arrangement discussed above, with a helical spring configuration, the pressure from the cam 801 is translated and decreased through the body of the helical spring 803 to the end of the spring rests against the valve element 101.

In another embodiment, the disc cam 801 may be in direct physical contact with the helical spring 803. The disc cam 801 may be configured to produce horizontal displacement of the helical spring 803 as the disc cam 801 rotates.

FIGS. 9A-C illustrate another configuration of a valve assembly including a magnetic rotor that displaces from side-to-side. In this example, the spring is a helical spring 803. FIG. 9A is a cross-sectional view of the valve assembly. FIG. 9B is a top view of the valve assembly of FIG. 9A, and FIG. 9C is a bottom view of the valve assembly of FIG. 9A. Fluid enters the inlet port 105 at the side of the valve. In this configuration, shortening or lengthening of the helical spring 803 produces a change in the pressure setting of the valve. For example, as the helical spring 803 rotates in a clockwise direction, the spring lengthens, thus decreasing the pressure of the spring against the valve element 101 and decreasing the pressure setting of the valve. Conversely, as the helical spring 803 rotates in a counter-clockwise direction, the spring shortens, thus increasing the pressure of the spring against the valve element 101 and increasing the pressure setting of the valve. Those skilled in the art will appreciate, given the benefit of this disclosure, that the helical spring 803 may alternatively be configured such that clockwise rotation increases the pressure setting of the valve and counter-clockwise rotation decreases the pressure setting of the valve.

In another example, a disc cam 801 may be configured to cause horizontal (e.g., radial) displacement of a cantilever spring 109 comprising two arms, such as a V-shaped spring, for example. FIGS. 10A and 10B illustrate such an example of a valve configuration with a side-to-side magnetic rotor 300 and a disc cam 801, wherein the spring 109 is a V-shaped spring 1001. One arm of the V-shaped spring 1001 is in physical contact with the disc cam 801 (resting against the disc cam 801), and the other arm is biased against the valve element 101. The disc cam 801 may be similar to that of FIGS. 8A-C in that the disc cam 801 is shaped such that as the cam rotates, the distance between the center of the cam and the point of contact with the V-shaped spring 1001 increases or decreases gradually causing a change in the tension of the spring. Thus, rotation of the rotor 300 causes the cam 801 to rotate, which increases or decreases tension in the V-shaped spring 1001. When the tension in the spring 1001 is the highest, the pressure setting of the valve will also be at its highest. Similar to the arrangements discussed above, with the V-shaped spring configuration, the pressure from the cam 801 is translated through the fulcrum of the spring (point of the V) from the arm in contact with the cam to the arm in contact with the valve element. By selecting the relative length of the two arms and position of the fulcrum, the range of pressure applied against the valve element 101 may be controlled to be within a desired range, as discussed above.

FIGS. 11A and 11B illustrate another valve configuration similar to that shown in FIGS. 10A and 10B. In this example, the spring 109 includes a curved spring 1101 which has two arms to provide the cantilevered effect discussed above. One arm of the spring 1101 rests against the disc cam 801, and the other arm of the spring rests against the valve element 101. In this embodiment, similar to the embodiments discussed above, rotation of the rotor 300 causes rotation of the disc cam 801, which changes the tension of the spring 1101 and thereby adjusts the pressure setting of the valve.

FIGS. 12A-C illustrate another configuration of a valve assembly including a magnetic rotor 300 according to certain embodiments. In this example, fluid enters the inlet port 105 at the side of the housing and the casing end of the inlet port is parallel to the central rotational axis 807 of the rotor (as depicted by the dashed line). The cam 111 is positioned under the rotor 300 and rotation of the rotor causes the cam also to rotate, as described above. Rotation of the cam 111 again increases or decreases tension of the spring 109. In the example illustrated in FIGS. 12A-C, the spring 109 is a cantilever spring, and includes a ring 109f with three arms extending from the outside of the ring. The ring 109f rests against the underside of the rotor casing 305. A central arm 109g extending from the outside of the ring 109f is a cantilevered arm with its free end resting against the valve element 101. The other arms 109i extending from the ring 109f are fixed to the underside of the rotor casing 305, but are able to pivot. As shown in FIGS. 12A-C, when the cam 111 is at its highest position, the tension in the spring 109 is the greatest and tends to push the cantilevered arm 109g in the direction against the valve seat 103, thus increasing the pressure setting of the valve.

FIGS. 13A-C show a valve configuration similar to that of FIGS. 12A-C, wherein the cam 111 has an inclined surface 113 and the spring 109 includes a central arm 109j flanked by two parallel arms 109k. The central arm 109j is a cantilevered arm with a free end resting against the valve element 101, and the two parallel arms 109k are fixed to the underside of the rotor casing 305. For the springs shown in FIGS. 12A-C and 13A-C, the relationship between the position of the cam 111 and the tension of the spring 109 is dependent on the location of a pivoting point 1301, the point of the contact between the spring 109 and the cam 111, and the point of contact between the cantilevered arm 109g and the valve element 101. Depending on these relationships, when the cam 111 is at its highest position, the cantilevered arm 109g can be pushed toward the valve element 101, or alternatively, the cantilevered arm 109g can be pushed away from the valve element 101. In the configuration depicted in FIGS. 13A-C, when the cam 111 is at its highest position (or its highest level of incline) against the spring 109, the tension of the spring 109 is the greatest and tends to push the cantilevered arm 109g in the direction toward the valve element 101. However, if the pivoting point 1301 of the cantilevered arm 109g were closer to the valve element 101, when the cam 111 is at its highest level of incline, the spring 109 would be pushed in a direction away from the valve element 101.

Referring to FIGS. 14A, 14B, and 15A-D, there is illustrated another example of an implantable valve assembly including a magnetic rotor according to certain embodiments. In this example, the magnetic rotor 300 is again coupled to the cam 111. The biasing spring 109 includes a cantilevered arm 109a having a fixed end at a fulcrum 1401 (or fixed attachment point of the spring) and a free end that rests against the valve element 101. The rotor guide 115 guides rotation of the rotor 300 about its rotation axis 807. The valve assembly includes a valve body 1405 (also referred to as a housing) that houses the components of the valve. The valve body 1405 may include a bottom cap 1407 and a top cap 1409 that mates with the bottom cap to form a sealed enclosure that is suitable for implantation into the human body. The valve body 1405 may be made from any physiologically compatible material. Non-limiting examples of physiologically compatible materials include polyethersulfone and silicone.

Figure 14A:
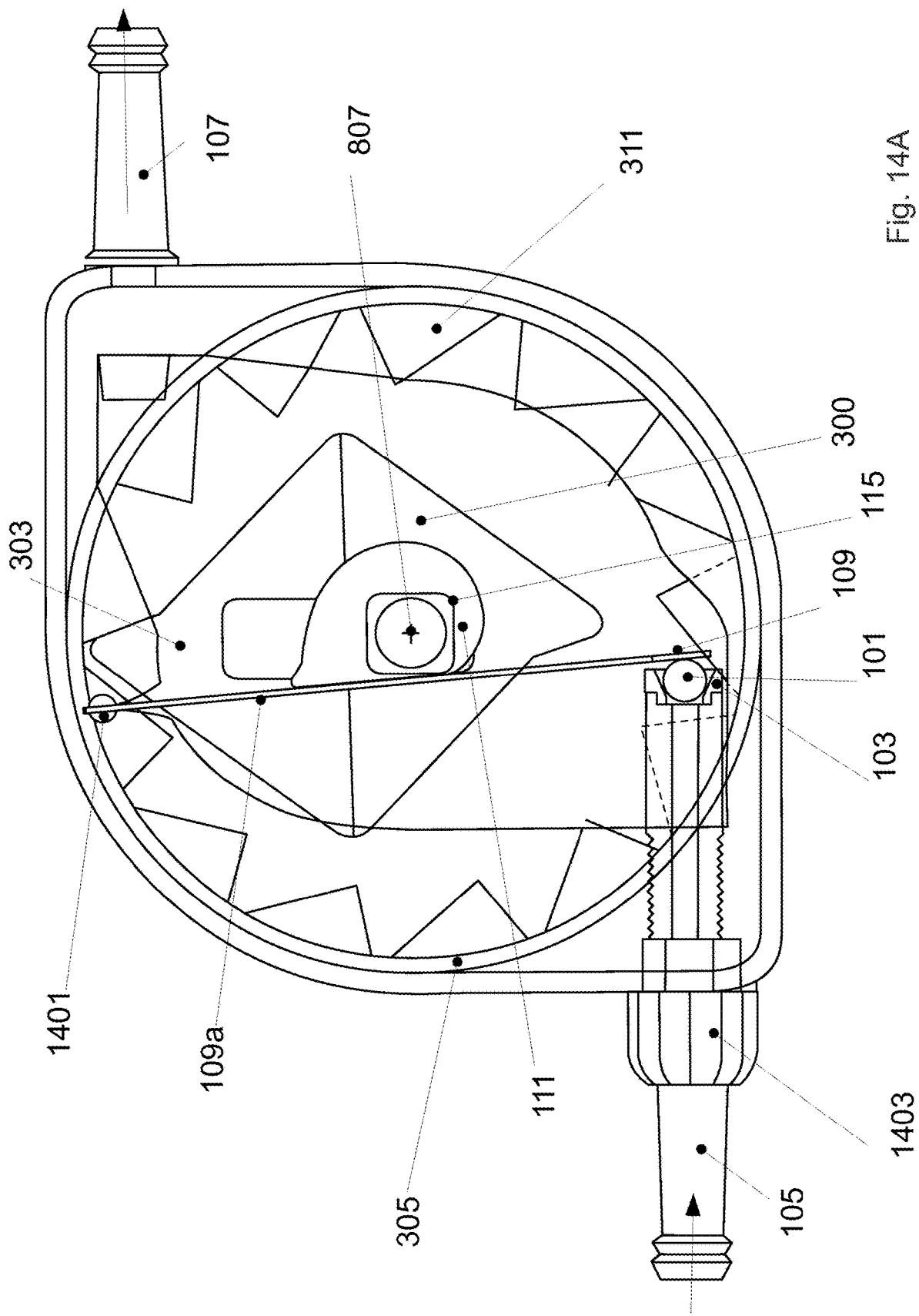
FIG. 14A is a plan view of another example of a valve assembly according to aspects of the invention.
Figure 14B:
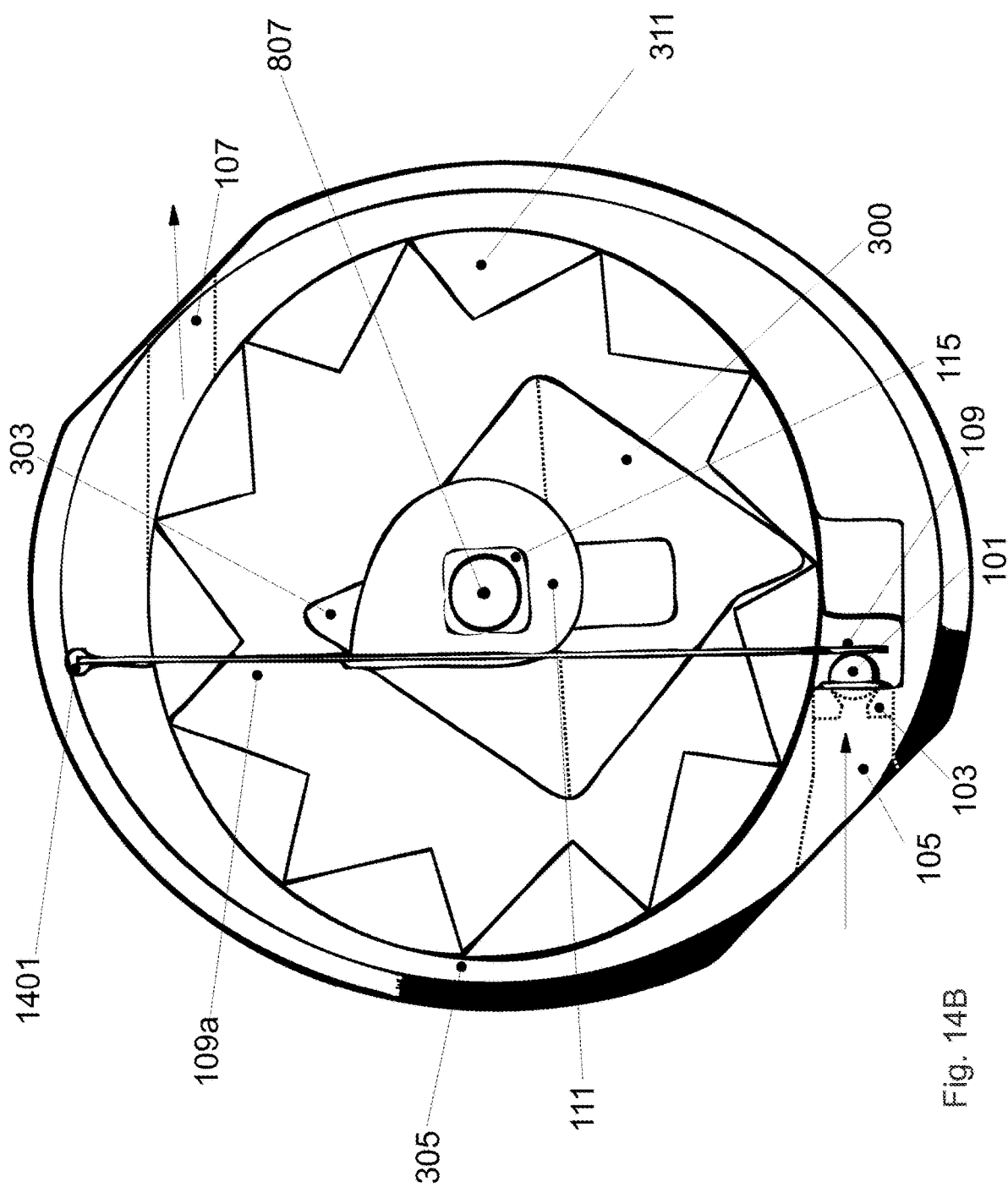
FIG. 14B is a plan view of another example of the valve assembly of FIG. 14A, in which the inlet and outlet ports are incorporated into the valve housing according to aspects of the invention.

After the valve assembly is manufactured, a calibration device is typically needed to adjust the pressure settings. For example, in certain embodiments the spring 109 may be constructed such that it is linear with respect to each step, that is, with each step of rotation of the cam 111, the spring 109 is tensioned so that the pressure of the valve goes up by X amount, and this is true for each additional step of rotation. Accordingly, it may be necessary to calibrate the device to set the cam 111 at a given position and pre-tension the spring 109 to an appropriate pressure for that position. Thereafter, the mechanism may be linear, as described above. Therefore, after the valve is assembled and during the calibration, there may be a flow of nitrogen (or some other fluid) through the valve assembly. Referring to FIG. 14A, in one embodiment, the inlet port 105 may be slowly screwed in, increasing the bias of the spring 109 against the valve element 101, until the desired setting is reached. At this position, a locknut 1403 may be used to secure the inlet port screw, and prevent it from moving. Referring to FIG. 14B, in another embodiment, the valve element 101 and valve seat 103 may be press-fit into the housing 1405, and, once the initial pressure setting is reached, held in place by the friction. In one example of this configuration, the valve element 101 includes a ruby ball, and the valve seat 103 is also made of ruby. The housing 1405 may be made of polyethersulfone. The configuration of FIG. 14B may be desirable at least in certain applications as it may have fewer components and may be simpler to build than the configuration of FIG. 14A.

Figure 16:
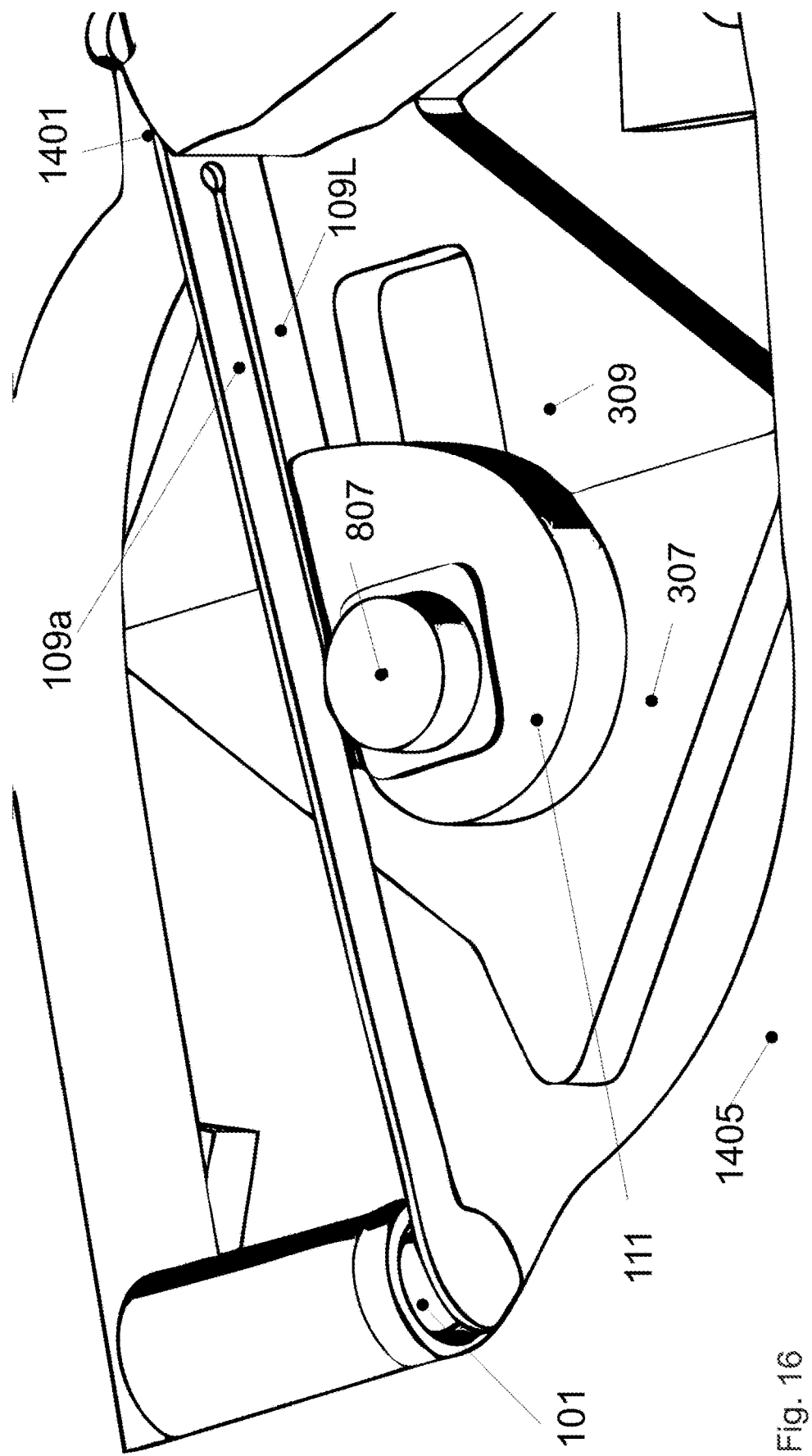
FIG. 16 is an enlarged view of a central portion of the valve assembly of FIGS. 14A and 14B.

FIG. 16 is an enlarged view of the central portion of the valve assembly of FIGS. 14A and 14B, showing the cam 111 coupled to the rotor 300, and the spring 109 biased against the valve element 101. As may be seen with reference to FIG. 16, in this example, the spring 109 includes the cantilevered arm 109a and a second arm 109L, both extending from the fixed point or fulcrum 1401 of the spring. The cam 111 engages the second arm 109L, and the free end of the cantilevered arm 109a rests against the valve element 101. The cantilevered arm 109a may be longer than the second arm 109L. As the rotor 300 rotates in the rotor casing 305, the cam 111 also rotates and presses against the second arm 109L of the spring, changing the tension in the spring. As discussed above, this cantilevered spring configuration may be desirable in certain applications of the valve assembly because it allows for very low pressure settings, without placing difficult or impracticable constraints on the rotational movement of the cam 111. By appropriately selecting the relative lengths of the two arms 109a, 109L, and the widths of the each arm, the equivalent of a lever or gear reduction mechanism may be achieved, as discussed above. Thus, a sufficiently soft spring to provide the low pressures (e.g., 0-200 mm $H_2O$) needed for certain applications may be achieved using a short, two-armed spring 109, rather than a conventional long spring.

Figure 18A:
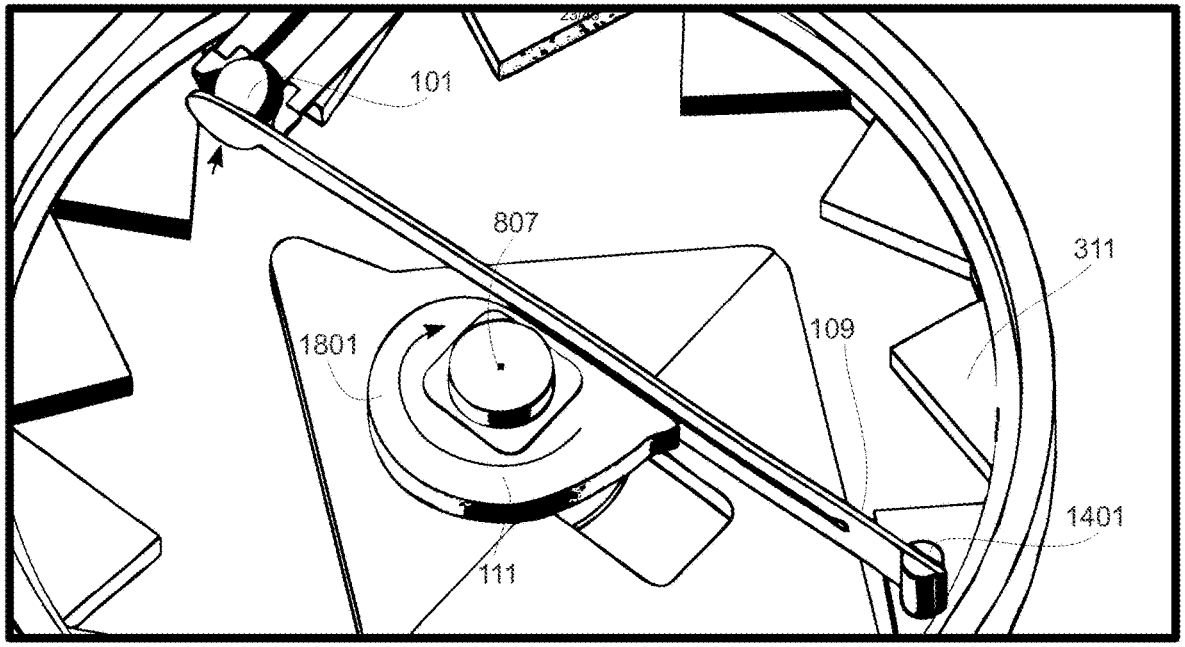
FIG. 18A is a diagram illustrating a portion of the valve assembly of FIGS. 14A and 14B, with the cam shown in a position of minimum tension in the biasing spring.
Figure 18B:
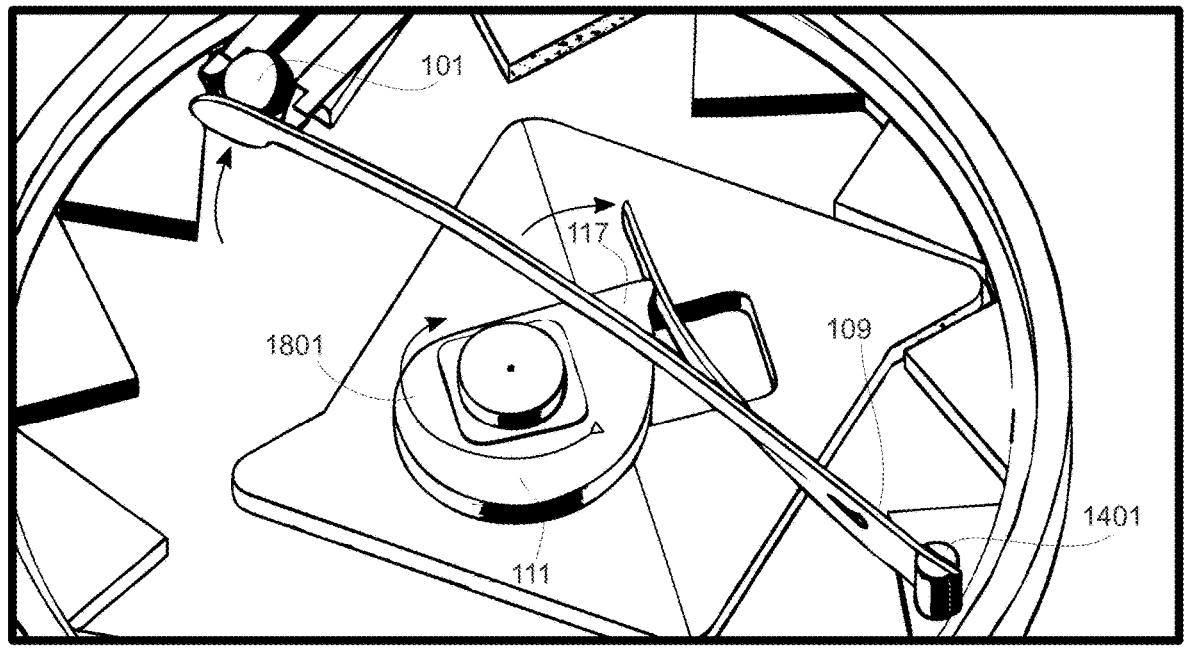
FIG. 18B is a diagram illustrating the same portion of the valve assembly of FIGS. 14A and 14B, with the cam shown in the a position of maximum tension in the biasing spring.

As discussed above, the rotor 300, and therefore the cam 111, rotates in steps defined by the number and configuration of the casing teeth 311, as discussed above. Thus, as shown in FIG. 17, as the cam 111 rotates, the pressure exerted against the spring 109 is adjusted in finite increments from a point of minimum pressure 1701 (corresponding to minimum tension in the spring 109) to a point of maximum pressure 1703 (corresponding to maximum tension in the spring 109). FIG. 18A illustrates the cam 111 in the position in which the minimum pressure is exerted by the cam against the spring 109, and the pressure setting of the valve is lowest. FIG. 18B illustrates the cam 111 in the position in which the maximum pressure is exerted by the cam against the spring 109, causing the cantilevered arm 109a to move toward the valve element 101. Thus, the pressure setting of the valve is highest for this position of the cam 111. In the illustrated example, the pressure exerted by the cam 111 against the spring 109, and therefore the tension in the spring, increases with clockwise rotation of the cam, as indicated by arrow 1801. However, those skilled in the art will appreciate, given the benefit of this disclosure, that the rotor, cam, and spring may alternatively be configured such that counter-clockwise rotation of the rotor increases the tension in the spring.

A cam in embodiments of the valve assembly disclosed herein, in any configuration, can have a constant or linear slope, a piecewise linear slope, a non-linear slope and combinations of such slopes in the surface(s) that engage the spring 109. If the cam has a linear slope, rotation of the cam increases or decreases the pressure setting in a linear way. If the cam has a non-linear slope, the pressure, for example, can increase more towards the end of the rotation. This allows the possibility of having minute increments of pressure initially, for example, between 0 and 200 mm H$_2$O, and larger increments of pressure thereafter. For example, the cam 111 illustrated in FIGS. 18A and 18B includes a surface with a non-linear slope that engages the second arm 109L of the spring 109. Specifically, the cam 111 includes a cam projection 117, which alters the rate of increase in the pressure exerted by the cam on the spring 109 as the cam rotates.

Figure 19:
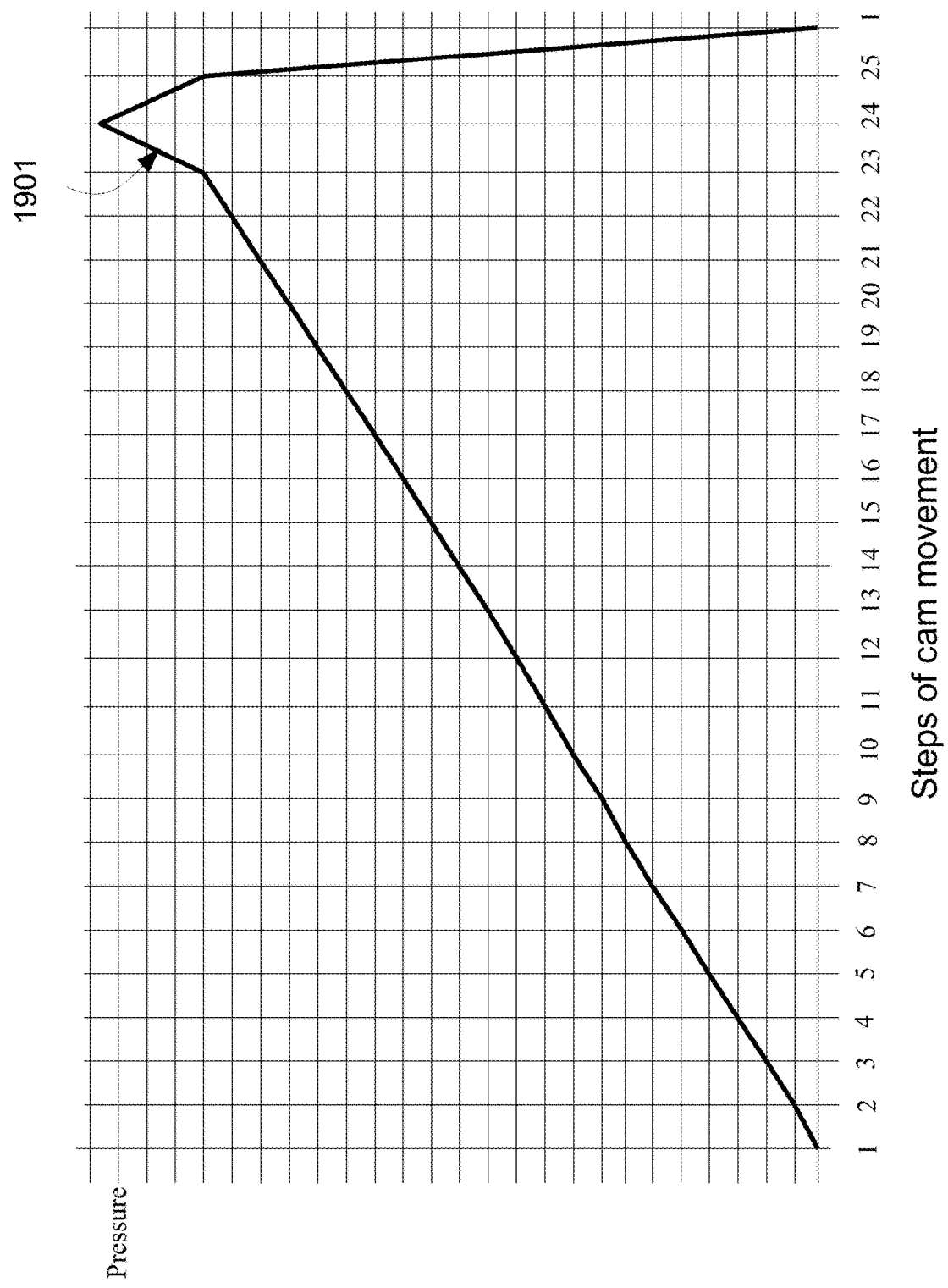
FIG. 19 is a graph of the pressure exerted against the spring by the cam as a function of cam rotation for one example of the valve configuration of FIG. 14A.

FIG. 19 is a graph illustrating the varying pressure exerted on the spring 109 by the cam 111 as a function of rotation of the cam (and therefore of the rotor 300). The example illustrated in FIG. 19 corresponds to the rotor, cam, and spring configuration illustrated in FIGS. 14-18B. For the example illustrated in FIG. 19, the rotor casing includes 13 casing teeth 311, corresponding to 25 steps of cam rotation (produced by 25 magnetic pulses of alternating polarity) to transition from the point of minimum pressure (1701 in FIG. 17) to the point of maximum pressure (1703 in FIG. 17). As may be seen with reference to FIG. 19, the pressure exerted by the cam 111 on the spring 109 increases in a substantially linear manner over the majority of the rotational cycle of the cam. However, toward the end of the cycle (cam step 23 to 24), the pressure increases more dramatically, shown by "peak" 1901 in FIG. 19. This peak 1901 is caused by the shape of the cam 111; specifically, by the cam projection 117 shown in FIGS. 18A and 18B. This change in the rate of increase of the pressure applied by the cam 111 against the spring 109 may also be seen in FIG. 17, where the incremental step in pressure closest to the point of maximum pressure 1703 is shown larger than the preceding increments.

In certain applications, for example, in the treatment of hydrocephalus in children, it may be desirable to be able to determine whether or not the patient is still in need of the valve after some time of use. For example, depending on the cause of hydrocephalus, after several years of using an implanted shunt valve assembly, the patient may no longer need the valve. One method of testing to determine whether or not the valve is still needed in the patient is to significantly increase the pressure of the spring against the valve element, thereby almost completely closing the valve, and observe the patient's condition thereafter. Accordingly, the above-described configuration in which the step pressure increase is significantly larger at or close to the maximum pressure position of the spring and cam may advantageously allow this testing to be performed. If the patient's condition deteriorates after the pressure setting of the valve is significantly increased, the pressure setting may simply be decreased again, by rotating the cam 111. Thus, this configuration provides a safe quasi-OFF setting for the valve, without having the valve completely closed or removed.

As discussed above, the inlet port 105 of the valve assembly may be connected to a proximal (or inflow) catheter, and the outlet port 107 may be connected to a distal catheter. In the case of a valve assembly that shunts CSF fluid, the CSF fluid from the ventricle enters the ventricular catheter and enters the inlet port 105 of the valve assembly. There are several possible orientations of the inlet port 105. Such configurations or orientations of the inlet port 105 can be described with reference to a central axis of the rotor 300 drawn from the top of the device through to the underside of the valve mechanism (for example, as indicated by the dashed line in FIGS. 8A-C). The "top" of the valve mechanism is the side of the device oriented to face up toward the patient's scalp when implanted. Fluid enters the housing via the ventricular catheter and flows through the inlet port 105 which terminates at its casing end at the valve seat 103. As described above, the valve element 101 and valve seat 103 form an aperture through which the fluid flows. The inlet port 105 can be oriented such that fluid enters the aperture (or, in other words, pushes against the valve element) in a direction parallel to the central axis of the rotor 300. Such configurations of the inlet port 105 are shown for example in FIGS. 2A-C in which a portion of the inlet port 105 is coaxial with the central axis of the rotor 300. The inlet port 105 can also be oriented such that fluid enters the aperture (or pushes against the valve element) in a direction that is perpendicular to the central axis of the rotor 300. Such a configuration of the inlet port 105 is shown, for example, in FIGS. 8A-C, where the casing end of the inlet port 105 is perpendicular to a central axis of the rotor 300. The configuration of the cam 111 and spring 109 can be described with reference to the orientation of the inlet port 105. In certain aspects, when the inlet port 105 is oriented such that fluid enters the aperture in a direction parallel to the central axis of the rotor, the cam 111 directly or indirectly produces vertical displacement of the spring 109. In additional aspects, when the inlet port 105 is oriented such that fluid enters the aperture in a direction perpendicular to the central axis of the rotor, the cam 111 directly or indirectly produces horizontal displacement of the spring 109. Examples of the spring 109 and cam 111 configurations that produce horizontal or vertical displacement of the spring 109 are described above. Other possible configurations of the spring 109 and cam 111 that produce horizontal or vertical displacement of the spring 109 will be appreciated by those skilled in the art, given the benefit of this disclosure, and are encompassed herein.

Figure 20:
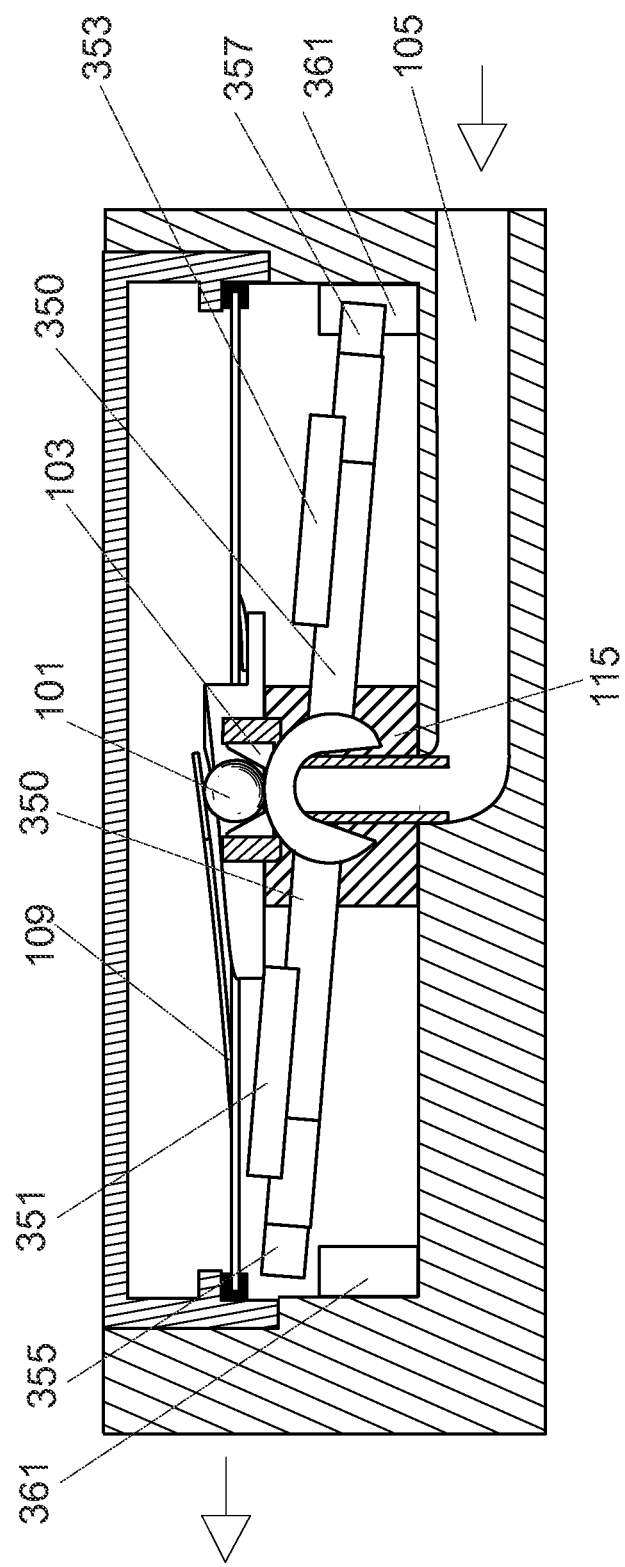
FIG. 20 is a cross-sectional view of one example of a valve assembly including a magnetic rotor that displaces up and down in a "see-saw" motion, according to aspects of the invention.

The preceding embodiments have described a magnetic rotor 300 that is displaced from side to side responsive to magnetic pulses. As discussed above, in other embodiments, the rotor may be displaced up and down, rather than from side to side. FIG. 20 is a cross-sectional view of a valve configuration with a magnetic rotor 350 that displaces up and down in a "see-saw" motion. Fluid enters the inlet port 105 and pushes against the valve element 101 which rests on the valve seat 103, similar to the configurations discussed above. The magnetic rotor 350 includes magnets 351 and 353, rotor teeth 355 and 357, and the rotor guide 115. The rotor teeth 355 and 357 are adapted to engage or interlock with the casing teeth 361 of the rotor casing. The spring 109 and cam 111 in this example are similar to those described above with reference to FIG. 3B. Rotation of the rotor 350 causes the cam 111 also to rotate in a clockwise direction. As in the configuration of FIG. 3B, the cam 111 has an inclined surface 113. Rotation of the cam 111 causes a change in the tension of the spring 109 resting on the inclined surface 113. When the spring 109 is resting against the inclined surface 113 at the lowest level of incline, the pressure setting of the valve will be highest. Conversely, when the spring 109 is resting against the inclined surface 113 at the highest level of incline (tending to push the cantilevered arm 109a up or in other words, in a direction opposite to the valve seat 103), the pressure setting of the valve will be the lowest.

Figures 22A, 22B:
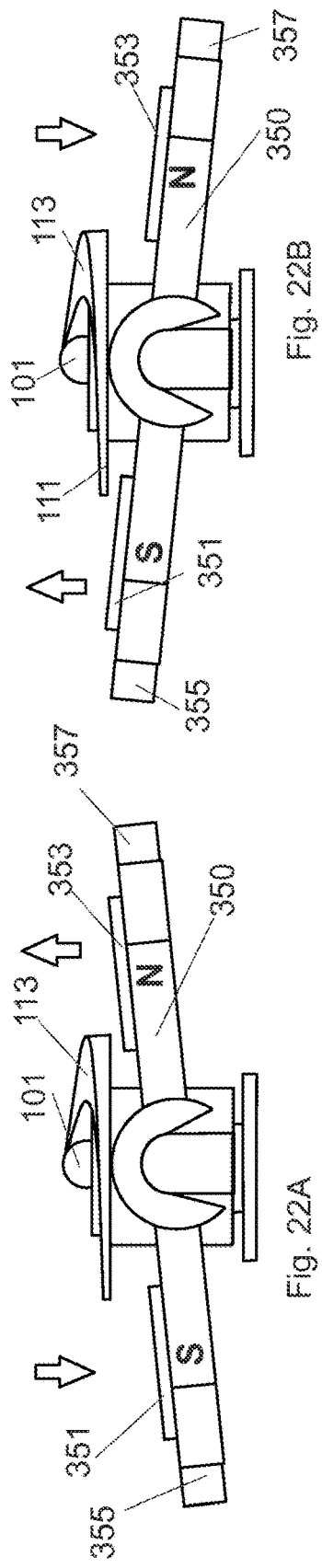
FIGS. 22A and 22B are side views of a portion of the valve assembly of FIG. 21, showing a magnetized coil in proximity to the valve and displacement of the up and down rotor in response to changing magnetic polarity of the coil, according to aspects of the invention.

FIG. 21 shows a three-dimensional view of an example of the up and down rotor 350 and the rotor casing 359. In this example, the spring 109 and cam 111 are similar to the configuration shown in FIGS. 7A and 7B. The rotor 350 is hinged along a central axis of the rotor to a rotating disc 363 within the rotor casing 359. FIGS. 22A and 22B, 23A and 23B, and 24A and 24B illustrate side views of the magnetic rotor 350 and valve assembly configuration of FIG. 21. FIGS. 22A and 22B illustrate a magnetic coil 2201 in proximity to the valve, and show the interaction of the magnets 351 and 353 of the rotor 350 with the external magnetic field produced by the magnetic coil 2201. According to one aspect, the magnetic coil 2201 used in conjunction with embodiments of an up-and-down rotor 350 includes a solid rod or bar used as the nucleus or core of the coil (i.e., around which the coil is wound). This solid core of the coil 2201 may be placed on top of a central part of the rotor 350, such that the magnetic field is applied from above the rotor. FIG. 22A shows the attraction of the north pole of magnet 351 toward south pole of the external magnetic field. In FIG. 22B the polarity of the external magnetic field is reversed and now attracts the south pole of magnet 353. Thus, cycling between these external magnetic field polarities induces the up and down displacement, or "see-saw" motion of the rotor 350. Each pulse of an external magnetic field (e.g., from the coil 2201) causes one rotor tooth 355 or 357 to engage with the casing teeth 361 (the "down position") while the tooth on the other rotor end is not engaged with the casing teeth (the "up" position). For example, as shown in FIGS. 22A, 23A, and 24A, when the rotor tooth 355 proximal to the north pole of the rotor 350 is in the "down" position, engaged with the casing teeth 361, the rotor tooth 357 proximal to the south pole of the rotor is in the "up" position and not engaged with the casing teeth 361, and vice versa. As the rotor 350 is displaced up and down, it is guided by the casing teeth 361 arranged on the inner circumference of the casing 359. Thus, with each up and down displacement of the rotor 350 (responsive to a pair of magnetic pulses of opposite polarity), the rotor rotates within the rotor casing 359 incrementally, one casing tooth 361 at a time. As in the case of the valve with the side-to-side rotor, the degrees of rotation of the rotor 350 in response to each magnetic pulse can be varied by changing the number of casing teeth 361.

Figure 25:
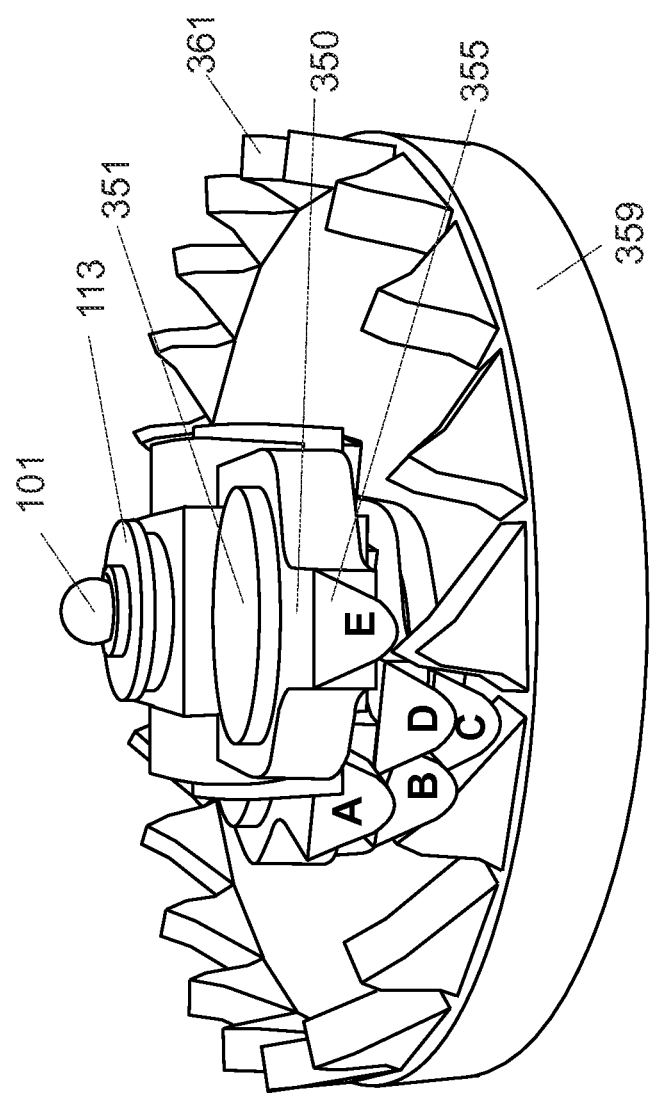
FIG. 25 is a three-dimensional drawing of one example of an up-and-down rotor showing the sub-incremental movement of the rotor within the rotor casing as it displaces up and down and the interplay between the rotor teeth and the casing teeth, according to aspects of the invention.

FIGS. 25, 26, 27A-E, and 28A-E show the sub-incremental movements (A, B, C, D, and E) of the rotor teeth 355, 357 as the up-and-down rotor 350 rotates with the rotor casing 359. FIG. 25 shows these movements for rotor tooth 351. Positions A and B show the movement of the rotor tooth 355 as it engages between the casing teeth 361. Position C shows the rotor tooth 355 engaged between the casing teeth 361. Positions A, B and C can result from a downward pivoting of the rotor end containing the rotor tooth 355. As the rotor tooth engages the inclined surface of the opposing casing tooth, a portion of the downward axial force is transformed by the inclined plane into a circumferential force causing rotation from position B to position C. Positions D and E show movement of the rotor tooth 355 as it moves to the next position between casing teeth 361. The movement from position C to positions D and then E results from a downward pivoting of an opposite end of the rotor, and a similar action occurring between the rotor tooth on the opposite end against an opposing casing tooth.

Figure 26:
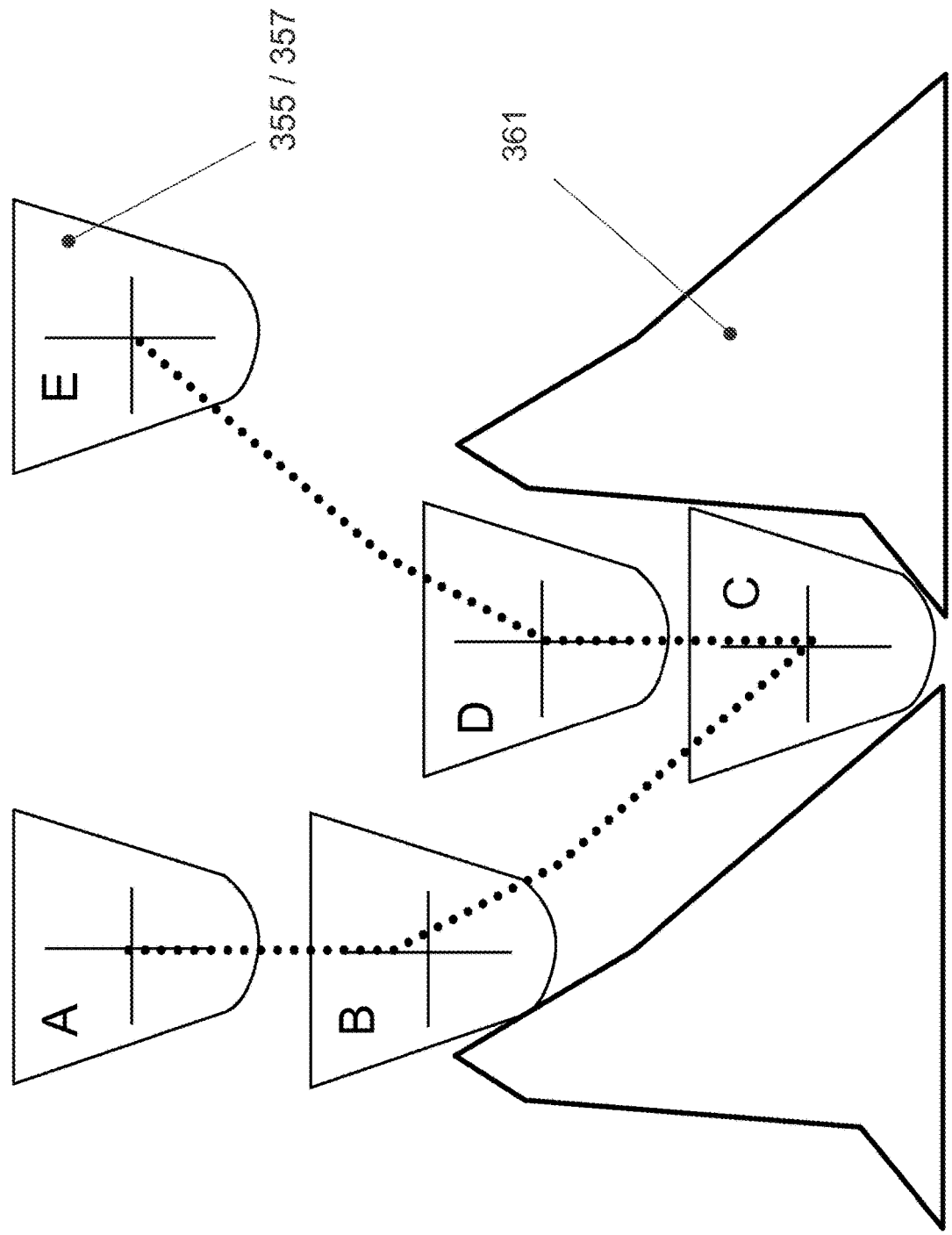
FIG. 26 is a diagram schematically showing an enlarged view of the sub-incremental movement of the rotor teeth with respect to the casing teeth as the rotor displaces up and down, according to aspects of the invention.

FIG. 26 provides an enlarged view of the sub-incremental movements A-E shown in FIG. 25.

FIGS. 27A-E and 28A-E show sub-incremental movements of both rotor teeth 355 and 357 of the up-and-down rotor 350. FIGS. 27A-E show the movement of the "front side" rotor tooth 355, and FIGS. 28A-E show the movement of the "back side" rotor tooth 357. As the "back side" rotor tooth 357 is engaged between the casing teeth 361, the "front side" rotor tooth 355 is not engaged (or in other words, is in the up position), as shown in FIGS. 27A, 27E, and 28A, 28E. Similarly, as shown in FIGS. 27C and 28C, as the rotor tooth 355 is engaged between the casing teeth 361, the rotor tooth 357 is in the up position.

The various configurations of the inlet port 105, cam 111, spring 109, and other components of the valve assemblies described above for the side-to-side rotor 300 may also be used in conjunction with a valve assembly comprising the up-and-down rotor 350. For example, the side-to-side rotor 300 in the exemplary configurations depicted in each of FIGS. 3A-16, 18A and 18B may be replaced with an up-and-down rotor 350. In another example, a valve including an up-and-down rotor 350 may include a disc cam 801 or a cam 111 with an inclined surface 113, and/or a spring 109 comprising a helical spring or a cantilever spring.

Figure 29A:
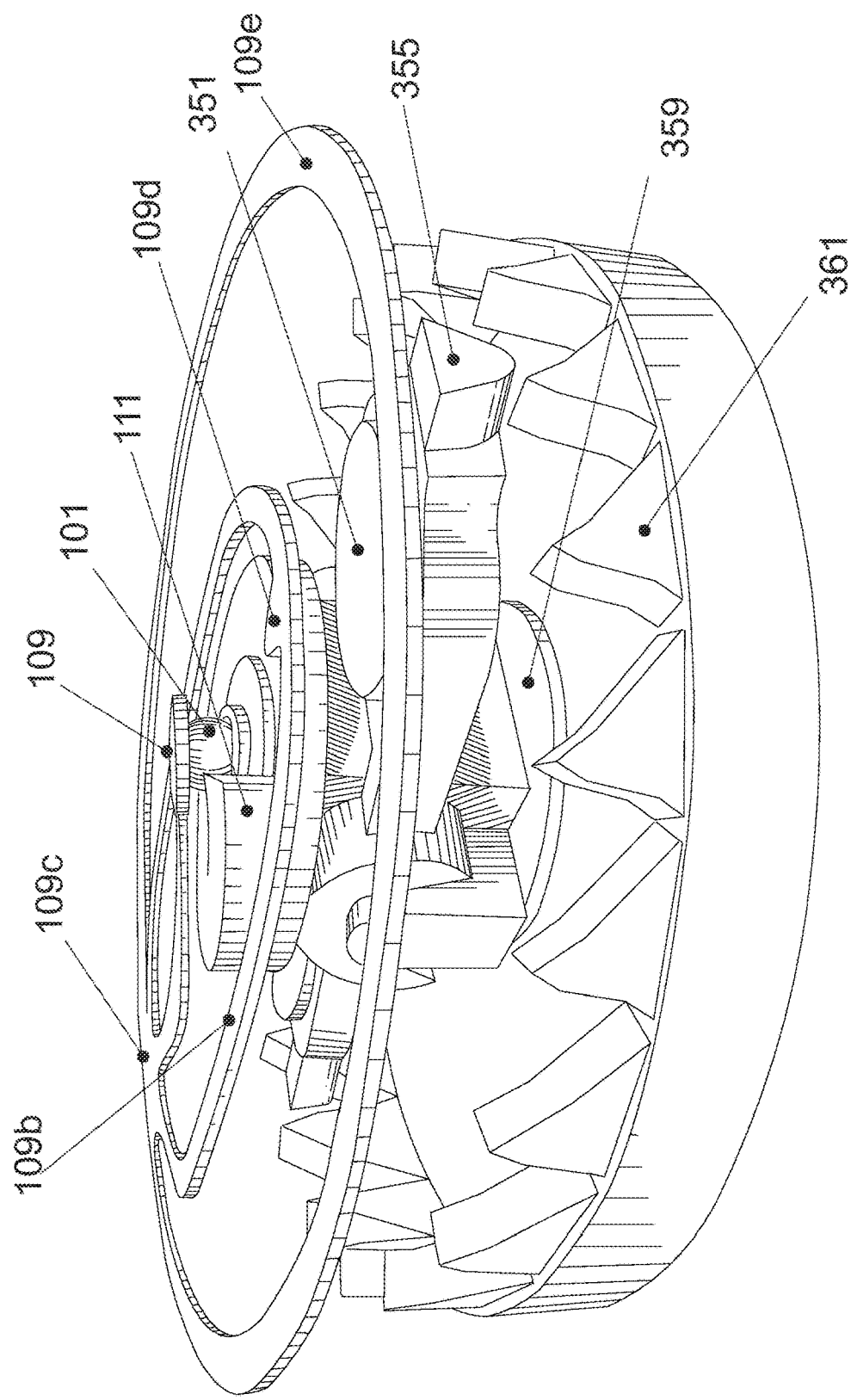
FIGS. 29A and 29B are three-dimensional drawings of one example of a magnetic rotor that displaces up and down, according to aspects of the invention.
Figure 29B:
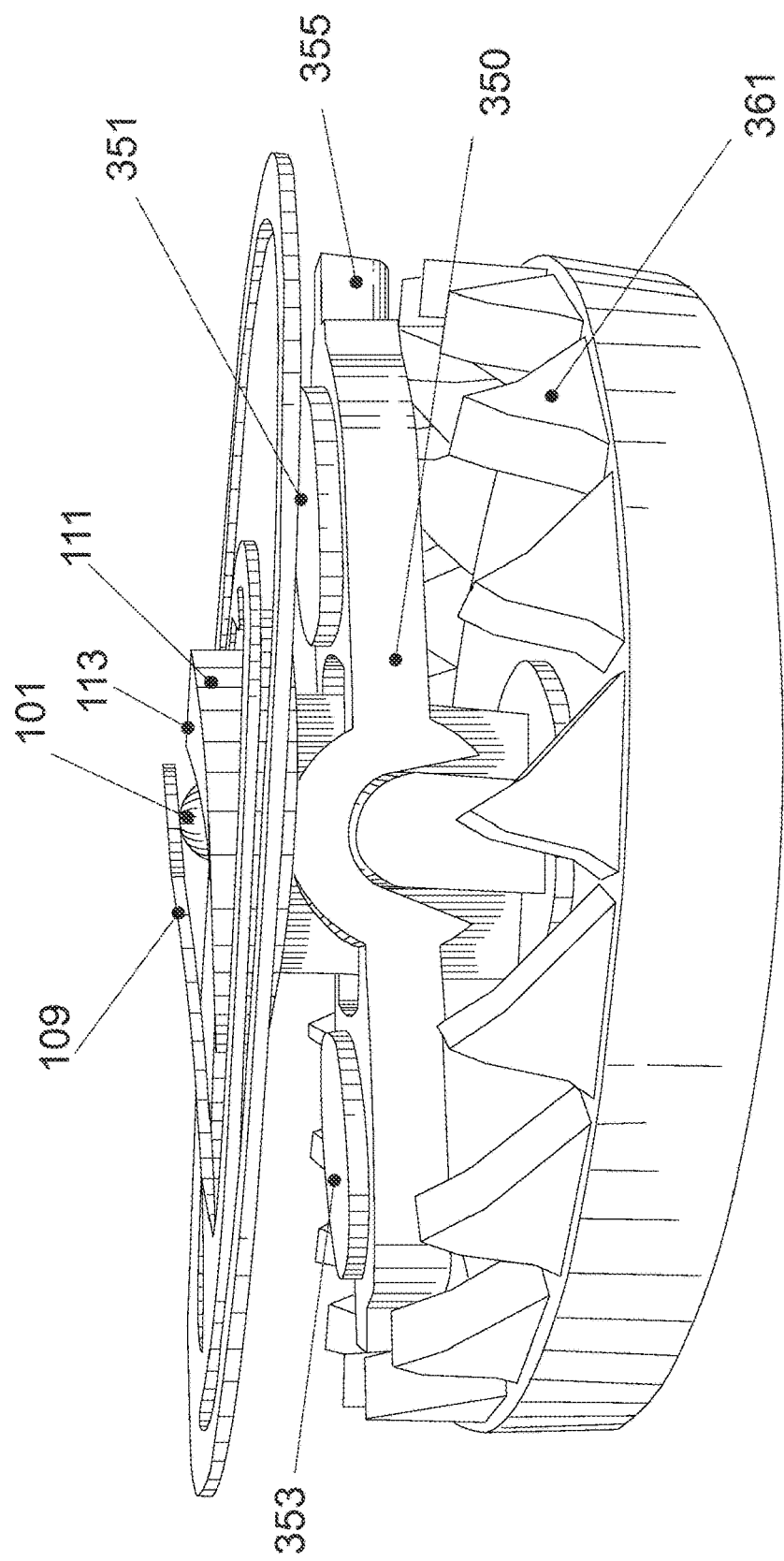

For example, FIGS. 29A and 29B show side views of a configuration of the up-and-down rotor 350 with a cantilever spring 109 and cam 111 similar to that of FIGS. 3A, 3B, 7A, and 7B. As in the configuration depicted in FIGS. 7A and 7B, as the rotor rotates, the rotor causes the cam 111 to also rotate and increase or decrease the tension in the spring 109. Like in the configuration of FIGS. 7A and 7B, the spring 109 includes a cantilevered arm 109a with the free end of the cantilevered arm biased against the valve element 101. The cantilevered arm 109a extends from (or is attached to, for example, welded to) an oblong-shaped ring 109b, which includes a fixed end 109c and a free end 109d. In the illustrated example, the free end 109d of the oblong-shaped ring 109b is about 180° from the fixed end 109c, and the free end 109d rests against the cam 111. The fixed end 109c of the oblong shaped ring 109b is, in turn, fixed to an outer ring 109e that rests over the casing teeth 361 at the periphery of the rotor casing 359. Rotation of the rotor 350 in a clockwise direction causes the cam 111 also to rotate in a clockwise direction. Rotation of the cam 111 causes a change in the tension of the spring 109 resting over the cam.

FIGS. 30A and 30B, 31A and 31B, and 32A and 32B show top and side views, respectively, of an example of the up-and-down rotor 350. FIGS. 30A and 30B show an example of the rotor 350 and the rotor casing 359 (including the casing teeth 361). FIGS. 31A and 31B are similar to FIGS. 30A and 30B, except that a cam 111 with an inclined surface 113 is also shown over the rotor 350. FIGS. 32A and 32B are similar to FIGS. 31A and 31B, except that the spring 109 is also shown. The valve assembly of FIGS. 32A and 32B includes a cantilever spring 109 and cam 111, such as those described above with reference to FIGS. 7A and 7B.

Those skilled in the art will appreciate, given the benefit of this disclosure, that the length, size, and shape of various embodiments of the valve assembly can be adjusted. Certain embodiments of the valve assembly may further comprise a reservoir or pre-chamber for sampling the fluid and/or injecting pharmaceutical agents or dyes, power on/off devices, anti-siphon or other flow compensating devices, and/or additional catheters, as discussed further below.

FIGS. 33A-36B illustrate exemplary configurations of a valve assembly including the up-and-down rotor 350 described above disposed within the housing 1405. FIG. 33A is a side view of a portion of the valve assembly, and FIG. 33B is a corresponding top view. Fluid enters the housing 1405 (for example, via a catheter) and flows through the valve to the outlet port 107 (as indicated by the arrows in FIG. 33A).

Figure 35A:
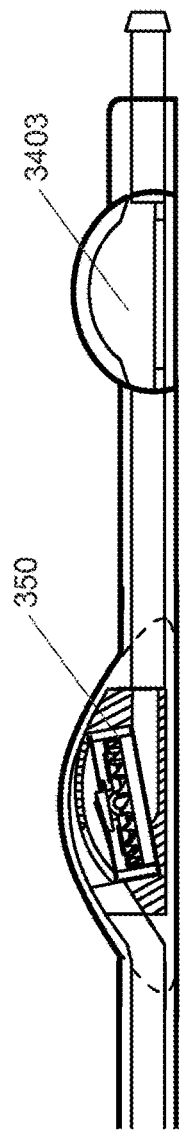
FIG. 35A is a side view of one example of a valve assembly including a valve with an up-and-down magnetic rotor and a pre-chamber, according to aspects of the invention.
Figure 35B:
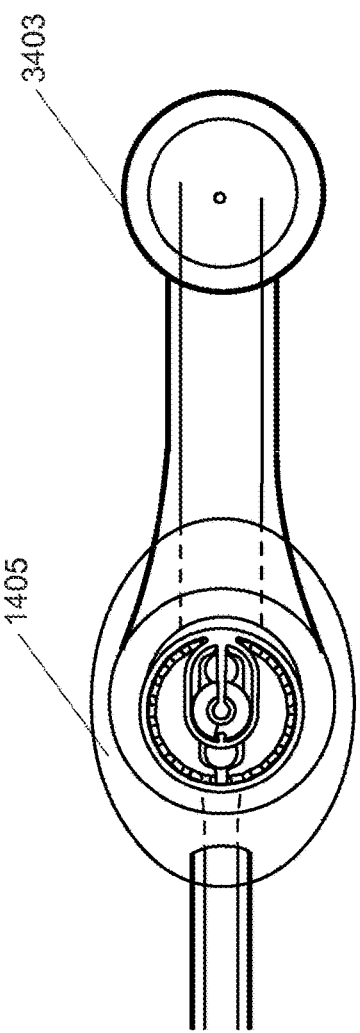
FIG. 35B is a top view of the valve assembly of FIG. 35A.

Referring to FIGS. 34A and 34B, in certain embodiments, the valve assembly comprises a pumping chamber 3401 located between the input port 105 and the exit port 107. Depression of the pumping chamber 3401 pumps fluid through the valve into the exit port 107. In certain embodiments, the valve assembly may comprise a pre-chamber 3403, as also shown in FIGS. 35A and 35B. The pre-chamber 3403 is a chamber within the system through which fluid passes before passing through the valve comprising the magnetic rotor 350. The pre-chamber 3403 may be used to sample fluid. For example, a physician may insert a needle into the pre-chamber 3403 and withdraw a sample of fluid. Accordingly, the pre-chamber 3403 may further comprise a metal needle stop 3405. Referring again to FIGS. 34A and 34B, according to some embodiments, the valve assembly may include a check-valve 3407 within the outlet port side of the housing 1405. After passing through the valve, fluid enters the outlet port 107 and flows through the check valve 3407. The check valve 3407 may include, for example, a spherical element 3409 (for example, a ball) and a spring 3411. The check valve operates, using the action of the spring 3411, to keep the valve closed until the CSF pressure rises to a predetermined pressure setting of the valve. Generally, the check valve 3407 may be set at a low pressure, allowing the pressure setting of the valve including the magnetic rotor 350 to control the flow of fluid through the valve assembly.

Figure 35C:
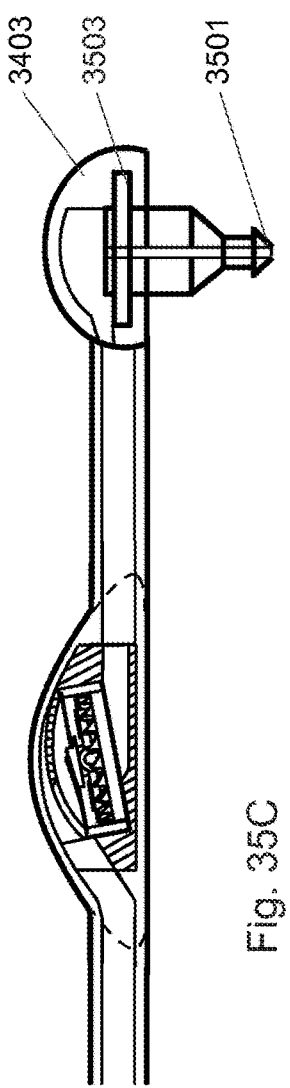
FIG. 35C is a side view of the valve assembly of FIGS. 35A and 35B, also showing a catheter connection mechanism within the pre-chamber, according to aspects of the invention.
Figure 36A:
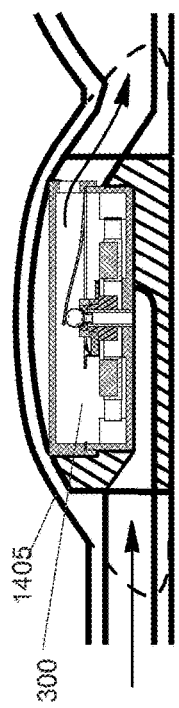
FIG. 36A is a cross-sectional side view of one example of a valve assembly including a side-to-side magnetic rotor within a valve housing according to aspects of the invention.
Figure 36B:
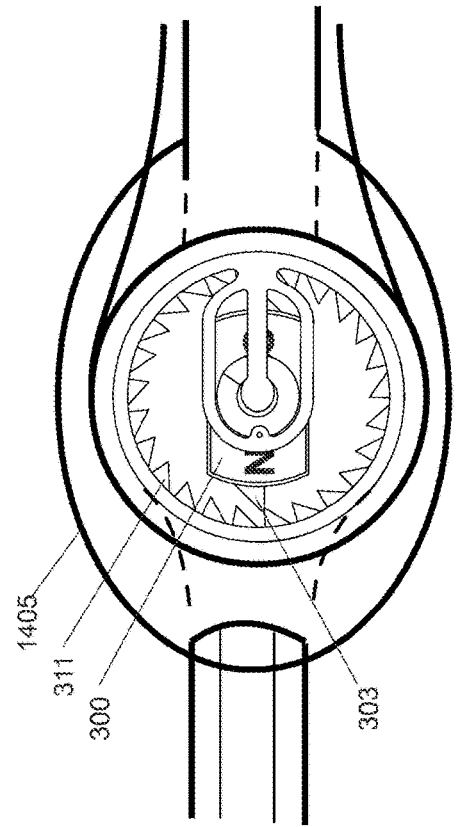
FIG. 36B is a top view of the valve assembly of FIG. 36A.
Figure 37A:
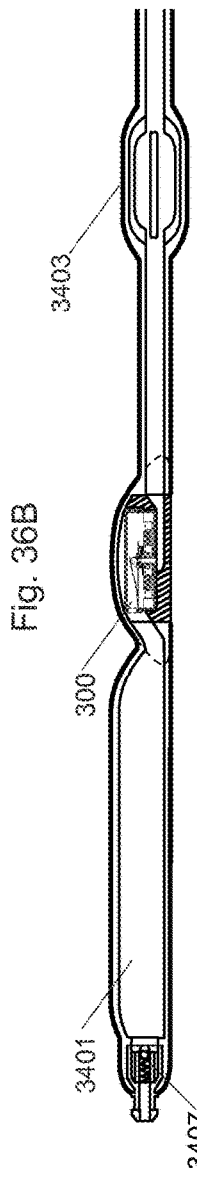
FIG. 37A is a side view of one example of a valve assembly including a valve with a side-to-side magnetic rotor, a pre-chamber, a pumping chamber, and a check valve, according to aspects of the invention.
Figure 37B:
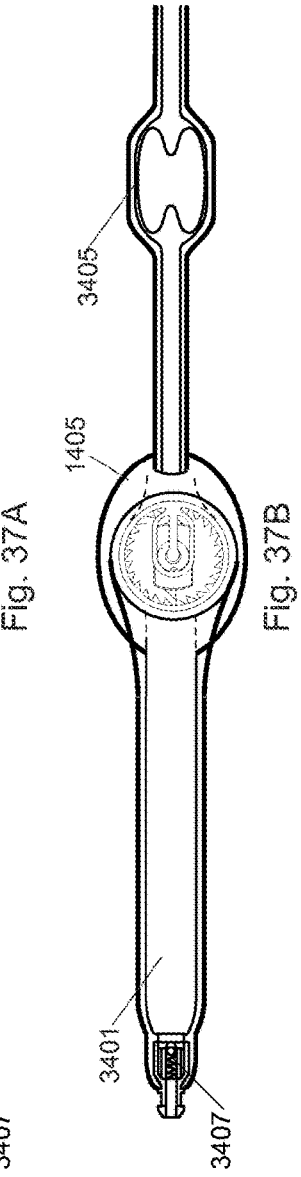
FIG. 37B is a top view of the valve assembly of FIG. 37A.
Figure 38A:
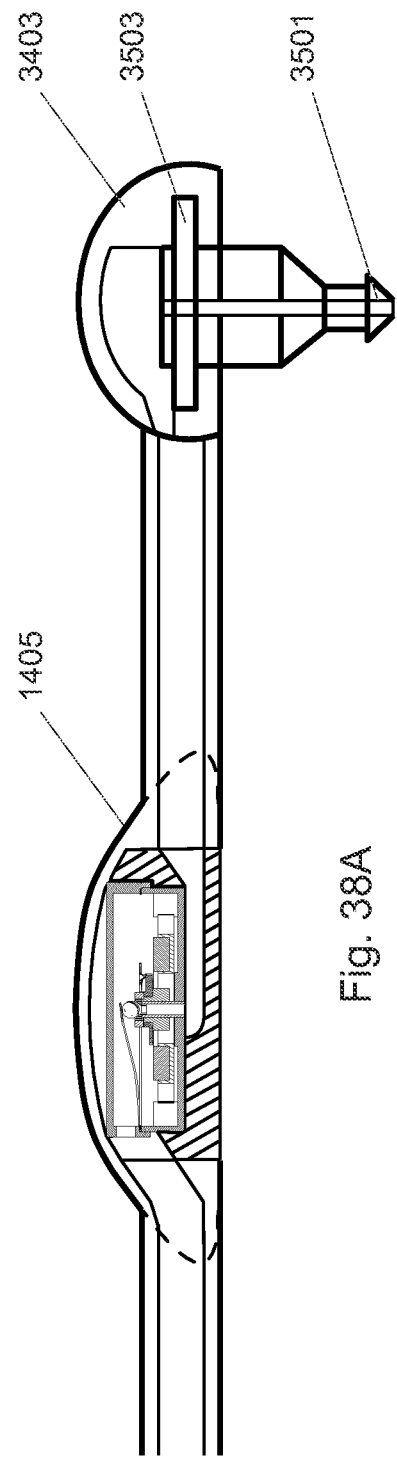
FIG. 38A is a side view of one example of a valve assembly including a valve with a side-to-side magnetic rotor and a pre-chamber, also showing a catheter connection mechanism within the pre-chamber, according to aspects of the invention.
Figure 38B:
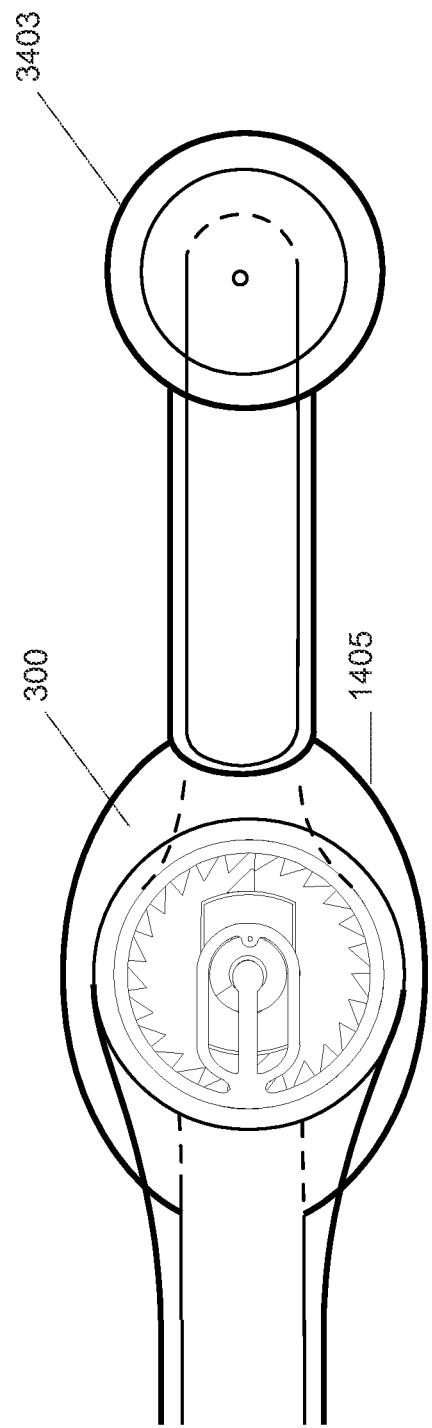
FIG. 38B is a top view of the valve assembly of FIG. 38A.

According to certain embodiments, the valve assembly may include a combination of the pumping chamber 3401, pre-chamber 3403, check valve 3407, and optionally an anti-siphon device. In other embodiments, one or more of these components may be omitted. For example, the valve assembly may include the pumping chamber 3401 and check valve 3407, without a pre-chamber 3403. The pumping chamber may also or alternatively be omitted. In such embodiments, after the fluid passes through the valve comprising the magnetic rotor, it flows through the outlet port 107 to the check valve 3407. Alternatively, the valve assembly may include the pre-chamber 3403, with or without the pumping chamber 3401 and/or the check valve 3407. According to one embodiment, in which the valve assembly includes the pre-chamber 3403, a ventricular catheter (not shown) may be attached at 3501 at the bottom of a funnel-shaped connector 3503 within the pre-chamber 3403, as illustrated in FIG. 35C.

FIGS. 36A and 36B, 37A and 37B, and 38A and 38B, show exemplary configurations of a valve assembly including a side-to-side rotor 300 within the housing 1405. These configurations are the same as those described above with reference to FIGS. 33A-35C, except that the up-and-down rotor 350 is replaced with the side-to-side rotor 300.

According to one embodiment, the valve assembly is configured to automatically adjust in response to changes in CSF hydrostatic pressure that occur when the patient moves from a horizontal to a vertical position. As discussed in more detail in U.S. Pat. No. 3,889,687, the contents of which are incorporated by reference herein, the hydrostatic pressure working on the check valve increases abruptly when a patient shifts from a substantially horizontal position to a substantially vertical position. This pressure change can cause the valve to open. The valve opening in response to the change in pressure can result in over-drainage of CSF when the patient moves to a substantially vertical position. Therefore, in certain embodiments, the valve assembly further comprises a gravity activated valve 3901 or positional pressure control, connected in series with a programmable valve 3903, as shown in FIG. 39. The programmable valve 3903 includes a magnetic rotor 300 or 350 as described above. FIGS. 40A and 40B illustrate an example of a valve assembly including the gravity-activated valve 3901 connected in series with a programmable valve 3903 that includes an embodiment of the side-to-side magnetic rotor 300. FIGS. 41A and 41B illustrate an example of a valve assembly including the gravity-activated valve 3901 connected in series with a programmable valve 3903 that includes an embodiment of the up-and-down magnetic rotor 350.

Referring to FIGS. 39, 40A-B, and 41A-B, the gravity activated valve 3901 may be located on the outlet side of the programmable valve 3903, such that fluid flowing out of the programmable valve flows through the gravity activated valve (depending on the pressure setting of the valve assembly). The gravity activated valve 3901 adjusts to a closed position and opens at higher pressures when the patient is substantially vertical (position A in FIG. 39). The gravity activated valve is open when the patient is substantially horizontal (position B in FIG. 39). As such, the valve assembly comprising the programmable valve 3903 and a gravity activated valve 3901 may have two operating pressures: one operating pressure for when the patient is substantially horizontal and a second operating pressure for when the patient is substantially vertical. The operating pressure when the patient is substantially horizontal is less than the operating pressure when the patient is substantially vertical.

Figure 42:
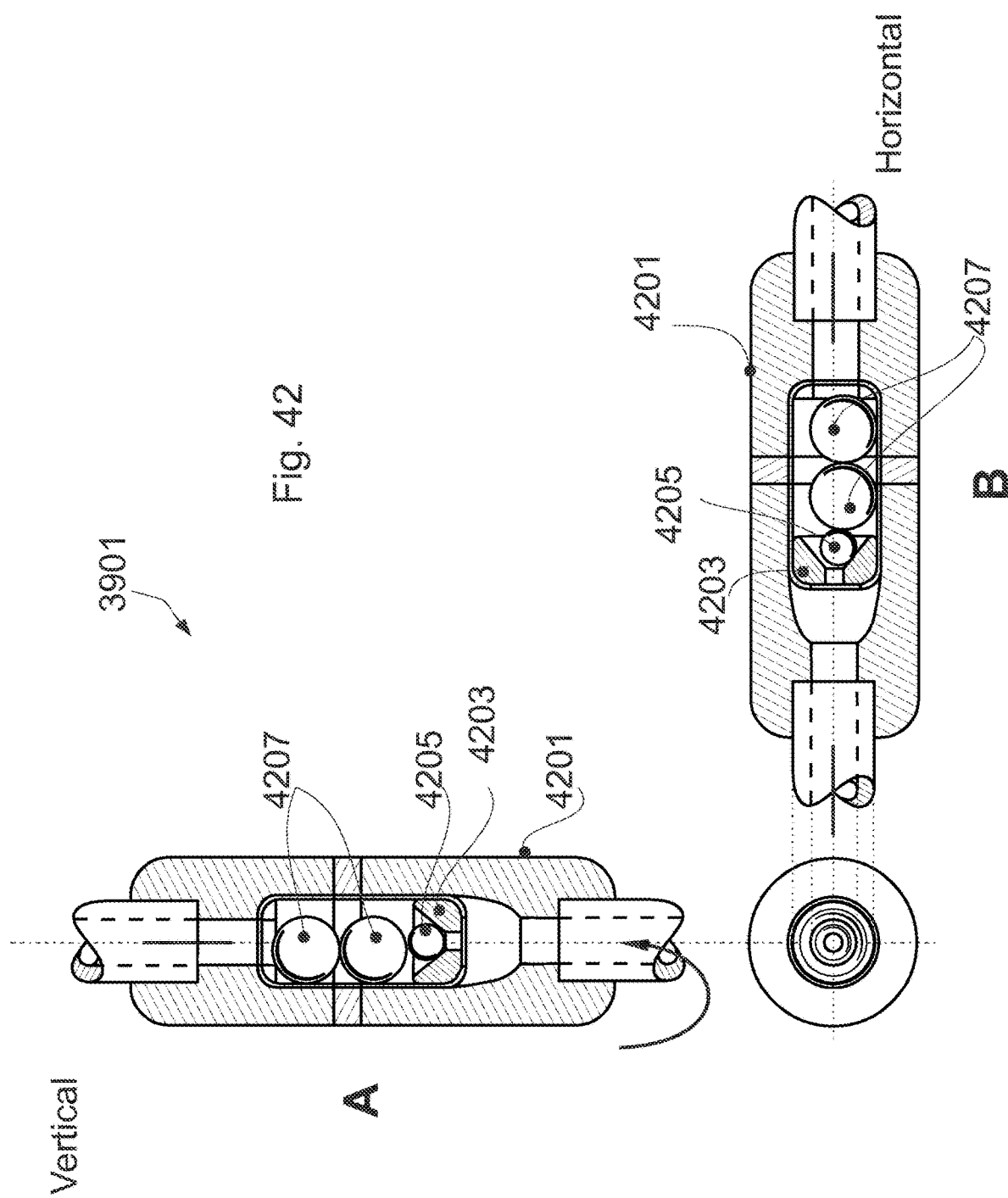
FIG. 42 is a diagram of one example of a gravity-activated valve according to aspects of the invention.

FIG. 42 is a diagram of one example of the gravity-activated valve 3901, showing the transition of the valve from position A (corresponding to the patient being in the substantially vertical position, as shown in FIG. 39) to position B (corresponding to the patient being in the substantially horizontal position, as shown in FIG. 39). In one embodiment, the gravity activated valve 3901 includes a casing 4201 and within the casing, a valve seat 4203 and a valve element 4205. Similar to the magnetically programmable valves 3903 discussed above, the diameter of the valve element 4205 is greater than that of the valve seat 4203, and the valve element and valve seat together form an aperture. This aperture is closed when the valve element 4205 is seated or pressed against the valve seat 4203, and opens when the valve element is unseated. This type of valve mechanism, including the valve element and valve seat, is also referred to in the literature as a "ball-in-cone" valve. In certain embodiments, the gravity activated valve 3901 further includes one more balls 4207 disposed within the casing 4201. These balls 4207 may serve as weights that can roll toward and press the valve element 4205 against the valve seat 4203 (for example, when the patient is in a substantially vertical position), or can roll away from the valve element 4205, permitting the valve element to unseat itself and opening the aperture for the flow of CSF (for example, when the patient is in the horizontal position). Various examples of gravity activated valves are known in the art and are described, for example, in U.S. Pat. No. 3,889,687

Figure 43:
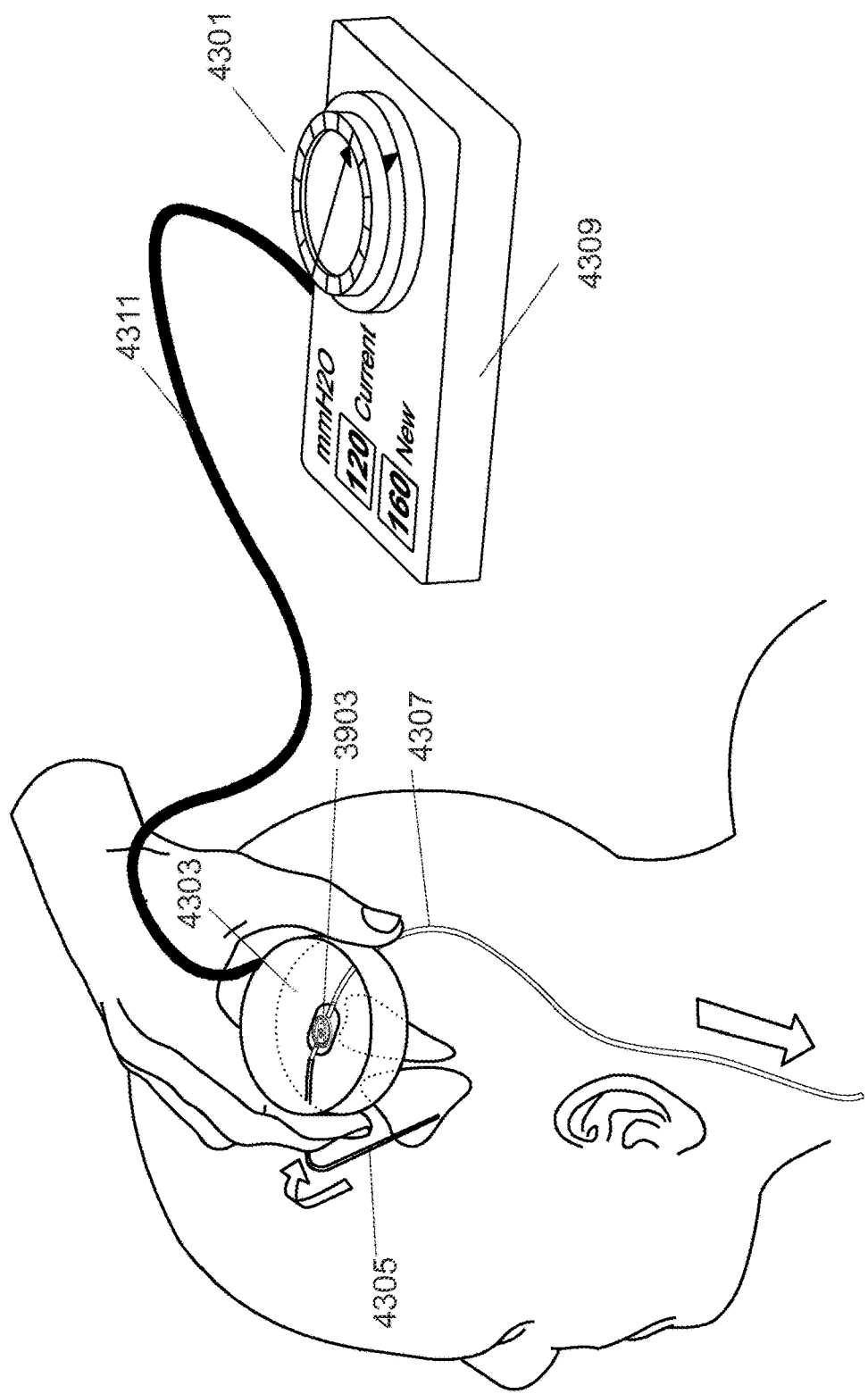
FIG. 43 is a diagram of an implanted valve and an external valve programmer, according to aspects of the invention.

As discussed above, because embodiments of the valve assembly comprise a magnetic rotor, the pressure setting of the implanted valve can be adjusted by positioning an external adjustment device (also referred to herein as a valve programmer) in proximity to the implanted valve 3601 but external to the body. The polarity of a magnetic coil within the adjustment device can be altered to cause displacement of the magnetic rotor 300 or 350, as discussed above. FIG. 43 illustrates an adjustment device 4301 including a transmitter head 4303 which may be placed over the patient's head at a location over an implanted magnetically-programmable valve assembly 3903. The transmitter head 4303 includes a magnetic coil 4313, as discussed above. Fluid flows from the ventricle, through a ventricular catheter 4305, through the implanted valve, into the distal catheter 4307, which then drains the fluid at a remote location of the body (such as the right atrium of the heart or to the peritoneal cavity). The valve programmer 4301 may send a magnetic signal through the transmitter head 4303 to effect displacement of the rotor 300 or 350. A control device 4309 may be used to control the transmitter head 1403 to produce the magnetic pulses, as discussed further below, and may be coupled to the transmitter head via a cable 4311.

FIGS. 44A-C depict an example of the magnetic coil 4313 within the transmitter head 4303, and the magnetic rotor 300 that displaces from side to side within the rotor casing 305. The ends of the rotor 300 are of opposite magnetic polarity. As discussed above, in embodiments where an up-and-down rotor 350 is used, the magnetic coil includes a solid core. In contrast, in embodiments where a side-to-side rotor 300 is used, the magnetic coil instead includes a hollow core (e.g., a hollow tube around which the coil is wound), such that the hollow core may be placed substantially around the valve in order to have the magnetic field sideways to the rotor 300, to the extent feasible.

In FIG. 44A, the coil 4313 is energized such that the portion of the coil in closest proximity to the rotor 300 is magnetized south. In FIG. 44B, the polarity of the coil 4313 is such that the portion of the coil in closest proximity to the rotor 300 is magnetized north. In FIG. 44C, the polarity of the coil 4313 is again such that the portion of the coil in closest proximity to the rotor 300 is magnetized south. As shown in FIG. 44A, when the lower circumference of the coil 4313 (the portion of the coil in closest proximity to the valve) is magnetized south, the south pole of the rotor 300 is repelled and the north pole of the rotor is attracted. Accordingly, the rotor 300 is displaced from one side of the rotor casing 305 to the other side in a direction toward the coil 4313, as discussed above. Similarly, in FIG. 44B, when the coil 4313 is magnetized north, the north pole of the rotor 300 is repelled and the south pole of the rotor is attracted. As a result, the rotor 300 is displaced toward the coil 4313. As shown in FIG. 44C, when the lower perimeter or circumference of the coil 4313 is polarized south, the north pole of the rotor 300 attracted toward the coil and is displaced from one side of the rotor casing 305 to the other toward the coil. Thus, by controlling the magnetic coil 4313 within the transmitter head 4303 to produce magnetic pulses of opposite polarity, the rotor 300 may be caused to rotate within the rotor casing 305, as discussed above, and the pressure setting of the implanted valve 3903 can be adjusted.

Figure 45A:
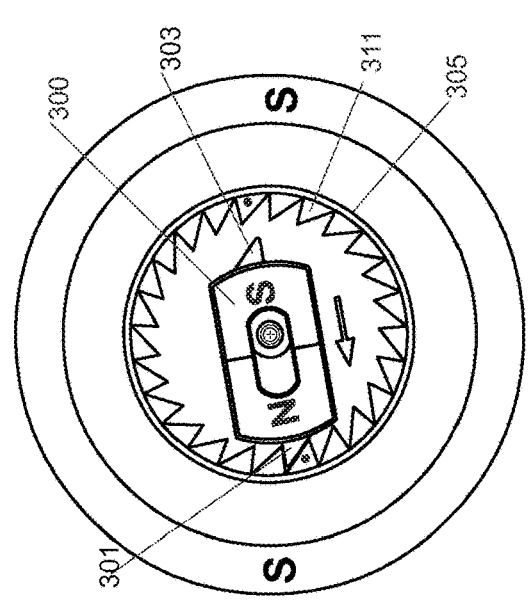
FIGS. 45A-C are diagrams showing an example of the magnetic rotor displaced from side-to-side within the rotor casing in response to the changing magnetic field shown in FIGS. 44A-C, according to aspects of the invention.
Figure 45B:
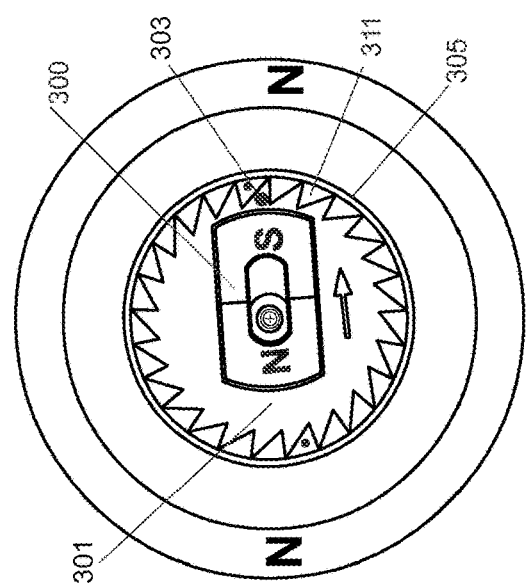
Figure 45C:
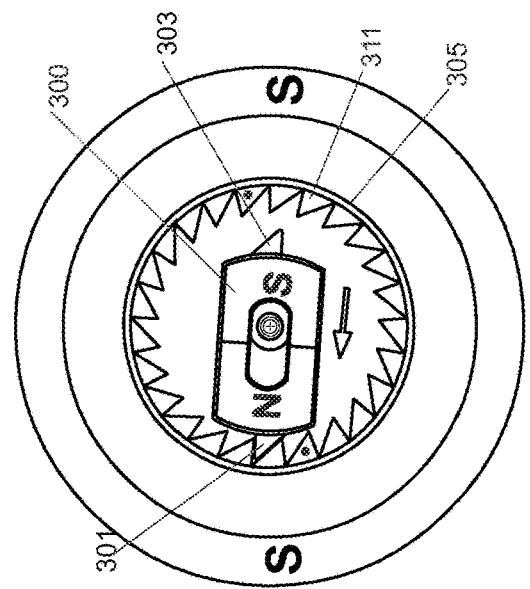

FIGS. 45A-C present an enlarged, top view of the rotor 300 and the rotor casing 305, showing the movement of the rotor in response to the changing polarity of the coil 4313 depicted in FIGS. 44A-C. The rotor 300 displaces from one side of the rotor casing 305 to the other side of the casing in response to each change in the polarity of the portion of the coil 4313 in closest proximity to the valve. As the rotor 300 is displaced, it is guided by the casing teeth 311 arranged on the inner surface of the rotor casing 305. As discussed above, the degrees of rotation of the rotor 300 in response to each magnetic impulse can be varied by changing the number of casing teeth 311.

Similarly, the magnetic coil 4313 within the transmitter head 4303 may be controlled, via the controller 4309, to produce magnetic pulses to operate an implanted valve 3903 that includes an up-and-down rotor 350, as discussed above. In this case, the magnetic coil 4313 may include an embodiment of the magnetic coil 2201 having a solid core, as discussed above.

Figure 46:
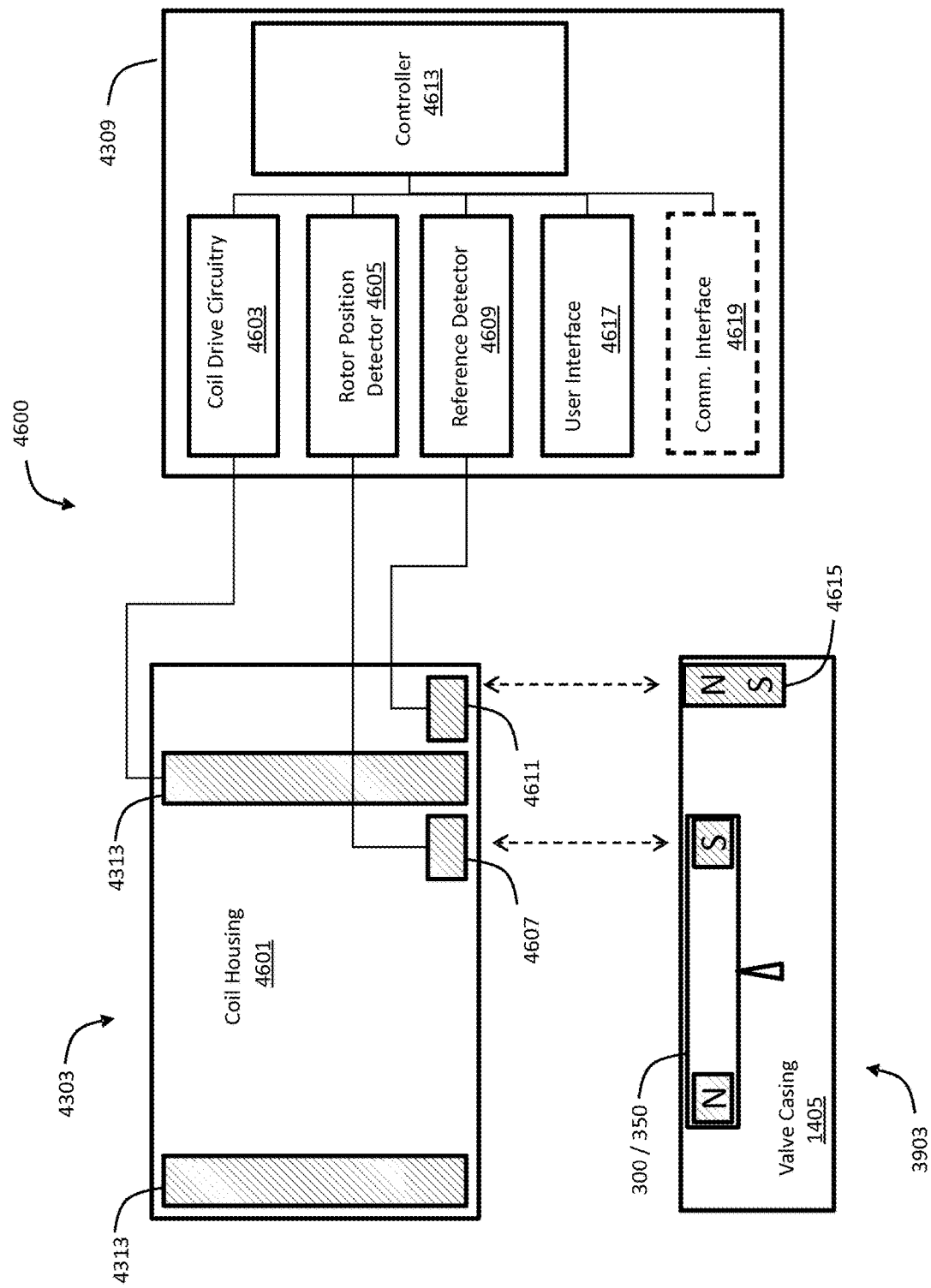
FIG. 46 is a schematic diagram of one example of a programmable control system according to aspects of the invention, the programmable control system being usable to adjust or otherwise operate any of the valve assemblies disclosed herein.

FIG. 46 is a block diagram of one example of a system 4600 including an implantable valve assembly 3903, and an external programming device including the transmitter head 4303 and control device 4309. The valve assembly 3903 may have any of the configurations discussed herein, as well as other configurations as will be appreciated by those skilled in the art, given the benefit of this disclosure. The control device 4309 is configured to allow a user, such as a physician for example, to select a pressure setting for the valve assembly 3903. The transmitter head 4303 comprises a housing 4601 and an element that applies magnetic impulses, such as the magnetic coil 4313. As described above, the magnetic impulses cause the rotor 300 or 350 to rotate within the rotor casing 305 or 359, respectively.

According to one embodiment, the control device 4309 includes a coil drive circuitry 4603 in communication with the coil 4313, and a rotor position detector 4605 in communication with first magnetic sensor(s) 4607 located in the transmitter head 4303. The control device 4309 may further include a reference detector 4609 in communication with second magnetic sensor(s) 4611 in the transmitter head 4303. The first magnetic sensor 4607 may include one or more Hall sensors. A controller 4613 may be used to provide instruction to the coil drive circuitry 4603 to drive the coil 4313 with a predetermined current, duration, cycle, etc. The controller 4613 may also receive inputs from one or more of the rotor position detector 4605 and the reference detector 4609.

The controller 4613 may be preprogrammed, for example, by computer instructions stored on a computer readable medium or device, such as a hard disk drive, an optical disk readable by an optical disk reader, a flash memory device, and the like. In at least some embodiments, the control device 4309 includes one or more of a user interface 4617 or a communication interface 4619. The control device 4303 may be operated to allow a user to adjust the valve assembly 3903 through the programmable controller and to determine a setting of the valve assembly. In some embodiments, the communications interface 4619 may be used to connect the control device 4303 to another device, such as an application server of a networked computer for similarly controlling or otherwise operating the valve assembly 3903.

Incorporating a Hall sensor or other magnetic sensor 4607 into the transmitter head 4303 allows the pressure setting of the implanted valve 3903 to be detected and communicated to the control device 4309. In one embodiment, the first magnetic sensor 4607 detects the position of the rotor 300 or 350 inside the valve assembly 3903 and translates the detected position into a pressure setting reading. Such correlations between rotational position and pressure settings can be determined for each valve according to a calibration process. The correlation can provide a look-up capability in which a rotational position can be translated into the pressure setting, and vice versa. A resolution of such pressure adjustment can be accomplished according to the techniques employed herein. For example, a number of casing teeth 311 or 361 can be selected to provide a predetermined stepwise rotation, e.g., 90 casing teeth providing 4 degree step size. Alternatively or in addition, a selection of the spring type and/or spring constant in combination with a shape of the cam can be used to control pressure variations per rotational step. In certain embodiments, the first magnetic sensor 4607 may be automated, such that the transmitter head 4303 automatically adjusts the number of pulses in response to a pressure setting selected by the physician.

As discussed above, one limitation of conventional magnetically adjustable valves is that verifying a pressure setting can entail the use of an X-ray to detect a radiopaque marker on the implanted device. According to certain embodiments, an initial orientation of the magnetic rotor can be determined with respect to a reference, such as the housing and/or casing. The pressure setting of the implanted valve 3903 may be verified by placing a compass over the patient's head in the vicinity of the implanted valve. The needle of the compass will align itself with the direction of the magnetic rotor 300 or 350, indicating the position of the rotor. The physician is then able to determine the pressure setting of the valve 3902 by considering the position of the rotor 300 or 350 relative to the housing 1405.

According to another embodiment, the implantable valve assembly 3903 further comprises a magnetic marker or reference 4615 in a fixed position on or in the housing 1405. The reference marker provides a magnetic reference of known orientation. The second magnetic sensor 4611 in the transmitter head 4303 may be used to detect the reference marker 4615 in the valve assembly 3903. The second magnetic sensor 4611 may include one or more Hall sensors. The second magnetic sensor 4611 may be used to measure a position of the reference marker 4615, or to adjust an orientation of the transmitter head 4303 with respect to the marker, e.g., at a 12 o'clock position. Having established such a reference, the position of the magnetic rotor 300 or 350 can be determined relative to the position of the reference marker 4615, thereby allowing determination of the absolute orientation of the magnetic rotor, and consequently the pressure setting of the valve. For example, the valve assembly may be calibrated, such that an approximate opening pressure of the valve element is known for each rotor position. Accordingly, the position of the magnetic rotor 300 or 350 may be precisely determined, and thereby a precise setting of the valve's threshold opening pressure may also be determined. In at least some embodiments, the rotor is free to rotate in at least one direction, beyond one full revolution, with the pressure settings repeating for each revolution. In this manner, a position of the rotor can uniquely identify a popping pressure.

Further aspects and embodiments encompass a method for adjusting the working pressure of the implantable valve assembly 3903, including the step of positioning the adjustment device in proximity to the implanted valve but external to the body. As discussed above, the adjustment device includes the transmitter head 4303 which is placed on or near the head of the patient. The control device 4309 may be used to control the polarity of the portion of the magnetic coil 4313 in closest proximity to the implanted valve 3903, changing the polarity for example, from north to south or south to north. In the case of a side-to-side magnetic rotor 300, the change in polarity of the coil 4313 within the transmitter head 4303 of the adjustment device causes the rotor to displace from side-to-side, as discussed above. In the case of an up-and-down magnetic rotor 350, the change in polarity of the coil 2201 within the transmitter head 4303 of the adjustment device causes the rotor to displace up and down, as also discussed above.

Figure 47:
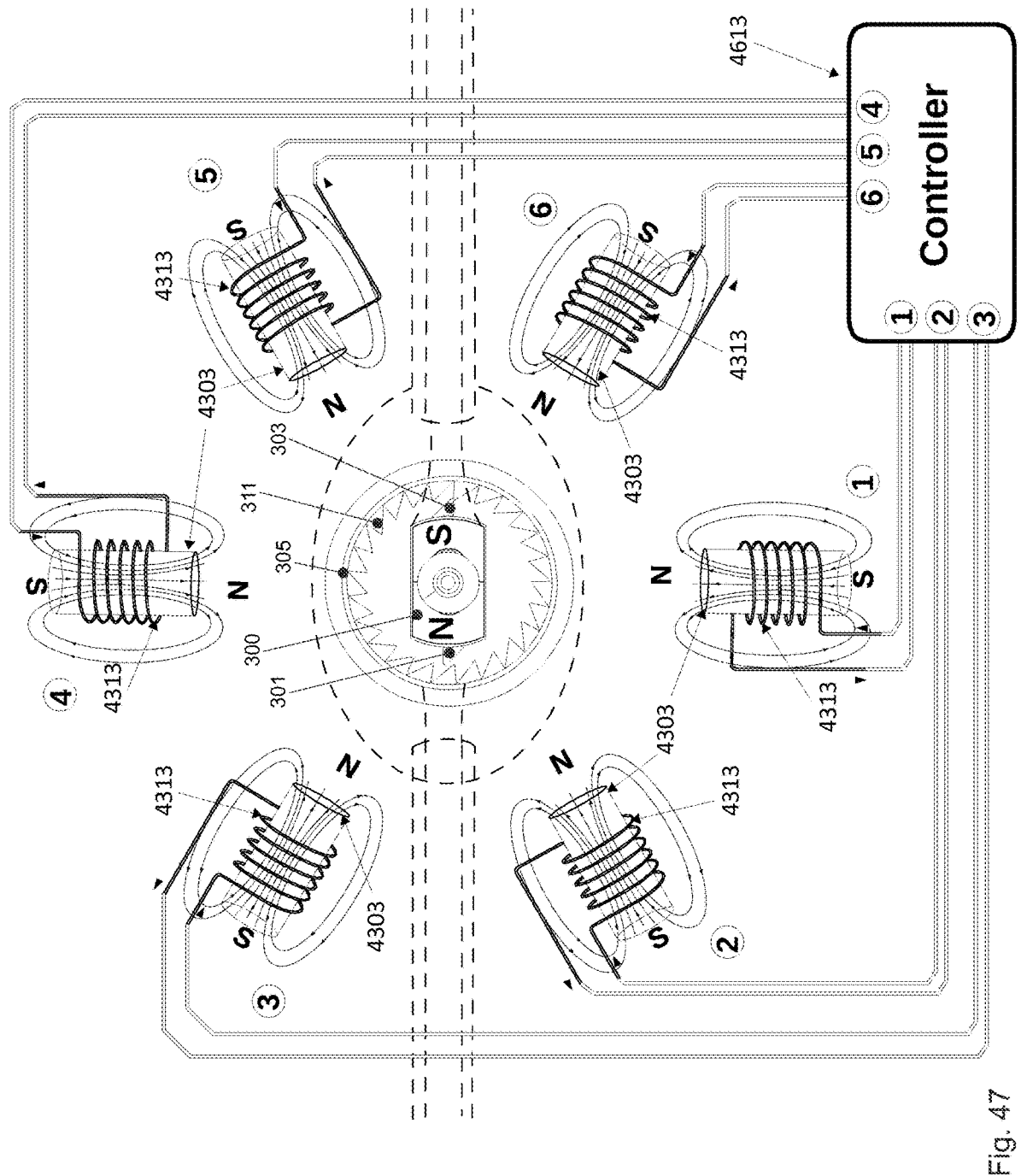
FIG. 47 is a block diagram of another example of a programmable system according to aspects of the invention; the programmable control system being usable to adjust or otherwise operate any of the valve assemblies disclosed herein.

Referring to FIG. 47, there is illustrated a block diagram of another configuration of an external programming device for controlling any of the implantable valve assemblies discussed above. In this example, the transmitter head (not shown in FIG. 47) includes an array of magnetic coils 4313 that are in communication (directly or via coil drive circuitry 4603 as discussed above) with the controller 4613. The plurality of magnetic coils 4313 may be spaced apart from one another, as schematically illustrated in FIG. 47, such that when the transmitter head housing the coils is placed near the implanted valve assembly, the coils are located at various positions around the valve assembly. The controller 4613 may include a plurality of ports (labeled (1)-(6) in FIG. 47) that are respectively coupled to each of the plurality of magnetic coils 4313. The controller 4613 may be programmed, or controlled by a user, to selectively activate one or more of the magnetic coils 4313 to actuate the magnetic rotor 300 or 350 in the valve assembly 3903. For example, the controller 4613 may selectively activate one or more of the magnetic coils 4313 based on factors such as, the orientation of the magnetic rotor 300/350 (which may be determined using the reference marker 4615 as discussed above), the current pressure setting of the valve (which may be determined as discussed above), and a desired new pressure setting of the valve.

Embodiments of the valve assembly 3903 may be implanted in a patient using well-described surgical procedures. The pressure setting of the valve can be adjusted to a desired pressure setting prior to surgical implantation. In one aspect, the working pressure can be set to be approximately equal to the patient's ventricular CSF pressure such that no pressure change occurs after the surgery. After the patient recovers from surgery, the pressure setting can be adjusted as desired. For example, in a patient suffering from NPH, the pressure setting can be decreased in order to initiate a reduction in the size of the ventricles. Additional adjustments in the pressure setting can additionally be made. For example, once the size of the ventricles had been reduced sufficiently, the pressure setting of the valve can be increased. As will be appreciated, use of the implanted valve 3903 permits the pressure setting of the valve to be externally adjusted as needed over the course of treating the patient.

In certain embodiments, a method of treating hydrocephalus includes implanting an embodiment of the valve assembly 3903 having a ventricular catheter 4305 within a ventricular cavity of the patient's brain and distal catheter 4307 installed at a remote location in the patient's body where the fluid is to drain. Remote locations of the body where CSF drains include, for example, the right atrium of the heart and the peritoneum.

In addition to hydrocephalus, there are a number of other conditions associated with the accumulation of excess fluid and that can be treated by draining the fluid into another part of the body. Such conditions include, for example, chronic pericardial effusions, chronic pulmonary effusion, pulmonary edema, ascites, and glaucoma in the eye. It is contemplated that embodiments of the valve assembly 3903 may be used in the treatment of these conditions.

The pressure settings of the valves described herein can be adjusted in many discrete steps or increments depending on the number of casing teeth 311 or 361. The amount by which the pressure setting is changed with each increment may depend on the number of casing teeth 331/361 and the maximum pressure setting of the valve. Embodiments of the valves described herein may vary in pressure from a low pressure, for example, 10 mm $H_2O$, to a high pressure, for example 400 mm $H_2O$. Most conventional valves only have pressures as high as 200 mm $H_2O$. In certain aspects, the valves may be adjusted in increments of about 10 mm $H_2O$ to about 50 mm $H_2O$.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A magnetically programmable shunt valve assembly configured to control a fluid pressure and a flow rate of fluid between an inlet and an outlet, the magnetically programmable shunt valve comprising:
- a valve seat;
- a valve element seated in the valve seat, the valve element and the valve seat together forming an aperture through which the fluid flows, the fluid pressure and the flow rate of the fluid being controlled by a size of the aperture;
- a cantilever spring configured to bias the valve element against the valve seat and thereby control the size of the aperture, the cantilever spring including a first spring arm and a second spring arm extending from a fixed point of attachment of the cantilever spring, the first spring arm having a free end that rests against the valve element;
- a rotor casing;
- a magnetically actuatable rotor disposed within the rotor casing, wherein rotation of the magnetically actuatable rotor relative to the rotor casing produces a selected pressure setting of the shunt valve assembly; and
- a cam coupled to the magnetically actuatable rotor and positioned to engage the second spring arm such that the rotation of the magnetically actuatable rotor changes a tension of the first spring arm against the valve element, thereby controlling the size of the aperture and determining the selected pressure setting of the valve, wherein the first and second spring arms and the fixed point of attachment of the cantilever spring are together configured to provide a lever effect such that a first pressure applied by the cam to the second spring arm is translated by the cantilever spring into a second pressure applied against the valve element by the first spring arm, the second pressure being less than the first pressure,
- wherein the aperture opens when a pressure of the fluid at the inlet exceeds the selected pressure setting of the shunt valve assembly so as to vent the fluid from the inlet through the aperture to the outlet.

2. The magnetically programmable shunt valve assembly of claim 1 wherein the first spring arm and the second spring arm extend substantially parallel to one another from the fixed point of attachment of the cantilever spring.

3. The magnetically programmable shunt valve assembly of claim 1 wherein the first spring arm is longer than the second spring arm.

4. The magnetically programmable shunt valve assembly of claim 1 wherein the cam is a disc cam.

5. The magnetically programmable shunt valve assembly of claim 4 wherein the cam has an inclined surface with a linear slope, and wherein the second spring arm rests against the inclined surface.

6. The magnetically programmable shunt valve assembly of claim 4 wherein the cam has an inclined surface with a non-linear slope, and wherein the second spring arm rests against the inclined surface.

7. The magnetically programmable shunt valve assembly of claim 6 wherein the non-linear slope alters a rate of increase in the selected pressure setting of the magnetically programmable shunt valve assembly as the cam rotates with the magnetically actuatable rotor.

8. The magnetically programmable shunt valve assembly of claim 7 wherein rotation of the cam in a first direction increases the selected pressure setting and rotation of the cam in a second direction, opposite to the first direction, decreases the selected pressure setting.

9. The magnetically programmable shunt valve assembly of claim 1 wherein the valve element is one of a sphere, a cone, and a cylinder.

10. The magnetically programmable shunt valve assembly of claim 1 further comprising:
- a housing, an exterior of the housing being formed of a physiologically compatible material, wherein the rotor casing, the cam, and the cantilever spring are disposed within the housing.

11. A system comprising:
- a magnetically programmable shunt valve assembly configured to control a fluid pressure and a flow rate of fluid between an inlet and an outlet and including:
  - a valve seat,
  - a valve element seated in the valve seat, the valve element and the valve seat together forming an aperture through which the fluid flows, the fluid pressure and the flow rate of the fluid being controlled by a size of the aperture,
  - a cantilever spring configured to bias the valve element against the valve seat and thereby control the size of the aperture, the cantilever spring including a first spring arm and a second spring arm extending from a fixed point of attachment of the cantilever spring, the first spring arm having a free end that rests against the valve element,
  - a rotor casing,
  - a magnetically actuatable rotor disposed within the rotor casing, wherein rotation of the magnetically actuatable rotor relative to the rotor casing produces a selected pressure setting of the shunt valve assembly, and
  - a cam coupled to the magnetically actuatable rotor and positioned to engage the second spring arm such that the rotation of the magnetically actuatable rotor changes a tension of the first spring arm against the valve element, thereby controlling the size of the aperture and determining the selected pressure setting of the shunt valve assembly, wherein the first and second spring arms and the fixed point of attachment of the cantilever spring are together configured to provide a lever effect such that a first pressure applied by the cam to the second spring arm is translated by the cantilever spring into a second pressure applied against the valve element by the first spring arm, the second pressure being less than the first pressure; and
- a magnetic valve programmer configured to magnetically induce the rotation of the magnetically actuatable rotor relative to the rotor casing to set a pressure setting of the magnetically programmable shunt valve assembly to the selected pressure setting, wherein the aperture opens when a pressure of the fluid at the inlet exceeds the selected pressure setting of the shunt valve assembly so as to vent the fluid through the aperture to the outlet.

12. The system of claim 11 further comprising:
- a compass configured such that when positioned in proximity to the magnetically programmable shunt valve assembly, a needle of the compass aligns with the magnetically actuatable rotor thereby indicating the position of the magnetically actuatable rotor and the selected pressure setting of the shunt valve assembly.

13. The system of claim 11 wherein the first spring arm and the second spring arm extend substantially parallel to one another from the fixed point of attachment of the cantilever spring.

14. The system of claim 11 wherein the first spring arm is longer than the second spring arm.

15. The system of claim 11 wherein the cam is a disc cam.

16. The system of claim 15 wherein the disc cam has an inclined surface, and wherein the second spring arm rests against the inclined surface.

17. The system of claim 11 further comprising:
a check valve coupled to the outlet, the check valve having a check pressure setting that is lower than the selected pressure setting of the magnetically programmable shunt valve assembly.

\* \* \* \* \*